(12) United States Patent
Facchetti et al.

(10) Patent No.: US 10,381,567 B2
(45) Date of Patent: Aug. 13, 2019

(54) ORGANIC SEMICONDUCTING COMPOUNDS AND RELATED OPTOELECTRONIC DEVICES

(71) Applicant: Flexterra, Inc., Skokie, IL (US)

(72) Inventors: Antonio Facchetti, Chicago, IL (US); Mark Seger, Chicago, IL (US); Ali Mohebbi, Chicago, IL (US)

(73) Assignee: Flexterra, Inc., Skokie, IL (US)

( * ) Notice: Subject to any disclaimer, the term of this patent is extended or adjusted under 35 U.S.C. 154(b) by 279 days.

(21) Appl. No.: 15/209,720

(22) Filed: Jul. 13, 2016

(65) Prior Publication Data

US 2017/0104160 A1    Apr. 13, 2017

Related U.S. Application Data

(60) Provisional application No. 62/192,336, filed on Jul. 14, 2015.

(51) Int. Cl.
| | | |
|---|---|---|
| *H01L 51/00* | (2006.01) | |
| *C08G 61/12* | (2006.01) | |
| *C07D 495/04* | (2006.01) | |
| *H01L 51/05* | (2006.01) | |
| *H01L 51/42* | (2006.01) | |
| *H01L 51/50* | (2006.01) | |

(52) U.S. Cl.
CPC ........ *H01L 51/0036* (2013.01); *C07D 495/04* (2013.01); *C08G 61/126* (2013.01); *C08G 2261/51* (2013.01); *C08G 2261/91* (2013.01); *C08G 2261/92* (2013.01); *C08G 2261/95* (2013.01); *H01L 51/0566* (2013.01); *H01L 51/4253* (2013.01); *H01L 51/5012* (2013.01); *H01L 51/5056* (2013.01); *H01L 51/5072* (2013.01)

(58) Field of Classification Search
None
See application file for complete search history.

(56) References Cited

FOREIGN PATENT DOCUMENTS

| KR | 10-2008-0096733 A | 11/2008 |
|---|---|---|
| KR | 10-0868863 B1 | 11/2008 |
| KR | 10-1096981 B1 | 12/2011 |

OTHER PUBLICATIONS

Chao Hu et al., "Dithieno[a,e]pentalene Based Conjugated Polymers: Synthesis and Characterization," Chinese Journal of Chemistry, 2013, 31, pp. 1404-1408.

(Continued)

*Primary Examiner* — Catherine S Branch
(74) *Attorney, Agent, or Firm* — McDonnell Boehnen Hulbert & Berghoff LLP

(57) ABSTRACT

The present teachings relate to new organic semiconducting compounds and their use as active materials in organic and hybrid optical, optoelectronic, and/or electronic devices such as photovoltaic cells, light emitting diodes, light emitting transistors, and field effect transistors. The present compounds can provide improved device performance, for example, as measured by power conversion efficiency, fill factor, open circuit voltage, field-effect mobility, on/off current ratios, and/or air stability when used in photovoltaic cells or transistors. The present compounds can have good solubility in common solvents enabling device fabrication via solution processes.

21 Claims, 2 Drawing Sheets

(56) References Cited

OTHER PUBLICATIONS

Masahiro Nakano et al., "Novel dibenzo[a,e]pentalene-based Conjugated Polymers," Journal of Materials Chemistry C, 2014, 2, pp. 64-70.
Zerubba U. Levi et al., "Versatile Synthesis of Pentalene Derivatives via the Pd-Catalyzed Homocoupling of Haloenynes," J.Am.Chem. Soc., 2009, 131, pp. 2796-2797.

ORGANIC SEMICONDUCTING COMPOUNDS AND RELATED OPTOELECTRONIC DEVICES

CROSS-REFERENCE TO RELATED APPLICATIONS

This application claims priority to and the benefit of U.S. Provisional Patent Application Ser. No. 62/192,336 filed on Jul. 14, 2015, the disclosure of which is incorporated by reference herein in its entirety.

BACKGROUND

A new generation of optoelectronic devices such as organic photovoltaic (OPV) devices, organic light emitting transistors (OLETs), organic light emitting diodes (OLEDs), organic thin film transistors (OTFTs), printable circuits, electrochemical capacitors, and sensors are built upon organic semiconductors as their active components. To enable high device efficiencies such as large charge carrier mobilities ($\mu$) needed for transistor/circuit operations, or efficient exciton formation/splitting that is necessary for OLED/OPV operations, it is desirable that both p-type and n-type organic semiconductor materials are available. Furthermore, these organic semiconductor-based devices should exhibit satisfactory stability in ambient conditions and should be processable in a cost-effective manner. For example, a benchmark polymer, regioregular poly(3-hexylthiophene) (rr-P3HT), can provide hole mobilities in the order of about 0.1 $cm^2/Vs$ and current modulation in the order of about $10^5$ or greater, which is close to amorphous silicon. For OPV devices based on rr-P3HT, power conversion efficiencies (PCEs) as high as about 4% have been reported. However, such performances are not sufficient for commercial applications. Besides, these optimal performances were achieved only under strict device processing conditions.

Bulk heterojunction (BHJ) solar cells commonly are considered the most promising OPV structures because they can be fabricated using roll-to-roll and large-scale production. BHJ solar cells include a photoactive layer disposed between an anode and a cathode, where the photoactive layer is composed of a blend film including a donor material and an acceptor material. State-of-the-art BHJ solar cells use fullerene-based compounds as the acceptor material. Typical fullerenes include C60 or C70 "bucky ball" compounds functionalized with solubilizing side chains such as [6,6]-phenyl-$C_{61}$-butyric acid methyl ester (PCBM) or [6,6]-phenyl-$C_{71}$-butyric acid methyl ester ($PC_{71}BM$). The most common donor material used in BHJ solar cells is poly(3-hexylthiophene) (P3HT). However, it is well known that P3HT-based cells have limited efficiency due to poor light absorption above 500 nm. Furthermore, P3HT has poor air stability.

Accordingly, the art desires new organic semiconducting compounds that can be used as active materials in various optoelectronic devices.

SUMMARY

In light of the foregoing, the present teachings provide novel monomeric, oligomeric and polymeric compounds that can be used as organic semiconductor materials. Also provided are associated devices and related methods for the preparation and use of these compounds. The present compounds can exhibit properties such as optimized optical absorption, good charge transport characteristics and chemical stability in ambient conditions, low-temperature processability, large solubility in common solvents, and processing versatility (e.g., via various solution processes). As a result, optoelectronic devices such as OPV cells that incorporate one or more of the present compounds as a photoactive layer can exhibit high performance in ambient conditions, for example, demonstrating one or more of low band-gap, high fill factor, high open circuit voltage, and high power conversion efficiency, and preferably all of these criteria. Similarly, other organic semiconductor-based devices such as OTFTs can be fabricated efficiently using the organic semiconductor materials described herein.

The present teachings also provide methods of preparing such compounds and semiconductor materials, as well as various compositions, composites, and devices that incorporate the compounds and semiconductor materials disclosed herein.

The foregoing as well as other features and advantages of the present teachings will be more fully understood from the following figures, description, examples, and claims.

BRIEF DESCRIPTION OF DRAWINGS

It should be understood that the drawings described below are for illustration purposes only. The drawings are not necessarily to scale, with emphasis generally being placed upon illustrating the principles of the present teachings. The drawings are not intended to limit the scope of the present teachings in any way.

DETAILED DESCRIPTION

Figure 1:
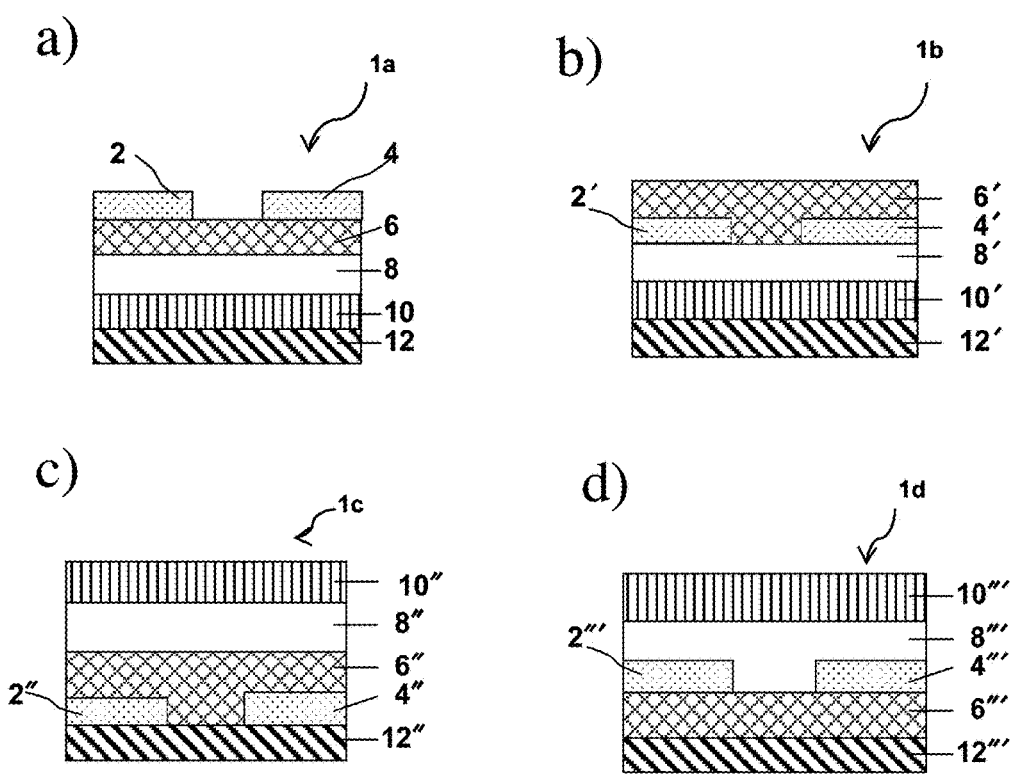
FIG. 1 illustrates four different configurations of thin film transistors: a) bottom-gate top contact, b) bottom-gate bottom-contact, c) top-gate bottom-contact, and d) top-gate top-contact; each of which can be used to incorporate one or more compounds of the present teachings, particularly as the channel (semiconductor) materials.

Throughout the application, where compositions are described as having, including, or comprising specific components, or where processes are described as having, including, or comprising specific process steps, it is contemplated that compositions of the present teachings also consist essentially of, or consist of, the recited components, and that the processes of the present teachings also consist essentially of, or consist of, the recited process steps.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition, an apparatus, or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

It should be understood that the order of steps or order for performing certain actions is immaterial so long as the present teachings remain operable. Moreover, two or more steps or actions may be conducted simultaneously.

As used herein, a "p-type semiconductor material" or a "donor" material refers to a semiconductor material, for example, an organic semiconductor material, having holes as the majority current or charge carriers. In some embodiments, when a p-type semiconductor material is deposited on a substrate, it can provide a hole mobility in excess of about $10^{-5}$ cm$^2$/Vs. In the case of field-effect devices, a p-type semiconductor also can exhibit a current on/off ratio of greater than about 10.

As used herein, an "n-type semiconductor material" or an "acceptor" material refers to a semiconductor material, for example, an organic semiconductor material, having electrons as the majority current or charge carriers. In some embodiments, when an n-type semiconductor material is deposited on a substrate, it can provide an electron mobility in excess of about $10^{-5}$ cm$^2$/Vs. In the case of field-effect devices, an n-type semiconductor also can exhibit a current on/off ratio of greater than about 10.

As used herein, "mobility" refers to a measure of the velocity with which charge carriers, for example, holes (or units of positive charge) in the case of a p-type semiconductor material and electrons (or units of negative charge) in the case of an n-type semiconductor material, move through the material under the influence of an electric field. This parameter, which depends on the device architecture, can be measured using a field-effect device or space-charge limited current measurements.

As used herein, a compound can be considered "ambient stable" or "stable at ambient conditions" when a transistor incorporating the compound as its semiconducting material exhibits a carrier mobility that is maintained at about its initial measurement when the compound is exposed to ambient conditions, for example, air, ambient temperature, and humidity, over a period of time. For example, a compound can be described as ambient stable if a transistor incorporating the compound shows a carrier mobility that does not vary more than 20% or more than 10% from its initial value after exposure to ambient conditions, including, air, humidity and temperature, over a 3 day, 5 day, or 10 day period.

As used herein, fill factor (FF) is the ratio (given as a percentage) of the actual maximum obtainable power, ($P_m$ or $V_{mp}*J_{mp}$), to the theoretical (not actually obtainable) power, ($J_{sc}*V_{oc}$). Accordingly, FF can be determined using the equation:

$$FF=(V_{mp})*(J_{mp})/(J_{sc}*V_{oc})$$

where $J_{mp}$ and $V_{mp}$ represent the current density and voltage at the maximum power point ($P_m$), respectively, this point being obtained by varying the resistance in the circuit until J*V is at its greatest value; and $J_{sc}$ and $V_{oc}$ represent the short circuit current and the open circuit voltage, respectively. Fill factor is a key parameter in evaluating the performance of solar cells. Commercial solar cells typically have a fill factor of about 0.60% or greater.

As used herein, the open-circuit voltage ($V_{oc}$) is the difference in the electrical potentials between the anode and the cathode of a device when there is no external load connected.

As used herein, the power conversion efficiency (PCE) of a solar cell is the percentage of power converted from incident light to electrical power. The PCE of a solar cell can be calculated by dividing the maximum power point ($P_m$) by the input light irradiance (E, in W/m$^2$) under standard test conditions (STC) and the surface area of the solar cell ($A_c$ in m$^2$). STC typically refers to a temperature of 25° C. and an irradiance of 1000 W/m$^2$ with an air mass 1.5 (AM 1.5) spectrum.

As used herein, a component (such as a thin film layer) can be considered "photoactive" if it contains one or more compounds that can absorb photons to produce excitons for the generation of a photocurrent.

As used herein, "solution-processable" refers to compounds (e.g., polymers), materials, or compositions that can be used in various solution-phase processes including spin-coating, printing (e.g., inkjet printing, gravure printing, offset printing and the like), spray coating, electrospray coating, drop casting, dip coating, and blade coating.

As used herein, a "semicrystalline polymer" refers to a polymer that has an inherent tendency to crystallize at least partially either when cooled from a melted state or deposited from solution, when subjected to kinetically favorable conditions such as slow cooling, or low solvent evaporation rate and so forth. The crystallization or lack thereof can be readily identified by using several analytical methods, for example, differential scanning calorimetry (DSC) and/or X-ray diffraction (XRD).

As used herein, "annealing" refers to a post-deposition heat treatment to the semicrystalline polymer film in ambient or under reduced/increased pressure for a time duration of more than 100 seconds, and "annealing temperature" refers to the maximum temperature that the polymer film is exposed to for at least 60 seconds during this process of annealing. Without wishing to be bound by any particular theory, it is believed that annealing can result in an increase of crystallinity in the polymer film, where possible, thereby increasing field effect mobility. The increase in crystallinity can be monitored by several methods, for example, by comparing the differential scanning calorimetry (DSC) or X-ray diffraction (XRD) measurements of the as-deposited and the annealed films.

As used herein, a "polymeric compound" (or "polymer") refers to a molecule including a plurality of one or more repeating units connected by covalent chemical bonds. A polymeric compound can be represented by the general formula:

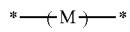

wherein M is the repeating unit or monomer. The polymeric compound can have only one type of repeating unit as well as two or more types of different repeating units. When a polymeric compound has only one type of repeating unit, it can be referred to as a homopolymer. When a polymeric compound has two or more types of different repeating units, the term "copolymer" or "copolymeric compound" can be used instead. For example, a copolymeric compound can include repeating units

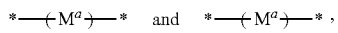

where $M^a$ and $M^b$ represent two different repeating units. Unless specified otherwise, the assembly of the repeating units in the copolymer can be head-to-tail, head-to-head, or tail-to-tail. In addition, unless specified otherwise, the copolymer can be a random copolymer, an alternating copolymer, or a block copolymer. For example, the general formula:

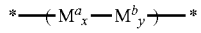

can be used to represent a copolymer of $M^a$ and $M^b$ having x mole fraction of $M^a$ and y mole fraction of $M^b$ in the copolymer, where the manner in which comonomers $M^a$ and $M^b$ is repeated can be alternating, random, regiorandom, regioregular, or in blocks. In addition to its composition, a polymeric compound can be further characterized by its degree of polymerization (n) and molar mass (e.g., number average molecular weight ($M_n$) and/or weight average molecular weight ($M_w$) depending on the measuring technique(s)).

As used herein, "halo" or "halogen" refers to fluoro, chloro, bromo, and iodo.

As used herein, "oxo" refers to a double-bonded oxygen (i.e., =O).

As used herein, "alkyl" refers to a straight-chain or branched saturated hydrocarbon group. Examples of alkyl groups include methyl (Me), ethyl (Et), propyl (e.g., n-propyl and iso-propyl), butyl (e.g., n-butyl, iso-butyl, sec-butyl, tert-butyl), pentyl groups (e.g., n-pentyl, iso-pentyl, neopentyl), hexyl groups, and the like. In various embodiments, an alkyl group can have 1 to 40 carbon atoms (i.e., $C_{1-40}$ alkyl group), for example, 1-20 carbon atoms (i.e., $C_{1-20}$ alkyl group). In some embodiments, an alkyl group can have 1 to 6 carbon atoms, and can be referred to as a "lower alkyl group." Examples of lower alkyl groups include methyl, ethyl, propyl (e.g., n-propyl and iso-propyl), and butyl groups (e.g., n-butyl, iso-butyl, sec-butyl, tert-butyl). In some embodiments, alkyl groups can be substituted as described herein. An alkyl group is generally not substituted with another alkyl group, an alkenyl group, or an alkynyl group.

As used herein, "haloalkyl" refers to an alkyl group having one or more halogen substituents. At various embodiments, a haloalkyl group can have 1 to 40 carbon atoms (i.e., $C_{1-40}$ haloalkyl group), for example, 1 to 20 carbon atoms (i.e., $C_{1-20}$ haloalkyl group). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups where all of the hydrogen atoms are replaced with halogen atoms (e.g., $CF_3$ and $C_2F_5$), are included within the definition of "haloalkyl." For example, a $C_{1-40}$ haloalkyl group can have the formula $-C_sH_{2s+1-t}X^0{}_t$, where $X^0$, at each occurrence, is F, Cl, Br or I, s is an integer in the range of 1 to 40, and t is an integer in the range of 1 to 81, provided that t is less than or equal to 2s+1. Haloalkyl groups that are not perhaloalkyl groups can be substituted as described herein.

As used herein, "alkoxy" refers to —O-alkyl group. Examples of alkoxy groups include, but are not limited to, methoxy, ethoxy, propoxy (e.g., n-propoxy and isopropoxy), t-butoxy, pentoxyl, hexoxyl groups, and the like. The alkyl group in the —O-alkyl group can be substituted as described herein.

As used herein, "alkylthio" refers to an —S-alkyl group. Examples of alkylthio groups include, but are not limited to, methylthio, ethylthio, propylthio (e.g., n-propylthio and isopropylthio), t-butylthio, pentylthio, hexylthio groups, and the like. The alkyl group in the —S-alkyl group can be substituted as described herein.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_{2-40}$ alkenyl group), for example, 2 to 20 carbon atoms (i.e., $C_{2-20}$ alkenyl group). In some embodiments, alkenyl groups can be substituted as described herein. An alkenyl group is generally not substituted with another alkenyl group, an alkyl group, or an alkynyl group.

As used herein, "alkynyl" refers to a straight-chain or branched alkyl group having one or more triple carbon-carbon bonds. Examples of alkynyl groups include ethynyl, propynyl, butynyl, pentynyl, hexynyl, and the like. The one or more triple carbon-carbon bonds can be internal (such as in 2-butyne) or terminal (such as in 1-butyne). In various embodiments, an alkynyl group can have 2 to 40 carbon atoms (i.e., $C_{2-40}$ alkynyl group), for example, 2 to 20 carbon atoms (i.e., $C_{2-20}$ alkynyl group). In some embodiments, alkynyl groups can be substituted as described herein. An alkynyl group is generally not substituted with another alkynyl group, an alkyl group, or an alkenyl group.

As used herein, a "cyclic moiety" can include one or more (e.g., 1-6) carbocyclic or heterocyclic rings. The cyclic moiety can be a cycloalkyl group, a heterocycloalkyl group, an aryl group, or a heteroaryl group (i.e., can include only saturated bonds, or can include one or more unsaturated bonds regardless of aromaticity), each including, for example, 3-24 ring atoms and optionally can be substituted as described herein. In embodiments where the cyclic moiety is a "monocyclic moiety," the "monocyclic moiety" can include a 3-14 membered aromatic or non-aromatic, carbocyclic or heterocyclic ring. A monocyclic moiety can include, for example, a phenyl group or a 5- or 6-membered heteroaryl group, each of which optionally can be substituted as described herein. In embodiments where the cyclic moiety is a "polycyclic moiety," the "polycyclic moiety" can include two or more rings fused to each other (i.e., sharing a common bond) and/or connected to each other via a spiro atom, or one or more bridged atoms. A polycyclic moiety can include an 8-24 membered aromatic or non-aromatic, carbocyclic or heterocyclic ring, such as a $C_{8-24}$ aryl group or an 8-24 membered heteroaryl group, each of which optionally can be substituted as described herein.

As used herein, a "fused ring" or a "fused ring moiety" refers to a polycyclic ring system having at least two rings where at least one of the rings is aromatic and such aromatic ring (carbocyclic or heterocyclic) has a bond in common with at least one other ring that can be aromatic or non-aromatic, and carbocyclic or heterocyclic. These polycyclic ring systems can be highly π-conjugated and optionally substituted as described herein.

As used herein, "cycloalkyl" refers to a non-aromatic carbocyclic group including cyclized alkyl, alkenyl, and alkynyl groups. In various embodiments, a cycloalkyl group can have 3 to 24 carbon atoms, for example, 3 to 20 carbon atoms (e.g., $C_{3-14}$ cycloalkyl group). A cycloalkyl group can be monocyclic (e.g., cyclohexyl) or polycyclic (e.g., containing fused, bridged, and/or spiro ring systems), where the carbon atoms are located inside or outside of the ring system. Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like. In some embodiments, cycloalkyl groups can be substituted as described herein.

As used herein, "heteroatom" refers to an atom of any element other than carbon or hydrogen and includes, for example, nitrogen, oxygen, silicon, sulfur, phosphorus, and selenium.

As used herein, "cycloheteroalkyl" refers to a non-aromatic cycloalkyl group that contains at least one ring heteroatom selected from O, S, Se, N, P, and Si (e.g., 0, S, and N), and optionally contains one or more double or triple bonds. A cycloheteroalkyl group can have 3 to 24 ring atoms, for example, 3 to 20 ring atoms (e.g., 3-14 membered cycloheteroalkyl group). One or more N, P, S, or Se atoms (e.g., N or S) in a cycloheteroalkyl ring may be oxidized (e.g., morpholine N-oxide, thiomorpholine S-oxide, thiomorpholine S,S-dioxide). In some embodiments, nitrogen or phosphorus atoms of cycloheteroalkyl groups can bear a substituent, for example, a hydrogen atom, an alkyl group, or other substituents as described herein. Cycloheteroalkyl groups can also contain one or more oxo groups, such as oxopiperidyl, oxooxazolidyl, dioxo-(1H,3H)-pyrimidyl, oxo-2(1H)-pyridyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothiophenyl, piperidinyl, piperazinyl, and the like. In some embodiments, cycloheteroalkyl groups can be substituted as described herein.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_{6-20}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —$C_6F_5$), are included within the definition of "haloaryl." In certain embodiments, an aryl group is substituted with another aryl group and can be referred to as a biaryl group. Each of the aryl groups in the biaryl group can be substituted as disclosed herein.

As used herein, "arylalkyl" refers to an alkylaryl group, where the arylalkyl group is covalently linked to the defined chemical structure via the alkyl group. An arylalkyl group is within the definition of a —Y—$C_{6-14}$ aryl group, where Y is as defined herein. An example of an arylalkyl group is a benzyl group (—$CH_2$—$C_6H_5$). An arylalkyl group can be optionally substituted, i.e., the aryl group and/or the alkyl group, can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of heteroaryl groups include, for example, the 5- or 6-membered monocyclic and 5-6 bicyclic ring systems shown below:

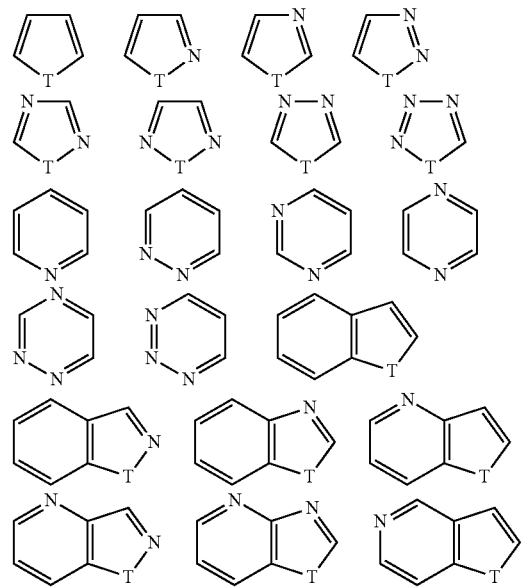

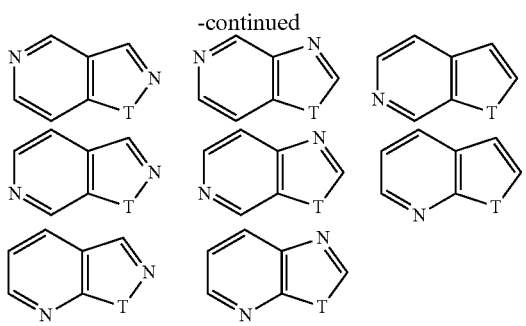

where T is O, S, NH, N-alkyl, N-aryl, N-(arylalkyl) (e.g., N-benzyl), $SiH_2$, SiH(alkyl), $Si(alkyl)_2$, SiH(arylalkyl), $Si(arylalkyl)_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

Compounds of the present teachings can include a "divalent group" defined herein as a linking group capable of forming a covalent bond with two other moieties. For example, compounds of the present teachings can include a divalent $C_{1-20}$ alkyl group (e.g., a methylene group), a divalent $C_{2-20}$ alkenyl group (e.g., a vinylyl group), a divalent $C_{2-20}$ alkynyl group (e.g., an ethynylyl group). a divalent $C_{6-14}$ aryl group (e.g., a phenylyl group); a divalent 3-14 membered cycloheteroalkyl group (e.g., a pyrrolidylyl), and/or a divalent 5-14 membered heteroaryl group (e.g., a thienylyl group). Generally, a chemical group (e.g., Ar) is understood to be divalent by the inclusion of the two bonds before and after the group.

The electron-donating or electron-withdrawing properties of several hundred of the most common substituents, reflecting all common classes of substituents have been determined, quantified, and published. The most common quantification of electron-donating and electron-withdrawing properties is in terms of Hammett σ values. Hydrogen has a Hammett σ value of zero, while other substituents have Hammett σ values that increase positively or negatively in direct relation to their electron-withdrawing or electron-donating characteristics. Substituents with negative Hammett σ values are considered electron-donating, while those with positive Hammett σ values are considered electron-withdrawing. See Lange's Handbook of Chemistry, 12th ed., McGraw Hill, 1979, Table 3-12, pp. 3-134 to 3-138, which lists Hammett σ values for a large number of commonly encountered substituents and is incorporated by reference herein.

It should be understood that the term "electron-accepting group" can be used synonymously herein with "electron acceptor" and "electron-withdrawing group". In particular, an "electron-withdrawing group" ("EWG") or an "electron-accepting group" or an "electron-acceptor" refers to a functional group that draws electrons to itself more than a hydrogen atom would if it occupied the same position in a molecule. Examples of electron-withdrawing groups include, but are not limited to, halogen or halo (e.g., F, Cl, Br, I), $—NO_2$, $—CN$, $—NC$, $—S(R^o)_2{}^+$, $—N(R^o)_3{}^+$, $—SO_3H$, $—SO_2R^o$, $—SO_3R^o$, $—SO_2NHR^o$, $—SO_2N(R^o)_2$, $—COOH$, $—COR^o$, $—COOR^o$, $—CONHR^o$, $CON(R^o)_2$, $C_{1-40}$ haloalkyl groups, $C_{6-14}$ aryl groups, and 5-14 membered electron-poor heteroaryl groups; where $R^o$ is a $C_{1-20}$ alkyl group, a $C_{2-20}$ alkenyl group, a $C_{2-20}$ alkynyl group, a $C_{1-20}$ haloalkyl group, a $C_{1-20}$ alkoxy group, a $C_{6-14}$ aryl group, a $C_{3-14}$ cycloalkyl group, a 3-14 membered cycloheteroalkyl group, and a 5-14 membered heteroaryl group, each of which can be optionally substituted as described herein. For example, each of the $C_{1-20}$ alkyl group, the $C_{2-20}$ alkenyl group, the $C_{2-20}$ alkynyl group, the $C_{1-20}$ haloalkyl group, the $C_{1-20}$ alkoxy group, the $C_{6-14}$ aryl group, the $C_{3-14}$ cycloalkyl group, the 3-14 membered cycloheteroalkyl group, and the 5-14 membered heteroaryl group can be optionally substituted with 1-5 small electron-withdrawing groups such as F, Cl, Br, $—NO_2$, $—CN$, $—NC$, $—S(R^o)_2{}^+$, $—N(R^o)_3{}^+$, $—SO_3H$, $—SO_2R^o$, $—SO_3R^o$, $SO_2NHR^o$, $SO_2N(R^o)_2$, $—COOH$, $—COR^o$, $—COOR^o$, $—CONHR^o$, and $—CON(R^o)_2$.

It should be understood that the term "electron-donating group" can be used synonymously herein with "electron donor". In particular, an "electron-donating group" or an "electron-donor" refers to a functional group that donates electrons to a neighboring atom more than a hydrogen atom would if it occupied the same position in a molecule. Examples of electron-donating groups include $—OH$, $—OR^o$, $—NH_2$, $—NHR^o$, $—N(R^o)_2$, and 5-14 membered electron-rich heteroaryl groups, where $R^o$ is a $C_{1-20}$ alkyl group, a $C_{2-20}$ alkenyl group, a $C_{2-20}$ alkynyl group, a $C_{6-14}$ aryl group, or a $C_{3-14}$ cycloalkyl group.

Various unsubstituted heteroaryl groups can be described as electron-rich (or π-excessive) or electron-poor (or π-deficient). Such classification is based on the average electron density on each ring atom as compared to that of a carbon atom in benzene. Examples of electron-rich systems include 5-membered heteroaryl groups having one heteroatom such as furan, pyrrole, and thiophene; and their benzofused counterparts such as benzofuran, benzopyrrole, and benzothiophene. Examples of electron-poor systems include 6-membered heteroaryl groups having one or more heteroatoms such as pyridine, pyrazine, pyridazine, and pyrimidine; as well as their benzofused counterparts such as quinoline, isoquinoline, quinoxaline, cinnoline, phthalazine, naphthyridine, quinazoline, phenanthridine, acridine, and purine. Mixed heteroaromatic rings can belong to either class depending on the type, number, and position of the one or more heteroatom(s) in the ring. See Katritzky, A. R and Lagowski, J. M., *Heterocyclic Chemistry* (John Wiley & Sons, New York, 1960).

At various places in the present specification, substituents are disclosed in groups or in ranges. It is specifically intended that the description include each and every individual subcombination of the members of such groups and ranges. For example, the term "$C_{1-6}$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$ alkyl. By way of other examples, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20. Additional examples include that the phrase "optionally substituted with 1-5 substituents" is specifically intended to individually disclose a chemical group that can include 0, 1, 2, 3, 4, 5, 0-5, 0-4, 0-3, 0-2, 0-1, 1-5, 1-4, 1-3, 1-2, 2-5, 2-4, 2-3, 3-5, 3-4, and 4-5 substituents.

Compounds described herein can contain an asymmetric atom (also referred as a chiral center) and some of the compounds can contain two or more asymmetric atoms or centers, which can thus give rise to optical isomers (enantiomers) and geometric isomers (diastereomers). The present teachings include such optical and geometric isomers, including their respective resolved enantiomerically or diastereomerically pure isomers (e.g., (+) or (−) stereoisomer) and their racemic mixtures, as well as other mixtures of the enantiomers and diastereomers. In some embodiments, optical isomers can be obtained in enantiomerically enriched or pure form by standard procedures known to those skilled in the art, which include, for example, chiral separation, diastereomeric salt formation, kinetic resolution, and asymmetric synthesis. The present teachings also encompass cis- and trans-isomers of compounds containing alkenyl moieties (e.g., alkenes, azo, and imines). It also should be understood that the compounds of the present teachings encompass all possible regioisomers in pure form and mixtures thereof. In some embodiments, the preparation of the present compounds can include separating such isomers using standard separation procedures known to those skilled in the art, for example, by using one or more of column chromatography, thin-layer chromatography, simulated moving-bed chromatography, and high-performance liquid chromatography. However, mixtures of regioisomers can be used similarly to the uses of each individual regioisomer of the present teachings as described herein and/or known by a skilled artisan.

It is specifically contemplated that the depiction of one regioisomer includes any other regioisomers and any regioisomeric mixtures unless specifically stated otherwise.

As used herein, a "leaving group" ("LG") refers to a charged or uncharged atom (or group of atoms) that can be displaced as a stable species as a result of, for example, a substitution or elimination reaction. Examples of leaving groups include, but are not limited to, halogen (e.g., Cl, Br, I), azide ($N_3$), thiocyanate (SCN), nitro ($NO_2$), cyanate (CN), water ($H_2O$), ammonia ($NH_3$), and sulfonate groups (e.g., $OSO_2$—R, wherein R can be a $C_{1-10}$ alkyl group or a $C_{6-14}$ aryl group each optionally substituted with 1-4 groups independently selected from a $C_{1-10}$ alkyl group and an electron-withdrawing group) such as tosylate (toluenesulfonate, OTs), mesylate (methanesulfonate, OMs), brosylate (p-bromobenzenesulfonate, OBs), nosylate (4-nitrobenzenesulfonate, ONs), and triflate (trifluoromethanesulfonate, OTf).

Throughout the specification, structures may or may not be presented with chemical names. Where any question arises as to nomenclature, the structure prevails.

The present teachings relate to monomeric, oligomeric, and polymeric compounds that can be used as organic semiconductor materials. The present compounds can have good solubility in various common organic solvents and good stability in air. When incorporated into optical, electronic or optoelectronic devices including, but not limited to, organic photovoltaic or solar cells, organic light emitting diodes, and organic field effect transistors, the present compounds can confer various desirable performance properties.

In one aspect, the present teachings provide compounds represented by formula (I) and formula (II):

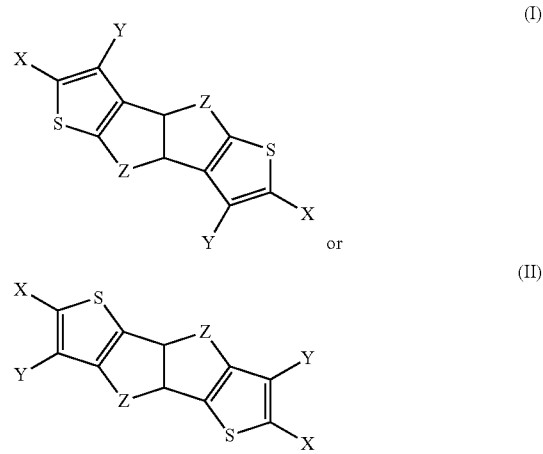

wherein:

X, at each occurrence, independently can be selected from W, $R^1$, —$(Ar^1)_p$—W, and —$(Ar^1)_p$—$R^1$;

Y, at each occurrence, independently can be selected from halogen, $R^1$, and —$(Ar^1)_p R^1$;

Z, at each occurrence, independently can be selected from —C(O)—, —C(W)=, and —C($R^2$)=;

W can be selected from halogen, —$OSO_2R^3$, —OPO$(OR^4)_2$, —Sn$(R^5)_3$, —B$(R^6)_2$, $MgW^1$, $ZnW^1$, —C=$CH_2$, and —C≡CH;

$W^1$ can be selected from Cl, Br and I;

$Ar^1$, at each occurrence, independently can be an optionally substituted divalent $C_{6-20}$ aryl or 5-20 membered heteroaryl group;

$R^1$ can be selected from H, —CN, —$NO_2$, —OR, —SR, —C(O)OR, —C(O)R, —Si(R)$_3$, and R; wherein R is selected from the group consisting of a $C_{1-40}$ alkyl group, a $C_{1-40}$ haloalkyl group, a $C_{2-40}$ alkenyl group, and a $C_{2-40}$ alkynyl group;

$R^2$ can be selected from $R^1$, —$(Ar^1)_p$—W, and —$(Ar^1)_p$—$R^1$;

$R^3$ can be selected from a $C_{1-6}$ alkyl group, a $C_{1-6}$ perfluoroalkyl group, and a benzyl group;

$R^4$ can be H or a $C_{1-6}$ alkyl group;

$R^5$ can be a $C_{1-6}$ alkyl group or a phenyl group;

$R^6$ can be selected from H, OH, an —O—$C_{1-6}$ alkyl group, and a $C_{1-6}$ alkyl group; and p can be 1, 2, 3 or 4.

For some embodiments of the compounds represented by formula (I) or formula (II), X can be $R^1$ or —$(Ar^1)_p$—$R^1$; and Z can be —C($R^1$)= or —C[—$(Ar^1)_p$—$R^1$)]=. In certain embodiments, $Ar^1$, at each occurrence, independently can be an optionally substituted monocyclic 5-membered or 6-membered aryl or heteroaryl group. For example, $Ar^1$ can be selected from the group consisting of a phenyl group, a thienyl group, a thiazolyl group, an isothiazolyl group, a thiadiazolyl group, a furyl group, an oxazolyl group, an isoxazolyl group, an oxadiazolyl group, a pyrrolyl group, a triazolyl group, a tetrazolyl group, a pyrazolyl group, an imidazolyl group, a pyridyl group, a pyrimidyl group, a pyridazinyl group, and a pyrazinyl group, each of which can be optionally substituted as described herein. In other embodiments, $Ar^1$ can be a bicyclic or tricyclic moiety including at least one of the foregoing monocyclic groups fused with either one or two phenyl or thienyl groups. Any of the foregoing monocyclic, bicyclic or tricyclic groups can be optionally substituted with 1-4 $R^7$ groups, wherein each $R^7$ independently can be selected from halogen, —CN, —$NO_2$, —OR, —SR, —C(O)OR, —C(O)R, —Si(R)$_3$, and R; wherein R is selected from the group consisting of a $C_{1-40}$ alkyl group, a $C_{1-40}$ haloalkyl group, a $C_{2-40}$ alkenyl group, and a $C_{2-40}$ alkynyl group.

In particular embodiments, Z can be —C[(—$(Ar^1)_p$—$R^1$)]=, wherein at least one of the $Ar^1$ groups is an optionally substituted thienyl group. Accordingly, compounds of formula (I) can include compounds represented by the formulae below:

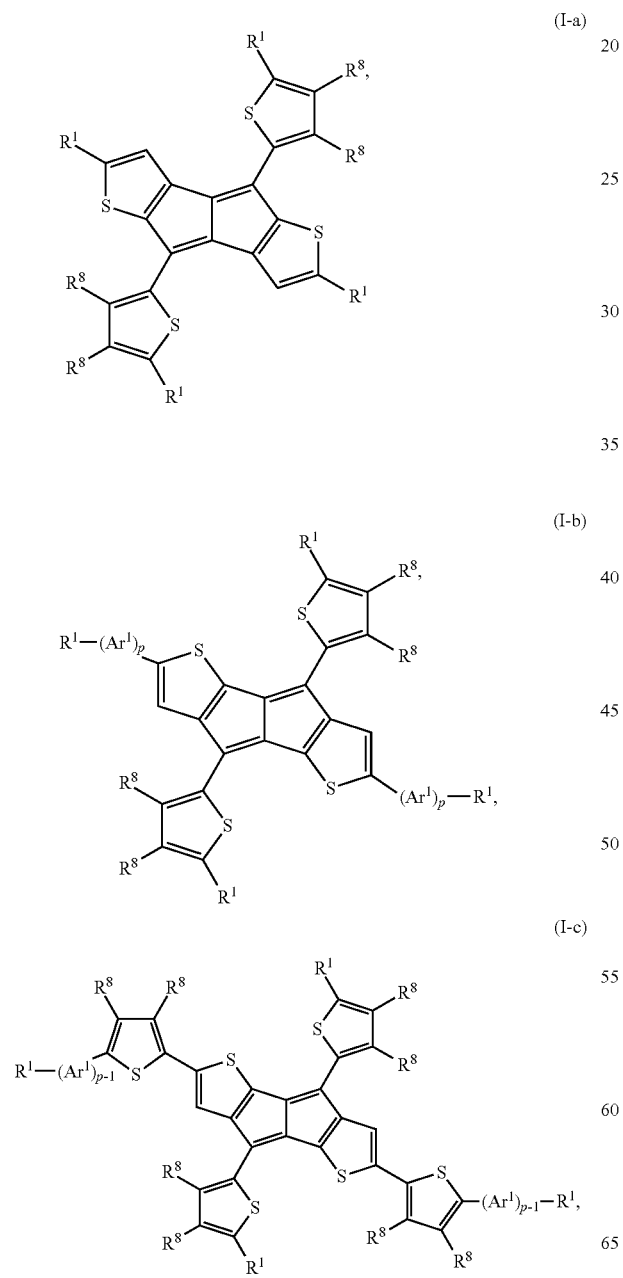

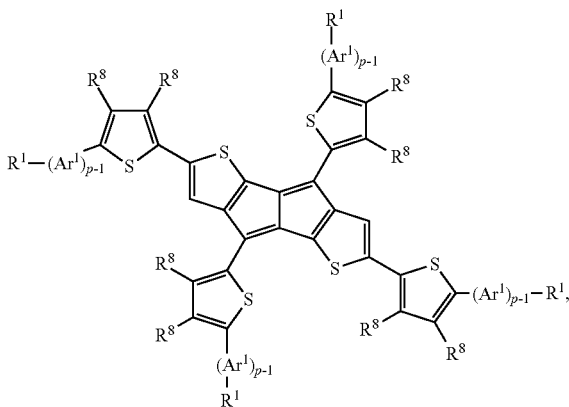

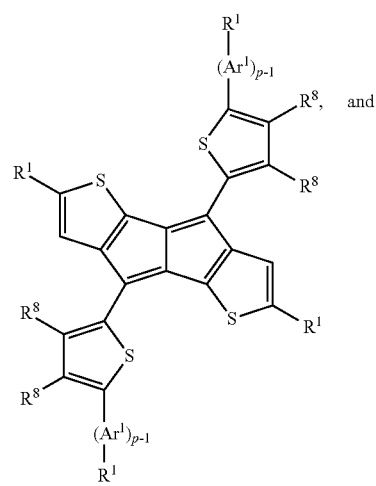

and compounds of formula (II) can include compounds represented by the formulae below:

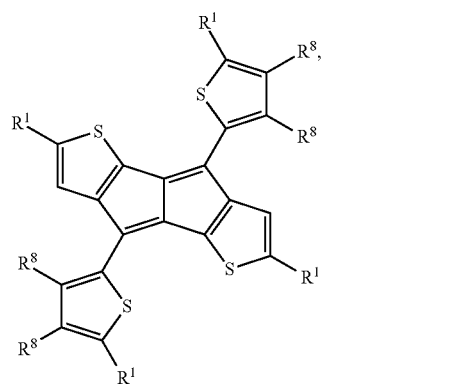
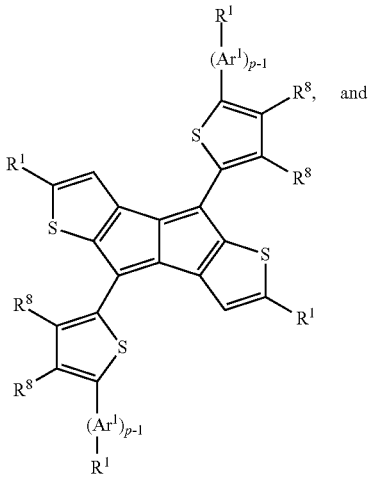

wherein $R^8$, at each occurrence, independently can be H or $R^7$; and $R^1$ is as defined herein. For example, each $R^1$ independently can be selected from the group consisting of H, a linear or branched $C_{1-40}$ alkyl group, a linear or branched $C_{1-40}$ haloalkyl group, a linear or branched $C_{2-40}$ alkenyl group, a linear or branched $C_{2-40}$ alkynyl group, a linear or branched $C_{1-40}$ alkoxy group, and a linear or branched $C_{1-40}$ thioalkyl group; and each $R^8$ independently can be selected from the group consisting of H, F, Cl, a linear or branched $C_{1-40}$ alkyl group, a linear or branched $C_{1-40}$ haloalkyl group, a linear or branched $C_{2-40}$ alkenyl group, a linear or branched $C_{2-40}$ alkynyl group, a linear or branched $C_{1-40}$ alkoxy group, and a linear or branched $C_{1-40}$ thioalkyl group.

Illustrative compounds include:
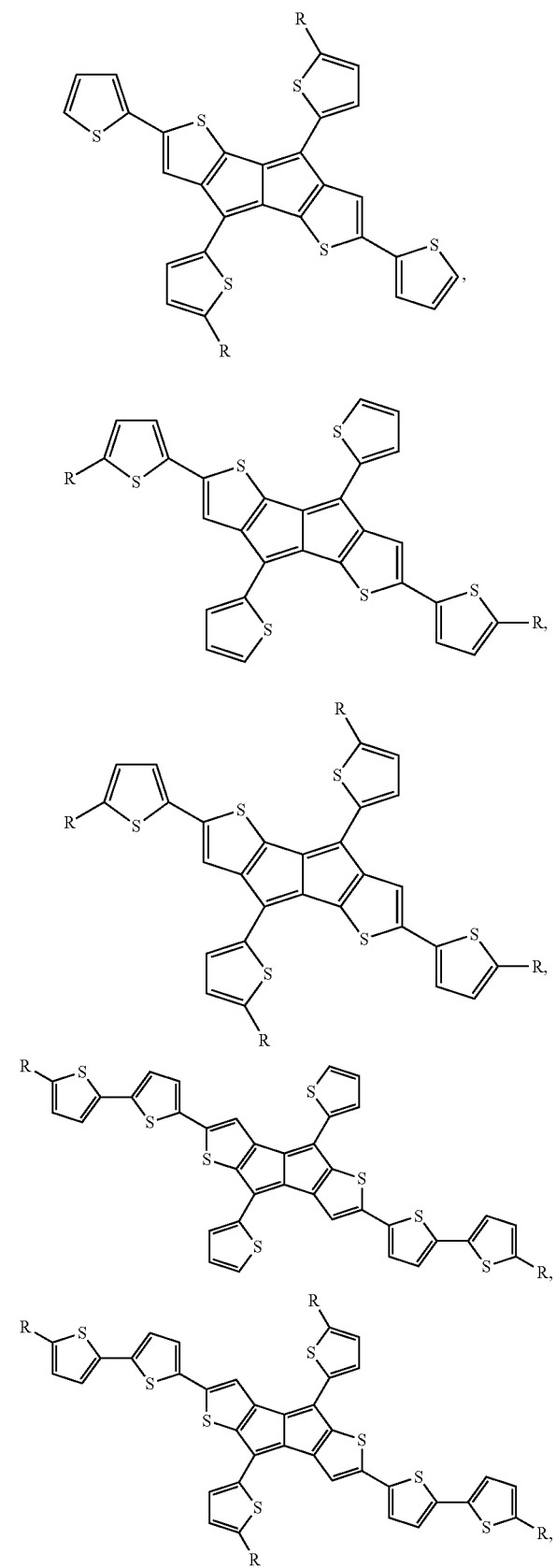
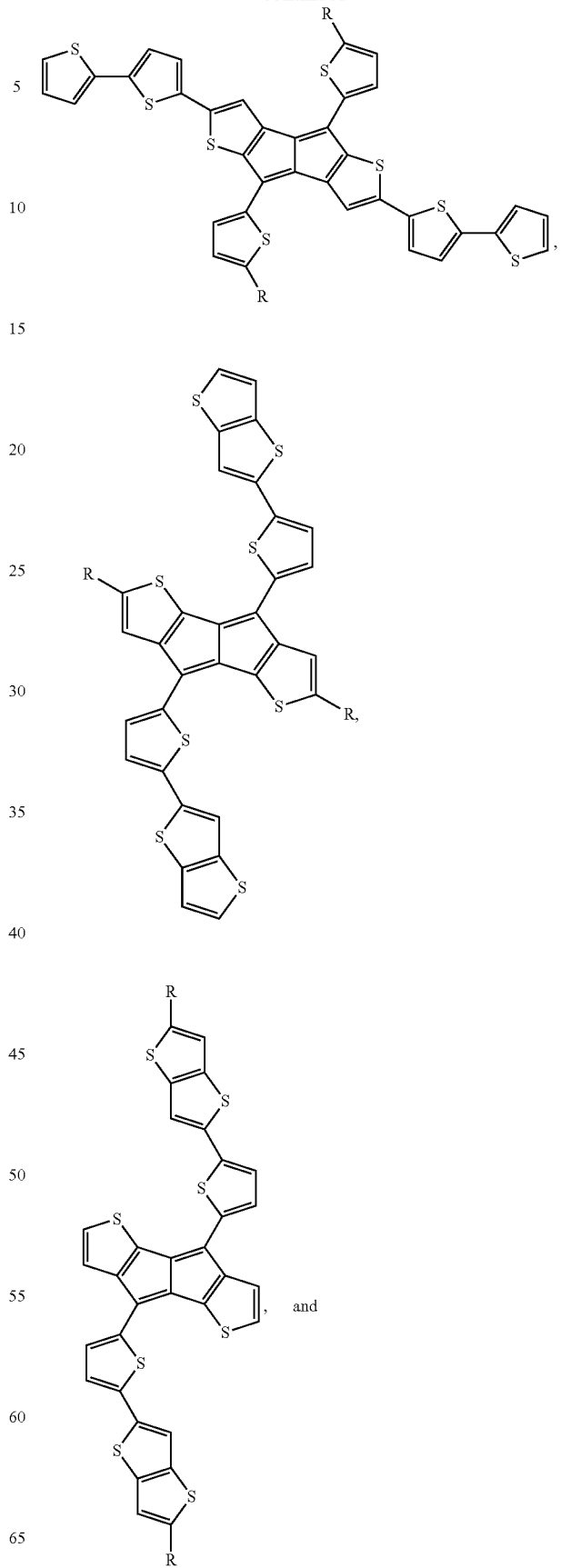

-continued

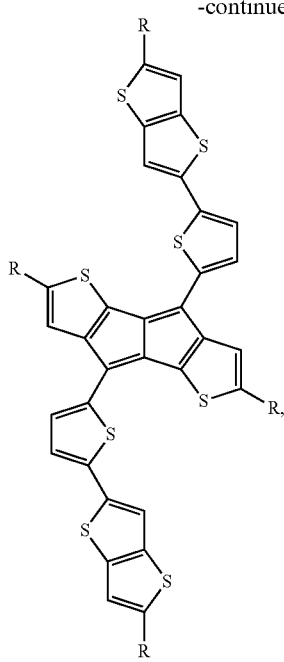

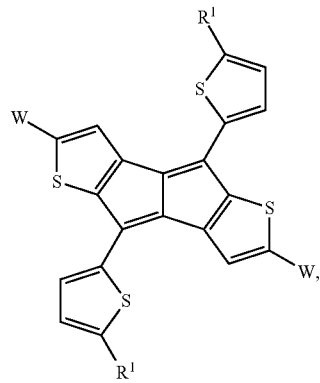
(I-g)

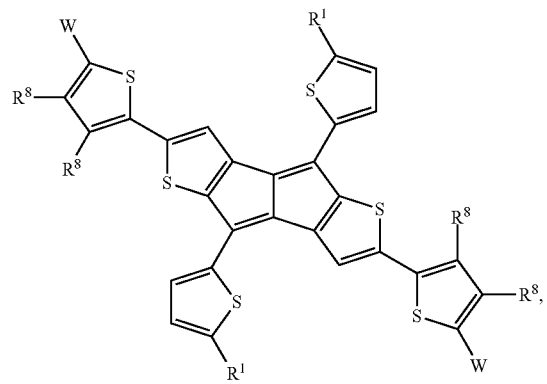
(I-h)

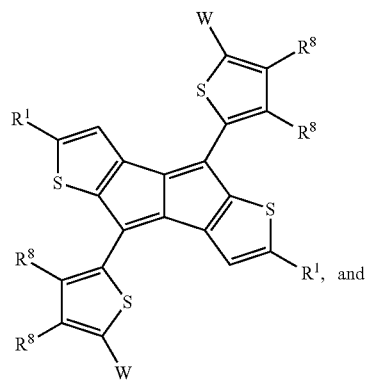
(I-i)

, and

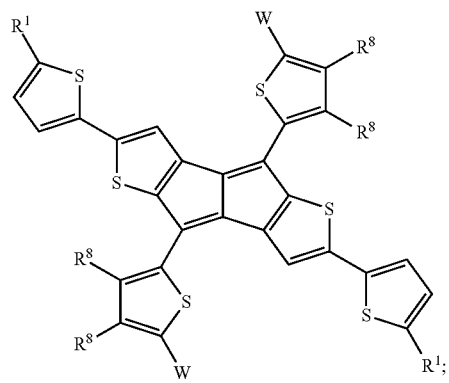
(I-j)

;

where R, at each occurrence, independently can be a linear or branched $C_{1-40}$ alkyl group or $C_{1-40}$ haloalkyl group.

In some embodiments, compounds represented by formula (I) and formula (II) can include one or more reactive groups (e.g., for polymerization). For example, X can be W or —$(Ar^1)_p$W; or Z can be —C(W)= or —C[(—$(Ar^1)_p$—W)]=. In certain embodiments, $Ar^1$, at each occurrence, independently can be an optionally substituted monocyclic 5-membered or 6-membered aryl or heteroaryl group. For example, $Ar^1$ can be selected from the group consisting of a phenyl group, a thienyl group, a thiazolyl group, an isothiazolyl group, a thiadiazolyl group, a furyl group, an oxazolyl group, an isoxazolyl group, an oxadiazolyl group, a pyrrolyl group, a triazolyl group, a tetrazolyl group, a pyrazolyl group, an imidazolyl group, a pyridyl group, a pyrimidyl group, a pyridazinyl group, and a pyrazinyl group, each of which can be optionally substituted as described herein. In other embodiments, $Ar^1$ can be a bicyclic or tricyclic moiety including at least one of the foregoing monocyclic groups fused with either one or two phenyl or thienyl groups. Any of the foregoing monocyclic, bicyclic or tricyclic groups can be optionally substituted with 1-4 $R^7$ groups, wherein each $R^7$ independently can be selected from halogen, —CN, —$NO_2$, —OR, —SR, —C(O)OR, —C(O)R, —Si(R)$_3$, and R; wherein R is selected from the group consisting of a $C_{1-40}$ alkyl group, a $C_{1-40}$ haloalkyl group, a $C_{2-40}$ alkenyl group, and a $C_{2-40}$ alkynyl group.

In particular embodiments, $Ar^1$ can be an optionally substituted thienyl group. Accordingly, compounds of formula (I) can include compounds represented by the formulae below:

and compounds of formula (II) can include compounds represented by the formulae below:

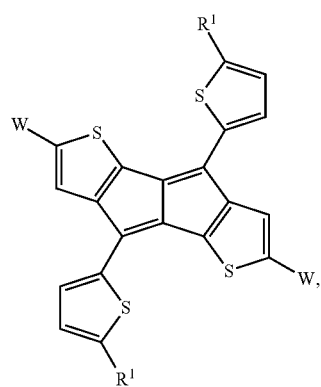
(II-g)

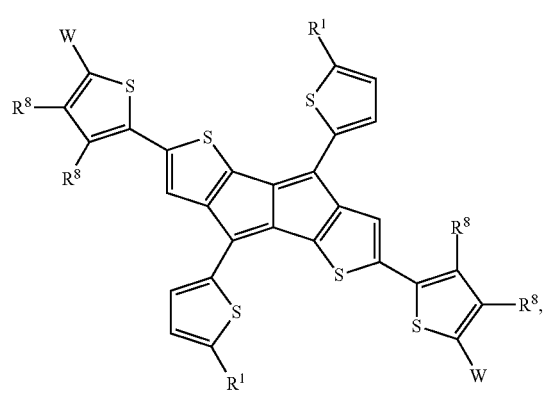
(II-h)

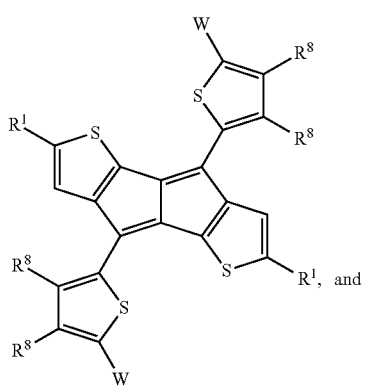
(II-i)

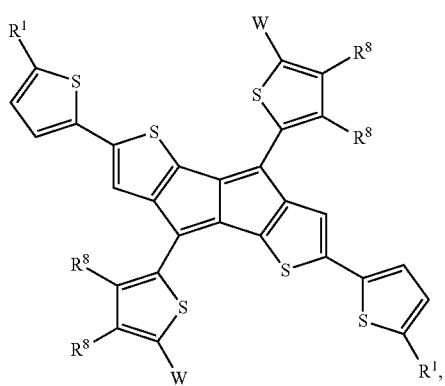
(II-j)

wherein W, $R^1$ and $R^8$ are as defined herein. In particular embodiments, W can be selected from the group consisting of Cl, Br, I, —$OSO_2CF_3$ (OTf), —$OSO_2CH_3$ (OMs), —Sn$(CH_3)_3$, —Sn$(Bu)_3$, —$B(H)_2$, —$B(OH)_2$, —$B(OBu)_2$, —MgBr, and —ZnCl; wherein Bu represents a butyl group. In particular embodiments, each $R^1$ independently can be selected from the group consisting of H, a linear or branched $C_{1-40}$ alkyl group, a linear or branched $C_{1-40}$ haloalkyl group, a linear or branched $C_{2-40}$ alkenyl group, a linear or branched $C_{2-40}$ alkynyl group, a linear or branched $C_{1-40}$ alkoxy group, and a linear or branched $C_{1-40}$ thioalkyl group; and each $R^8$ independently can be selected from the group consisting of H, F, Cl, a linear or branched $C_{1-40}$ alkyl group, a linear or branched $C_{1-40}$ haloalkyl group, a linear or branched $C_{2-40}$ alkenyl group, a linear or branched $C_{2-40}$ alkynyl group, a linear or branched $C_{1-40}$ alkoxy group, and a linear or branched $C_{1-40}$ thioalkyl group.

Compounds of formula (I) and formula (II) having W groups such as those described above can be used to prepare various oligomeric and polymeric compounds. Accordingly, in another aspect, the present teachings provide oligomeric and polymeric compounds including a repeating unit of the formula:

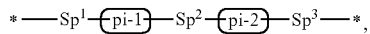

wherein:

pi-1 can be selected from:

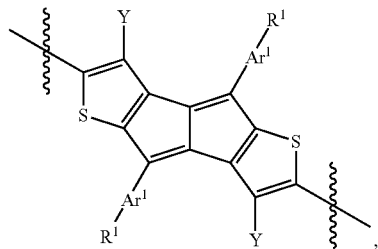

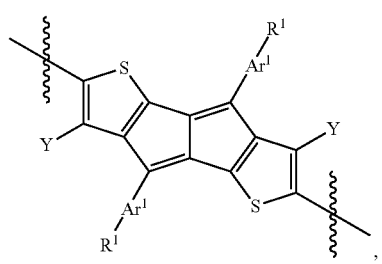

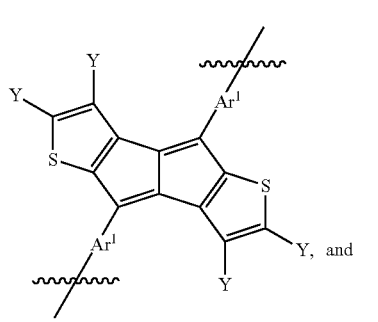

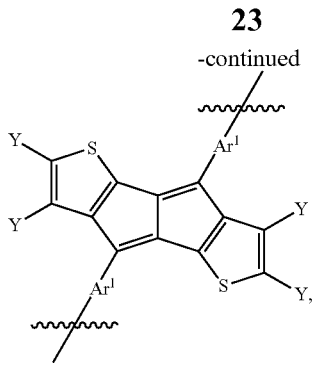

wherein:

Y, at each occurrence, independently can be selected from halogen, $R^1$, and $-(Ar^1)_p-R^1$;

$Ar^1$, at each occurrence, independently can be an optionally substituted divalent $C_{6-20}$ aryl or 5-20 membered heteroaryl group;

$R^1$, at each occurrence, independently can be selected from H, —CN, —$NO_2$, —OR, —SR, —C(O)OR, —C(O)R, —Si(R)$_3$, and R; wherein R is selected from the group consisting of a $C_{1-40}$ alkyl group, a $C_{1-40}$ haloalkyl group, a $C_{2-40}$ alkenyl group, and a $C_{2-40}$ alkynyl group; and p is 1, 2, 3 or 4;

pi-2 can be a covalent bond or an optionally substituted conjugated polycyclic moiety that is different from π-1; and $Sp^1$, $Sp^2$, and $Sp^3$ independently can be a covalent bond or a conjugated spacer group comprising at least one of a conjugated linear linker and an optionally substituted conjugated monocyclic moiety.

In some embodiments, pi-1 can be selected from:

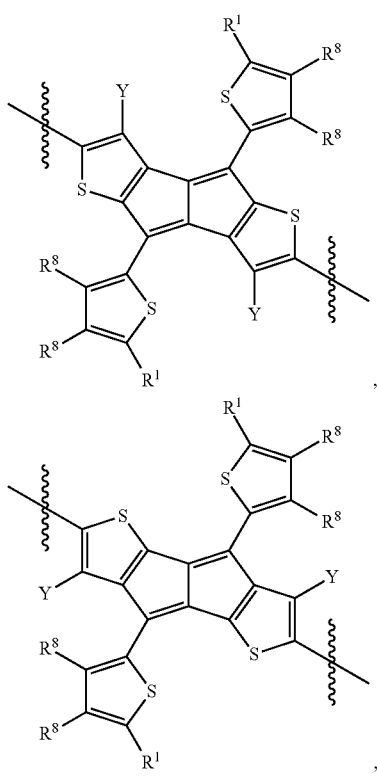

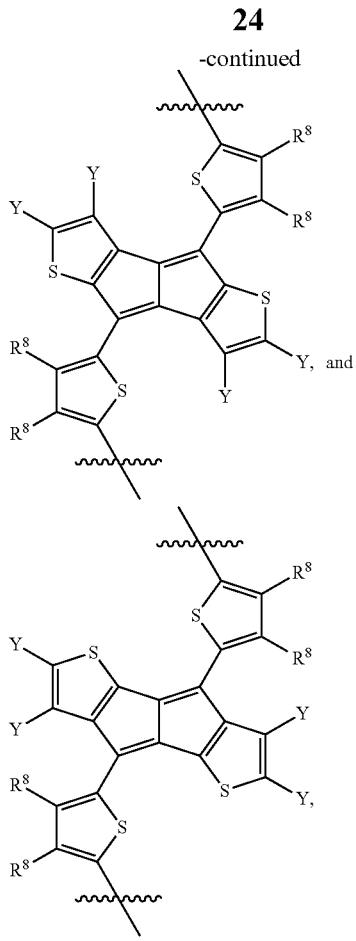

wherein $R^8$, at each occurrence, independently can be H or $R^7$; Y and $R^1$ is as defined herein. For example, each $R^1$ independently can be selected from the group consisting of H, a linear or branched $C_{1-40}$ alkyl group, a linear or branched $C_{1-40}$ haloalkyl group, a linear or branched $C_{2-40}$ alkenyl group, a a linear or branched $C_{2-40}$ alkynyl group, a linear or branched $C_{1-40}$ alkoxy group, and a linear or branched $C_{1-40}$ thioalkyl group; and each $R^8$ independently can be selected from the group consisting of H, F, Cl, a linear or branched $C_{1-40}$ alkyl group, a linear or branched $C_{1-40}$ haloalkyl group, a linear or branched $C_{2-40}$ alkenyl group, a linear or branched $C_{2-40}$ alkynyl group, a linear or branched $C_{1-40}$ alkoxy group, and a linear or branched $C_{1-40}$ thioalkyl group; and each Y independently can be selected from the group consisting of H, F, Cl, a linear or branched $C_{1-40}$ alkyl group, a linear or branched $C_{1-40}$ haloalkyl group, a linear or branched $C_{2-40}$ alkenyl group, a linear or branched $C_{2-40}$ alkynyl group, a linear or branched $C_{1-40}$ alkoxy group, and a linear or branched $C_{1-40}$ thioalkyl group.

The conjugated spacer groups $Sp^1$, $Sp^2$, and $Sp^3$ can be identical or different and independently can be selected from the group consisting of —$(Ar)_m$—, —Z—, —$(Ar)_m$—Z—, —$(Ar)_m$—Z—$(Ar)_m$—, and a covalent bond, wherein each Ar independently is an optionally substituted conjugated monocyclic moiety; Z is a conjugated linear linker; and m is 1, 2, 3, 4 or 5.

In various embodiments, each Ar independently can be an optionally substituted monocyclic 5-membered or 6-membered aryl or heteroaryl group. For example, Ar can be selected from the group consisting of a phenyl group, a thienyl group, a thiazolyl group, an isothiazolyl group, a thiadiazolyl group, a furyl group, an oxazolyl group, an isoxazolyl group, an oxadiazolyl group, a pyrrolyl group, a triazolyl group, a tetrazolyl group, a pyrazolyl group, an imidazolyl group, a pyridyl group, a pyrimidyl group, a pyridazinyl group, and a pyrazinyl group, each of which optionally can be substituted with 1-4 $R^3$ groups independently selected from a halogen, CN, oxo, $=C(CN)_2$, a $C_{1-40}$ alkyl group, a $C_{1-40}$ haloalkyl group, a $C_{1-40}$ alkoxy group, and a $C_{1-40}$ alkylthio group.

In various embodiments, Z can be selected from the group consisting of:

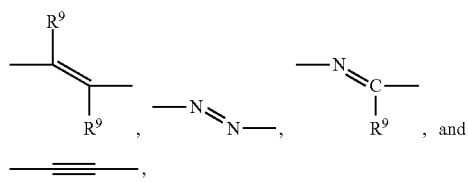

wherein each $R^9$ independently is selected from the group consisting of H, a halogen, CN, a $C_{1-40}$ alkyl group, a $C_{1-40}$ haloalkyl group, a $C_{1-40}$ alkoxy group, and a $C_{1-40}$ alkylthio group.

In certain embodiments, $Sp^1$ and $Sp^2$ can be $-(Ar)_m-$. Accordingly, certain embodiments of the present polymers can have a repeating unit of the formula:

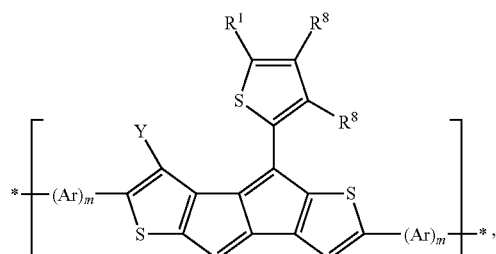

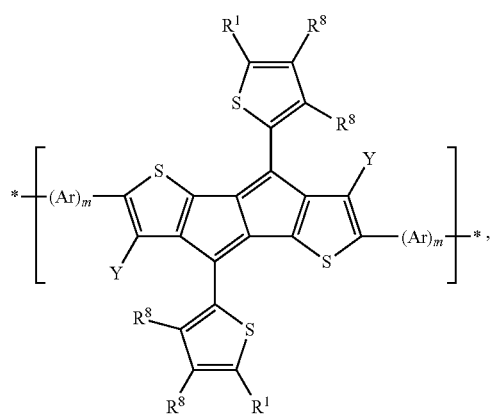

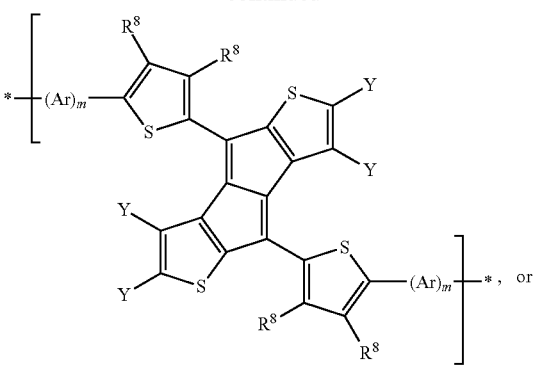

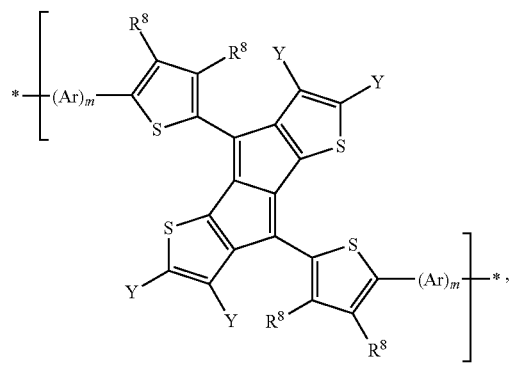

where Y, Ar, $R^1$, $R^8$, and m are as defined herein. Each $R^1$, for example, independently can be selected from H, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group; and each $R^8$, independently can be selected from H, halogen, a $C_{1-40}$ alkyl group, a $C_{2-40}$ alkenyl group, a $C_{2-40}$ alkynyl group, $C_{1-40}$ haloalkyl group, a $C_{1-40}$ alkoxy group, and a $C_{1-40}$ thioalkyl group; and each Y, independently can be selected from H, F, Cl, a linear or branched $C_{1-40}$ alkyl group, a linear or branched $C_{1-40}$ haloalkyl group, a linear or branched $C_{2-40}$ alkenyl group, a linear or branched $C_{2-40}$ alkynyl group, a linear or branched $C_{1-40}$ alkoxy group, and a linear or branched $C_{1-40}$ thioalkyl group.

In particular embodiments, Ar can be a thienyl group optionally substituted with 1-2 functional groups independently selected from the group consisting of F, Cl, —CN, R, —OR, —SR, —C(O)R, —OC(O)R, and —C(O)OR; where R is selected from the group consisting of a $C_{1-40}$ alkyl group, a $C_{1-40}$ haloalkyl group, a $C_{2-40}$ alkenyl group, and a $C_{2-40}$ alkynyl group. Accordingly, particular embodiments of the present polymers can have a repeating unit of the formula:

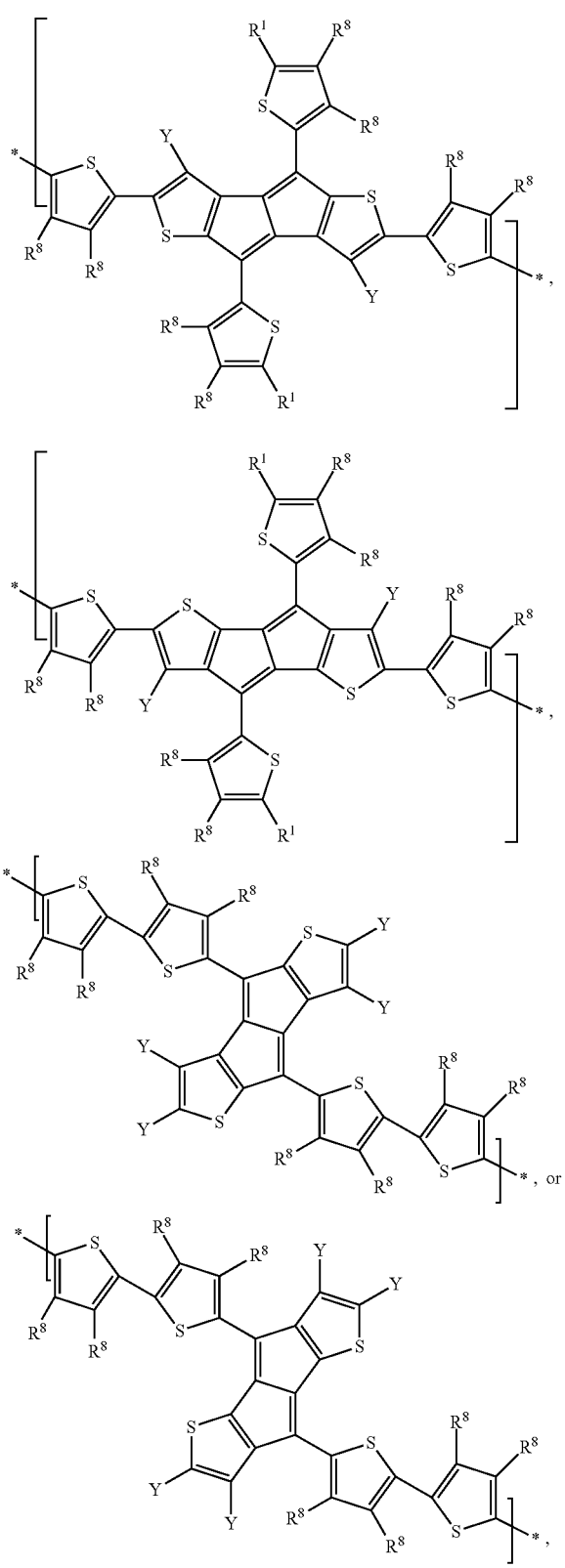

wherein Y, $R^1$ and $R^8$ are as defined herein. For example, in certain embodiments, each of $R^1$ and $R^8$ can be H. In other embodiments, either $R^1$ (if present) or at least one of $R^8$ can be a $C_{1-40}$ alkyl group.

In some embodiments, $Sp^1$ and $Sp^2$ can be $-(Ar)_m-Z-$. Accordingly, certain embodiments of the present polymers can have a repeating unit of the formula:

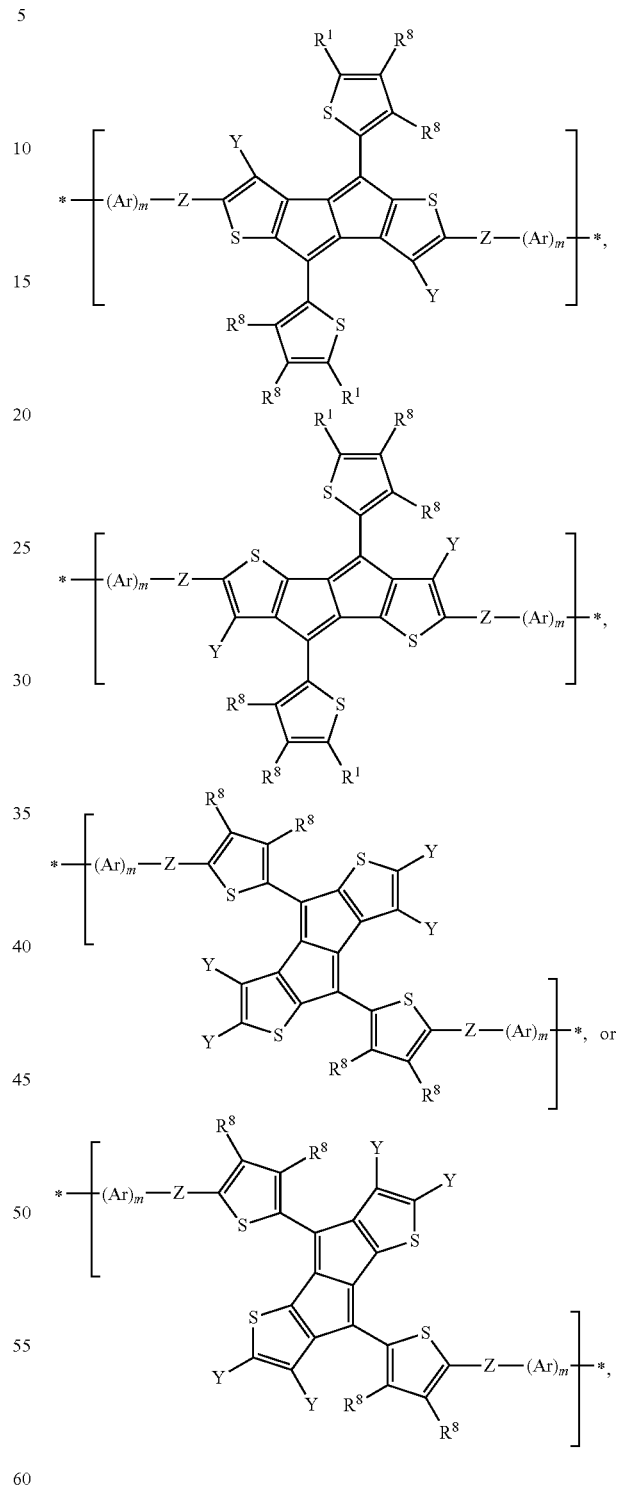

where Ar, Y, Z, $R^1$, $R^8$, and m are as defined herein. For example, Ar can be a thienyl group optionally substituted with 1-2 functional groups independently selected from the group consisting of F, Cl, —CN, R, —OR, —SR, —C(O)R, —OC(O)R, and —C(O)OR; where R is selected from the group consisting of a $C_{1-40}$ alkyl group, a $C_{1-40}$ haloalkyl group, a $C_{2-40}$ alkenyl group, and a $C_{2-40}$ alkynyl group; and Z can be —CR$^9$=CR$^9$—, where each R$^9$ independently can be selected from the group consisting of H, a halogen, CN, a C$_{1-40}$ alkyl group, and a C$_{1-40}$ haloalkyl group.

In certain embodiments, one of Sp$^1$, Sp$^2$, and Sp$^3$ can be —(Ar)$_m$—, while the other two of Sp$^1$, Sp$^2$, and Sp$^3$ are each a covalent bond. In particular embodiments, the spacer group that is not a covalent bond can be an electron-donor unit having the formula:

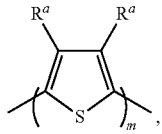

wherein m can be 3, 4 or 5, and R$^a$ is selected from the group consisting of H, F, Cl, —CN, R, —OR, —SR, —C(O)R, —OC(O)R, and —C(O)OR; wherein R is selected from the group consisting of a C$_{1-40}$ alkyl group, a C$_{1-40}$ haloalkyl group, a C$_{2-40}$ alkenyl group, and a C$_{2-40}$ alkynyl group. For example, in certain embodiments, each R$^a$ can be H; while in certain embodiments, at least one of the R$^a$ groups can be F, Cl, —CN, R, —OR, —SR, —C(O)R, —OC(O)R, and —C(O)OR, wherein R is as defined herein.

To illustrate, in certain embodiments, the electron-donating spacer group can comprise a terthiophene, where optionally the terthiophene can be selected from the group consisting of:

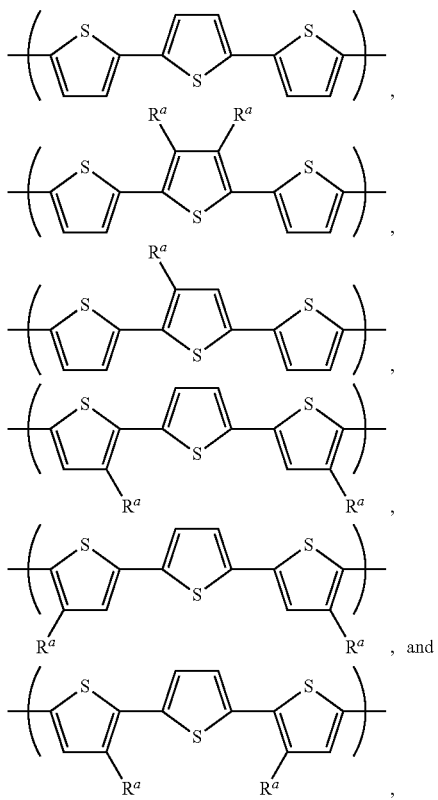

wherein R$^a$, at each occurrence, independently can be selected from the group consisting of a -L-C$_{6-40}$ alkyl group, a -L-C$_{6-40}$ alkenyl group, and a -L-C$_{6-40}$ haloalkyl group, wherein L, at each occurrence, can be selected from the group consisting of O, S, and a covalent bond.

In other embodiments, the electron-donating spacer group can comprise a quaterthiophene, where optionally the quaterthiophene can be selected from the group consisting of:

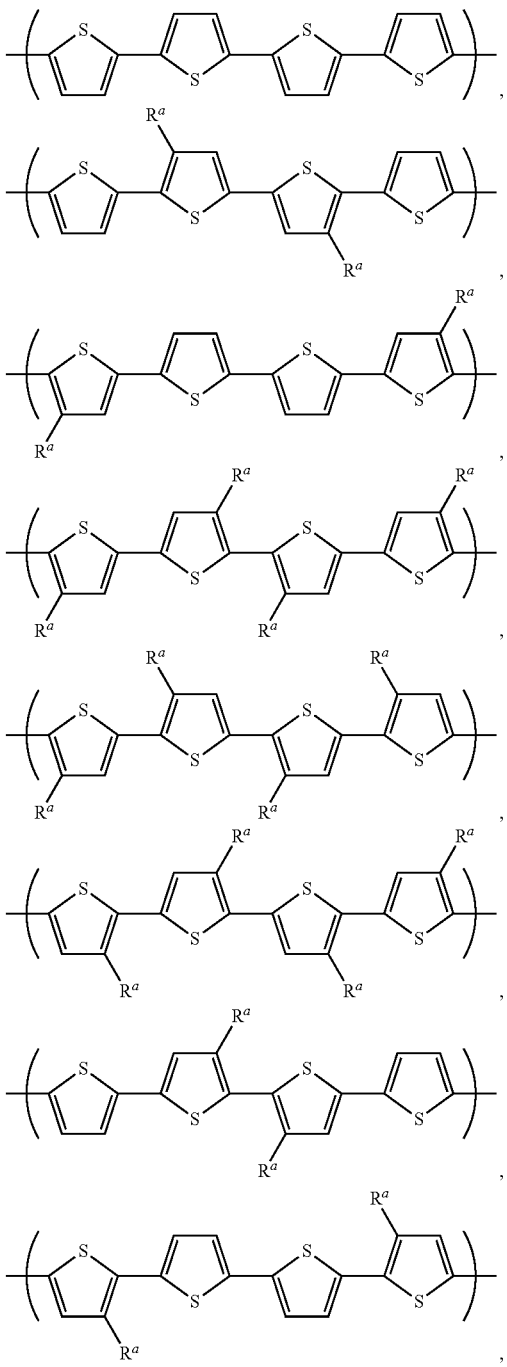

wherein R$^a$, at each occurrence, independently can be selected from the group consisting of a -L-C$_{6-40}$ alkyl group, a -L-C$_{6-40}$ alkenyl group, and a -L-C$_{6-40}$ haloalkyl group, wherein L, at each occurrence, can be selected from the group consisting of O, S, and a covalent bond.

In various embodiments of the present polymers, pi-2 can be a covalent bond. Accordingly, certain embodiments of the present polymers can be represented by a formula selected from the group consisting of:

$$\text{―}[(Ar)_{\overline{m}}\text{―}\boxed{pi\text{-}1}\text{―}(Ar)_{\overline{m}}]_{\overline{n}}\text{―},\qquad (\text{III-a})$$

$$\text{―}[(Ar)_{\overline{m}}\text{―}Z\text{―}\boxed{pi\text{-}1}\text{―}Z\text{―}(Ar)_{\overline{m}}]_{\overline{n}}\text{―},\text{ and}\qquad (\text{III-b})$$

$$\text{―}[\boxed{pi\text{-}1}\text{―}(Ar)_{\overline{m}}]_{\overline{n}}\text{―},\qquad (\text{III-c})$$

where Ar, Z, and m are as defined herein. The degree of polymerization (n) can be an integer in the range of 2 to 10,000, for example, in the range of 3 and 5,000, preferably between 5 and 5,000, and more preferably, between 10 and 5,000. For example, particular embodiments of the present polymers can have a formula selected from the group consisting of:

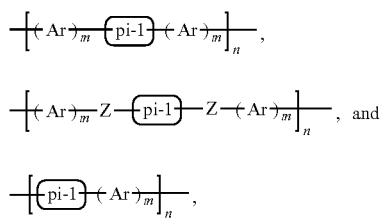

and

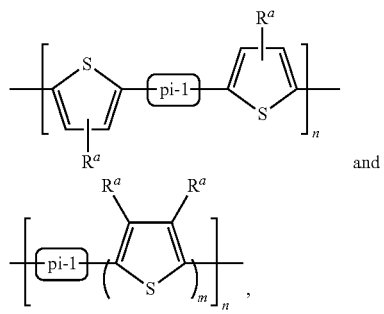

where each $R^a$ independently is selected from the group consisting of H, F, Cl, —CN, R, —OR, —SR, —C(O)R, —OC(O)R, and —C(O)OR; wherein R is selected from the group consisting of a $C_{1\text{-}40}$ alkyl group, a $C_{1\text{-}40}$ haloalkyl group, a $C_{2\text{-}40}$ alkenyl group, and a $C_{2\text{-}40}$ alkynyl group; m is 3, 4 or 5; and n is an integer in the range of 3 and 5,000.

Other embodiments of the present polymers can include one or more pi-2 moieties, where each pi-2 is an optionally substituted conjugated polycyclic moiety that is different from pi-1. For example, each pi-2 independently can be a conjugated polycyclic moiety selected from the group consisting of:

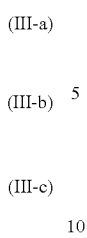

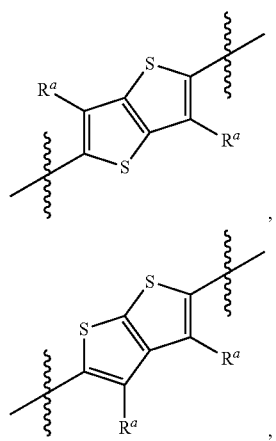

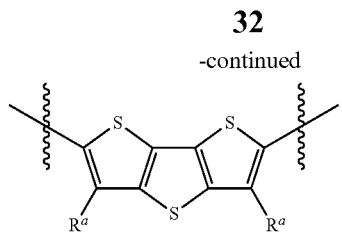

,

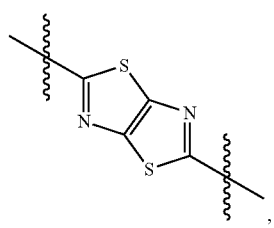

,

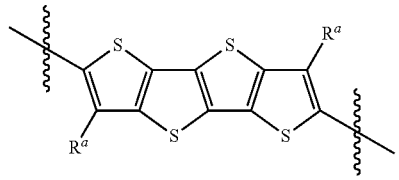

,

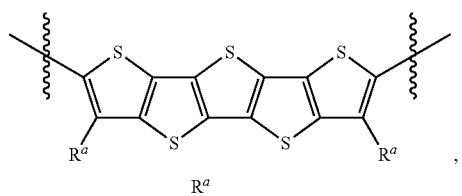

,

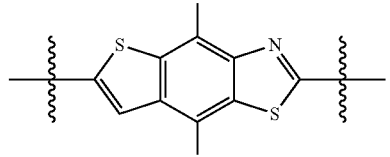

,

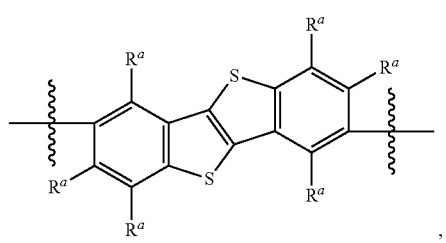

,

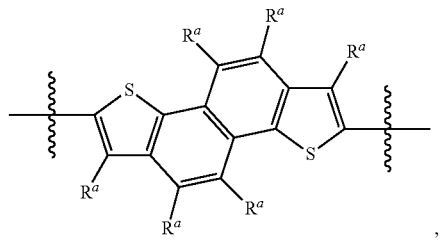

,

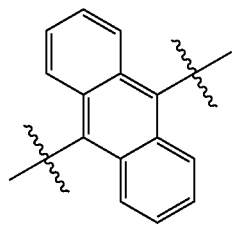

,

33
-continued
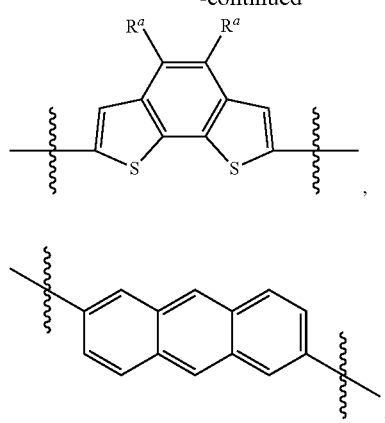
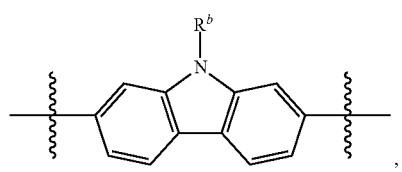
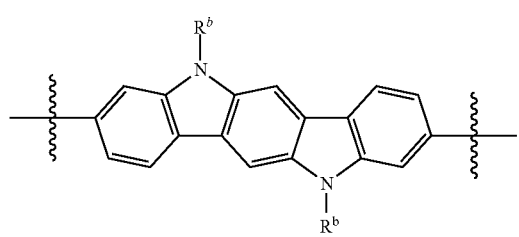
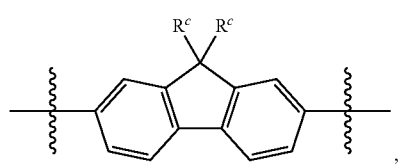
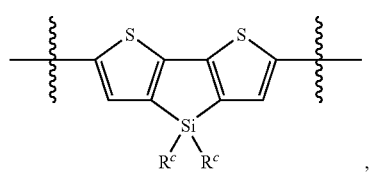
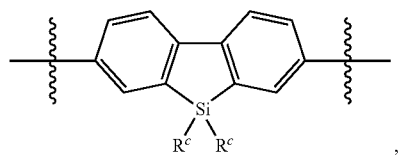
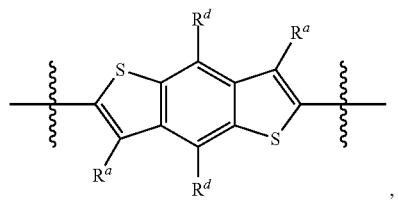
34
-continued
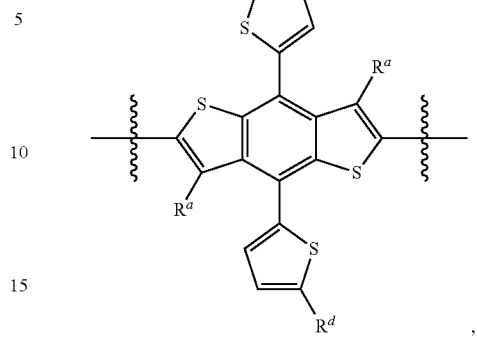
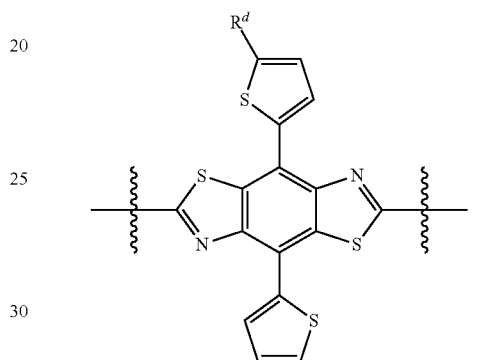
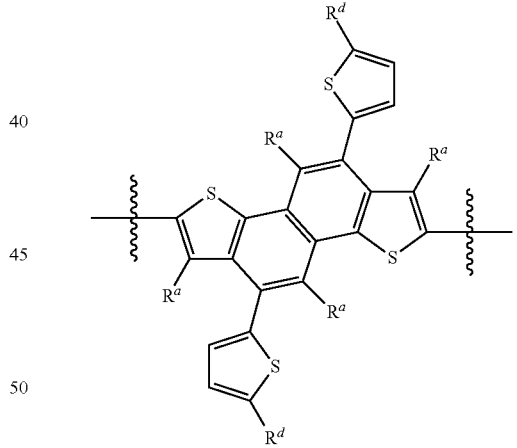
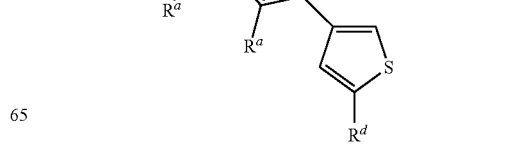

-continued
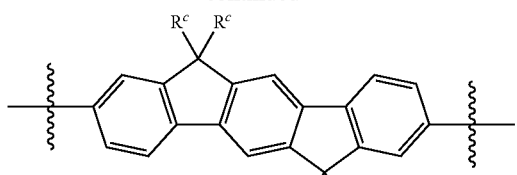
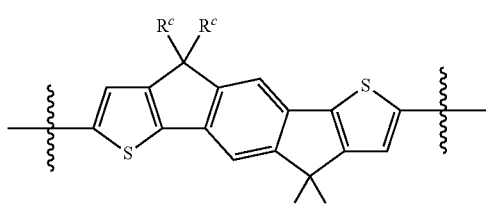
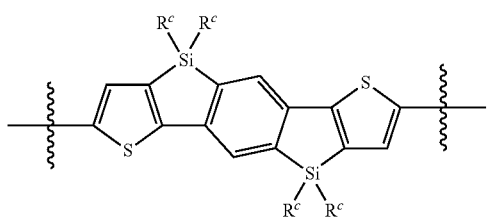
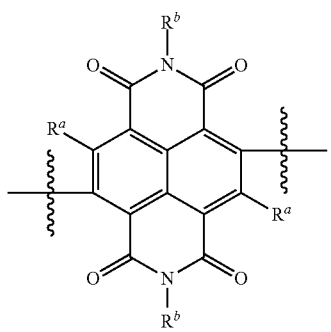
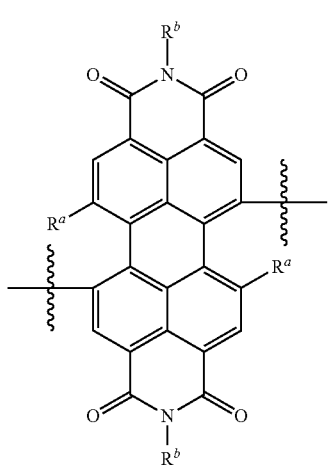
-continued
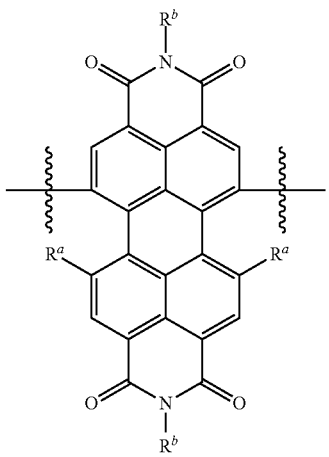
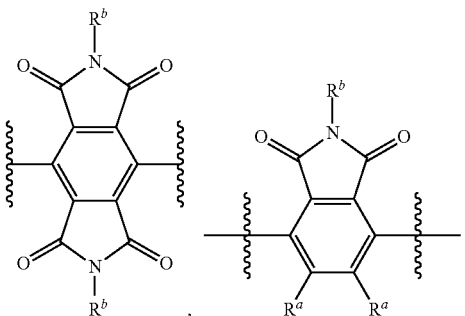
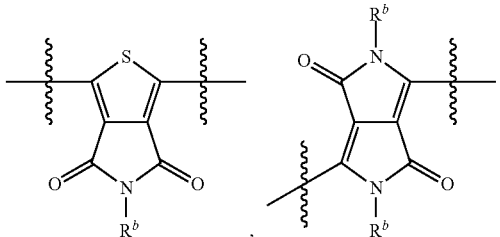
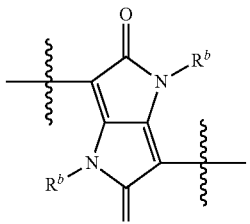
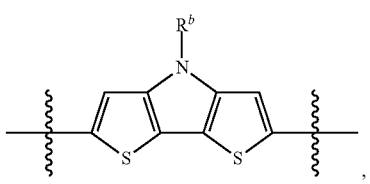

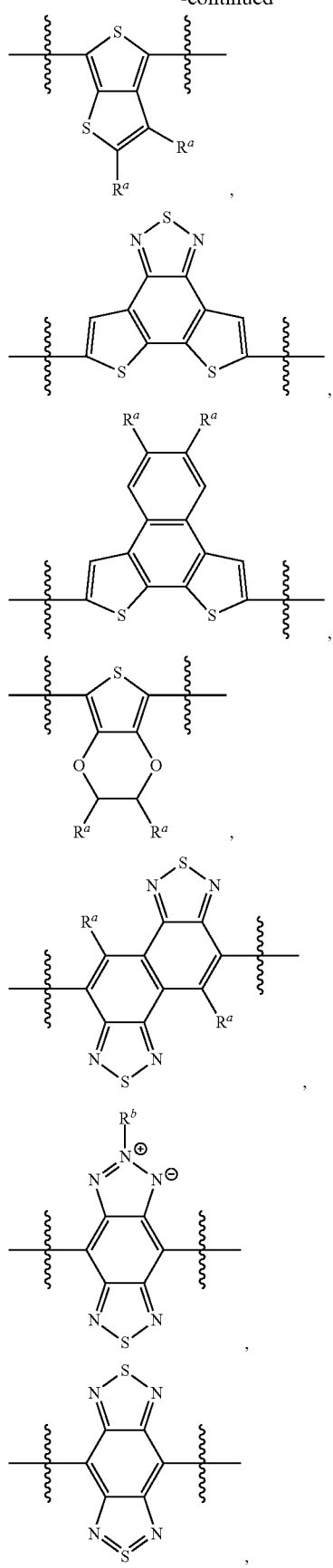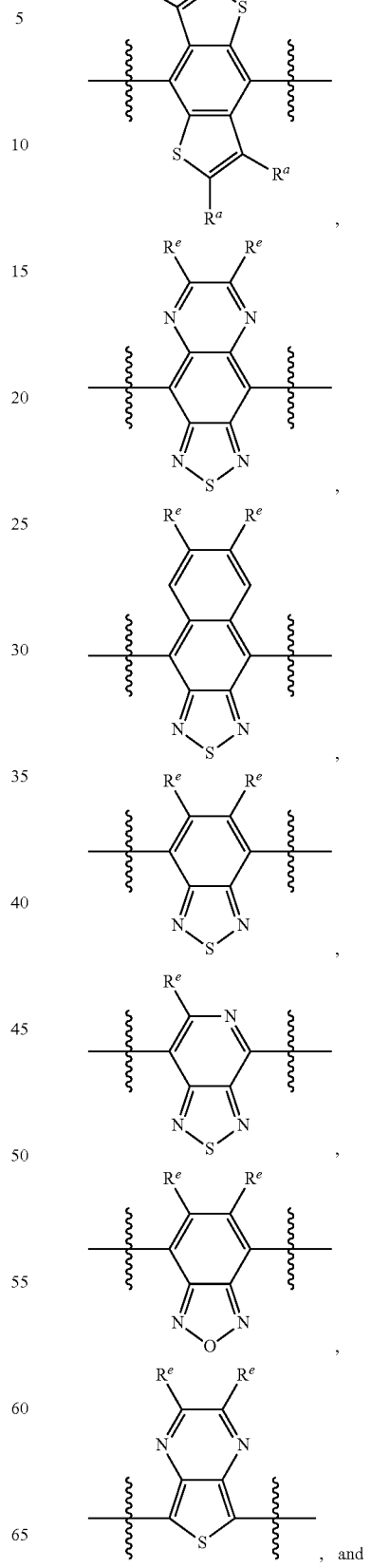

-continued

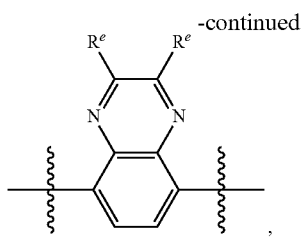

wherein:

- $R^a$ is selected from the group consisting of H, F, Cl, —CN, R, —OR, —SR, —C(O)R, —OC(O)R, and —C(O)OR;
- $R^b$ is selected from the group consisting of H, R, and -L-$R^f$;
- $R^c$ is H or R;
- $R^d$ is selected from the group consisting of H, F, Cl, —CN, R, —OR, —SR, —C(O)R, —OC(O)R, —C(O)OR, and -L-$R^f$;
- $R^e$ is selected from the group consisting of H, F, Cl, —CN, R, —OR, —SR, —C(O)R, —OC(O)R, —C(O)OR, and $R^f$;
- $R^f$ is a $C_{6-20}$ aryl group or a 5-20-membered heteroaryl group, each optionally substituted with 1-8 groups independently selected from the group consisting of F, Cl, —CN, R, —OR, and —SR;
- L is selected from the group consisting of —O—, —S—, —C(O)—, —OC(O)—, —C(O)—O, and a covalent bond; and
- R is selected from the group consisting of a $C_{1-40}$ alkyl group, a $C_{1-40}$ haloalkyl group, a $C_{2-40}$ alkenyl group, and a $C_{2-40}$ alkynyl group.

Embodiments of the present polymers including a pi-2 moiety can be obtained by copolymerization of a first building block including pi-1 and a second building block including pi-2. The second building block including pi-2 can include conjugated spacer groups $Sp^2$ and/or $Sp^3$. For example, certain embodiments of the present polymers can have a formula selected from the group consisting of:

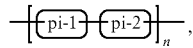 (III-d)

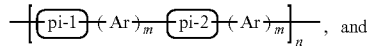, and (III-e)

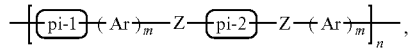, (III-f)

where pi-1, pi-2, Ar, Z, and m are as defined herein. The degree of polymerization (n) can be an integer in the range of 2 to 10,000, for example, in the range of 3 and 5,000, preferably between 5 and 5,000, and more preferably, between 10 and 5,000. For example, particular embodiments of the present polymers can have a formula selected from the group consisting of:

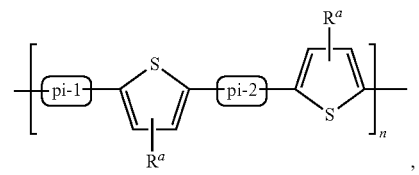

wherein:

- $R^a$ is selected from the group consisting of H, F, Cl, —CN, R, —OR, —SR, —C(O)R, —OC(O)R, and —C(O)OR, where R is selected from the group consisting of a $C_{1-40}$ alkyl group, a $C_{1-40}$ haloalkyl group, a $C_{2-40}$ alkenyl group, and a $C_{2-40}$ alkynyl group;
- pi-1 is selected from the group consisting of:

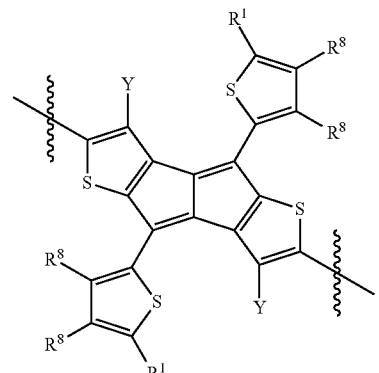

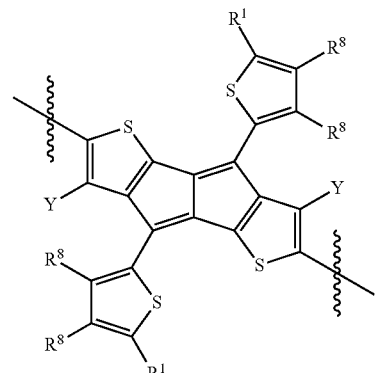

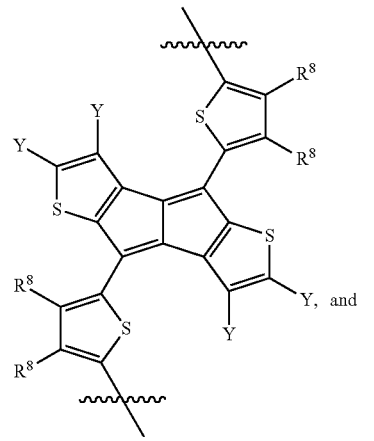

and

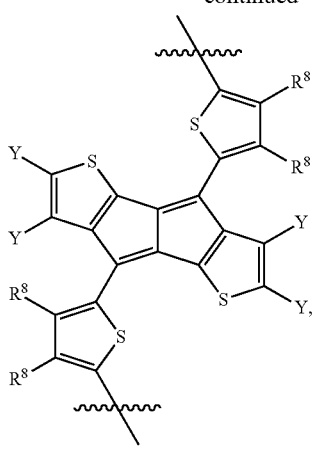
where R¹ and R⁸ can be H or a $C_{1-40}$ alkyl group, and Y is as defined herein;
pi-2 is selected from the group consisting of:
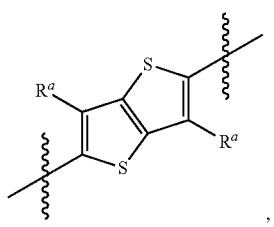
,
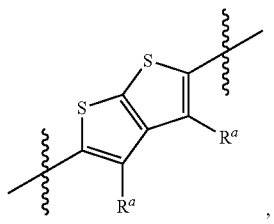
,
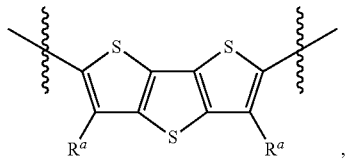
,
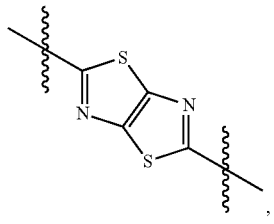
,
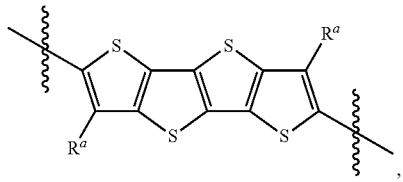
,
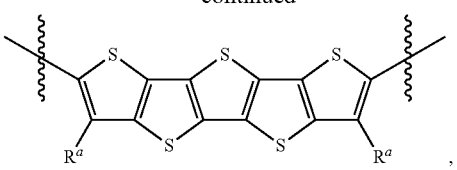
,
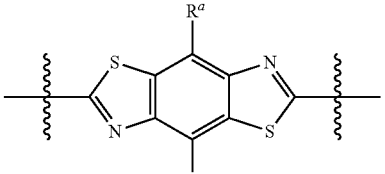
,
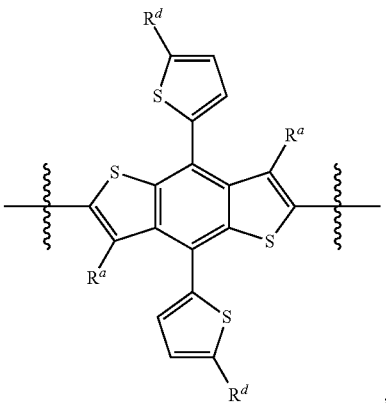
,
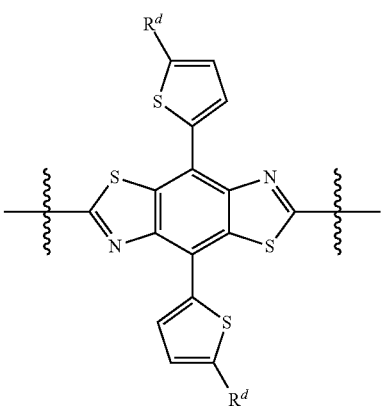
,
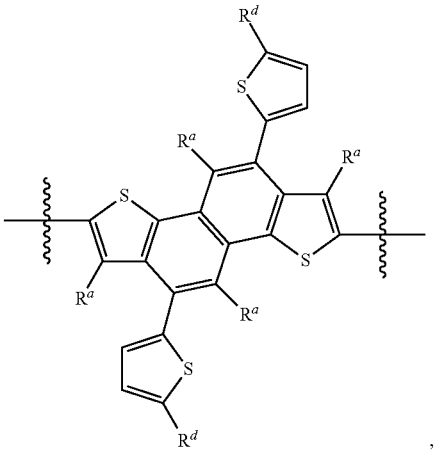
, -continued
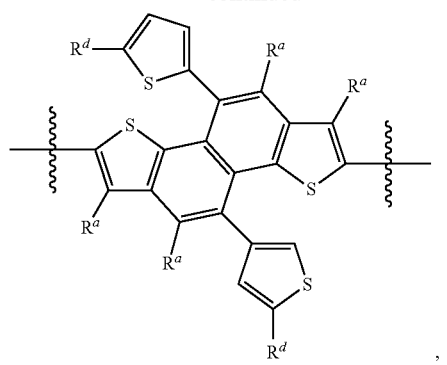
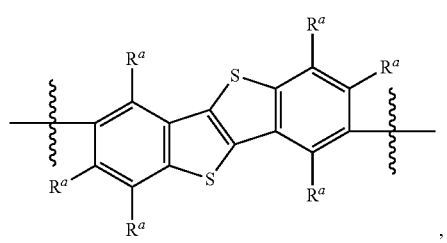
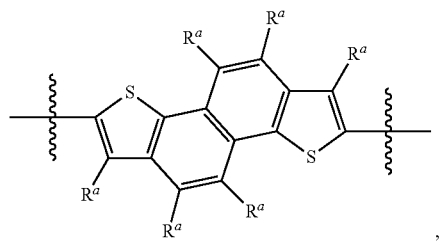
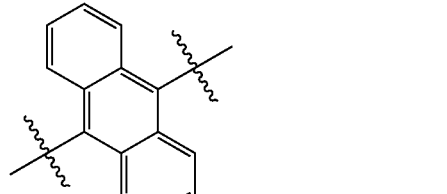
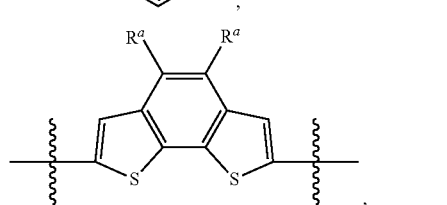
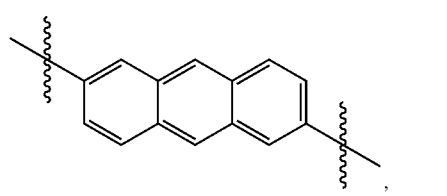
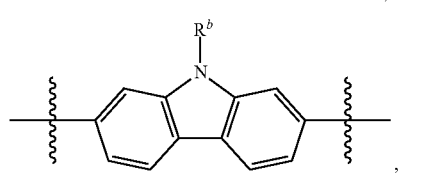
-continued
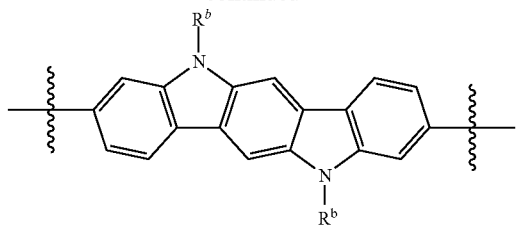
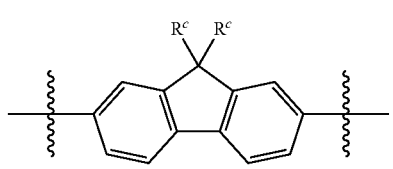
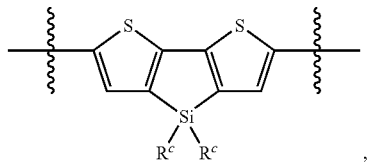
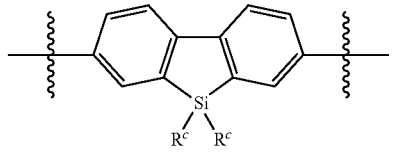
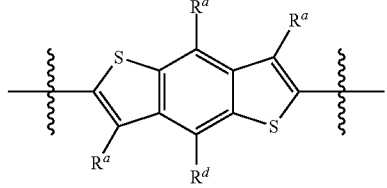
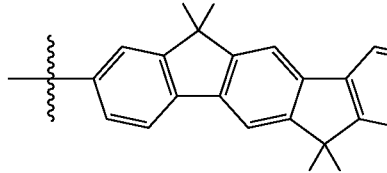
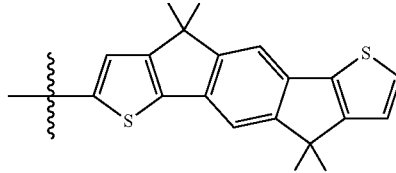
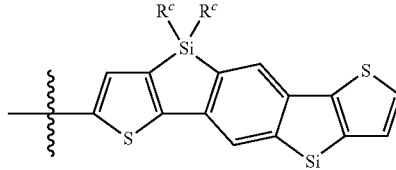

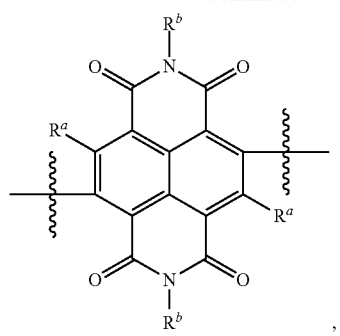
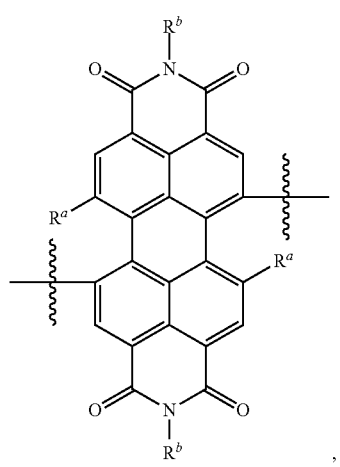
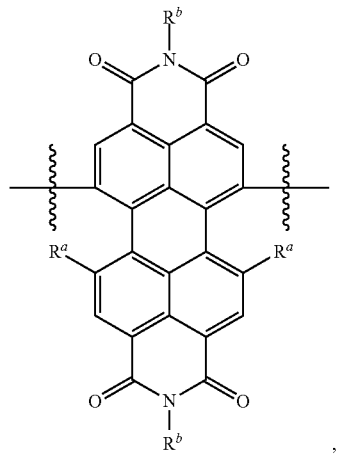
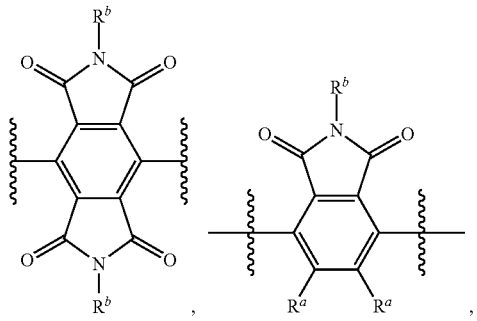
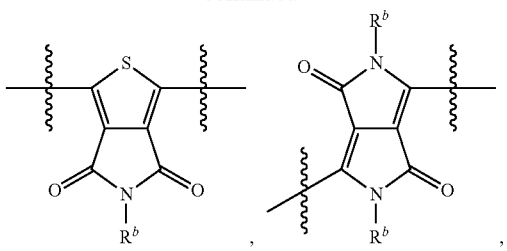
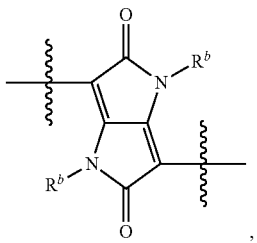
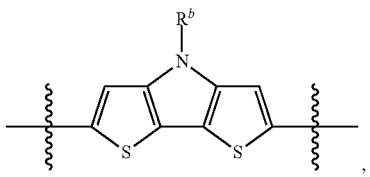
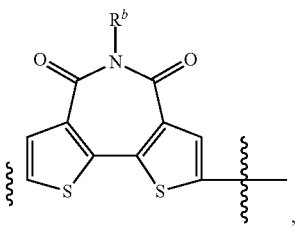
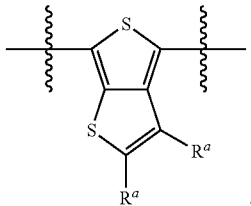
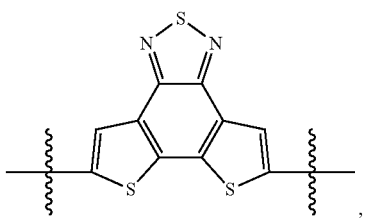
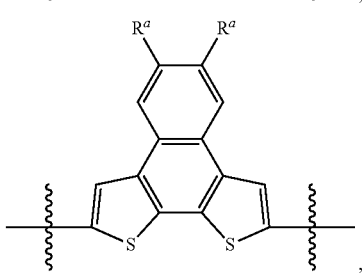

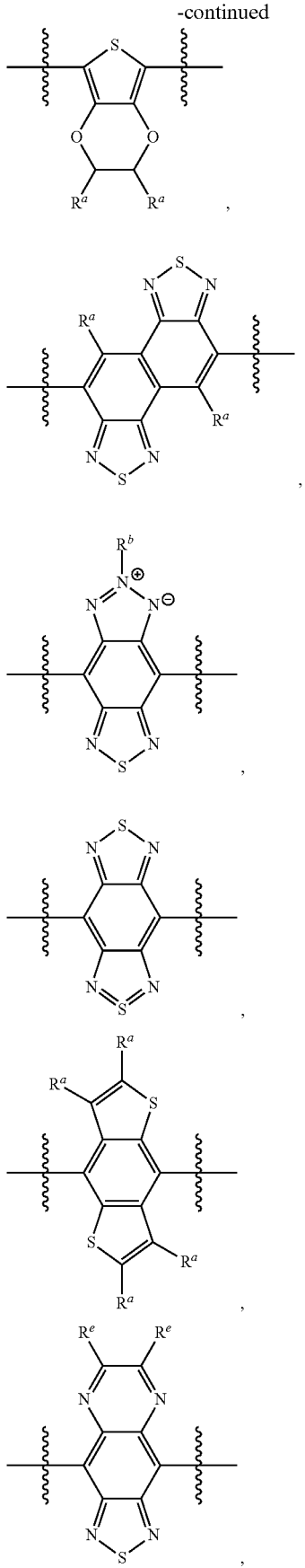

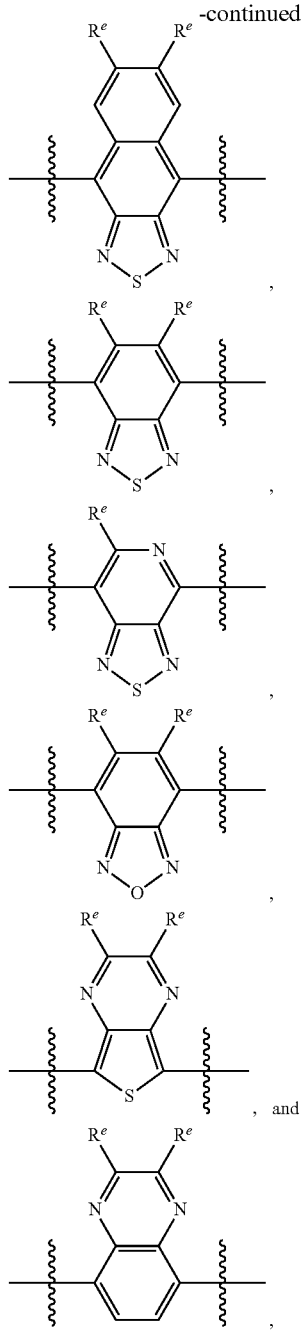

wherein:

R$^a$ is selected from the group consisting of H, F, Cl, —CN, R, —OR, —SR, —C(O)R, —OC(O)R, and —C(O)OR;

R$^b$ is selected from the group consisting of H, R, and -L-R$^f$;

R$^e$ is H or R;

R$^d$ is selected from the group consisting of H, F, Cl, —CN, R, —OR, —SR, —C(O)R, —OC(O)R, —C(O)OR, and -L-R$^f$;

R$^e$ is selected from the group consisting of H, F, Cl, —CN, R, —OR, —SR, —C(O)R, —OC(O)R, —C(O)OR, and R$^f$;

R$^f$ is a C$_{6-20}$ aryl group or a 5-20-membered heteroaryl group, each optionally substituted with 1-8 groups independently selected from the group consisting of F, Cl, —CN, R, —OR, and —SR;

L is selected from the group consisting of —O—, —S—, —C(O)—, —OC(O)—, —C(O)O—, and a covalent bond; and R is selected from the group consisting of a $C_{1-40}$ alkyl group, a $C_{1-40}$ haloalkyl group, a $C_{2-40}$ alkenyl group, and a $C_{2-40}$ alkynyl group; and n is an integer in the range of 3 and 5,000.

Without limitation, exemplary embodiments of the present polymers can have a repeating unit selected from the group consisting of:

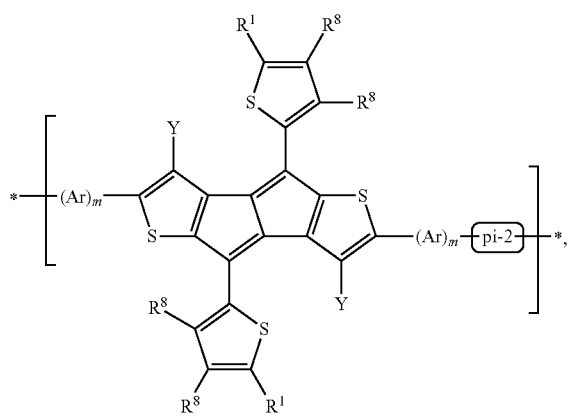

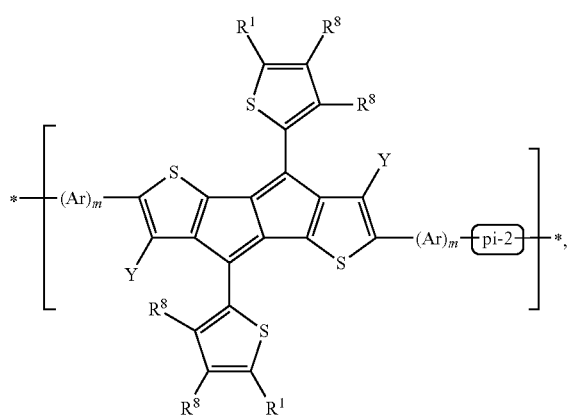

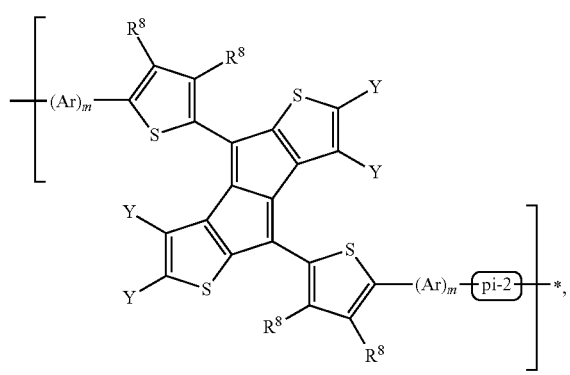

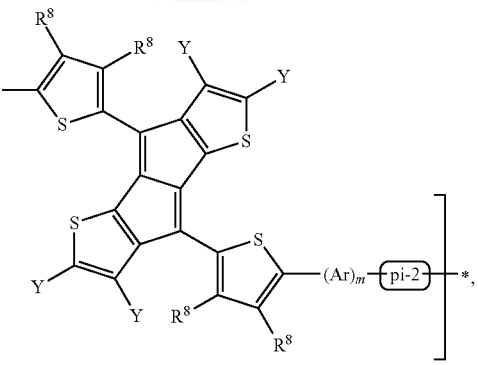

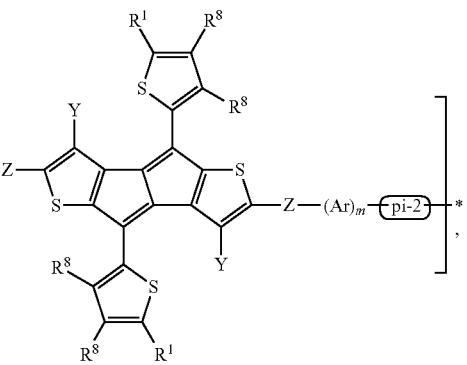

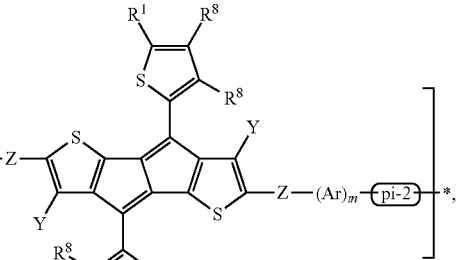

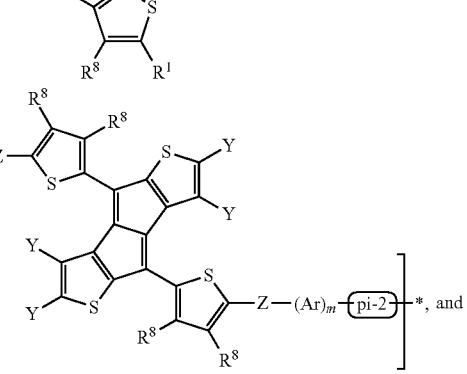

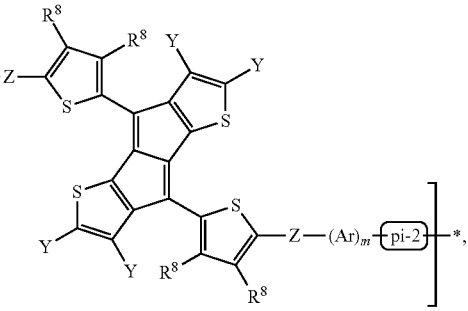

where Ar, Y, Z, pi-2, $R^1$, $R^8$, and m are as defined herein.

In certain embodiments, the present polymers can be represented by formula (III):

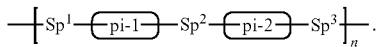 (III)

In other embodiments, in addition to the repeating unit:

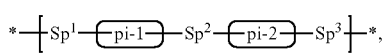 (M₁)

the present polymers can include a second repeating unit M₂ which is different from the first repeating unit M₁ and has the formula:

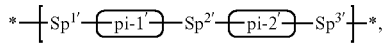 (M₂)

wherein:
pi-1' has the formula:

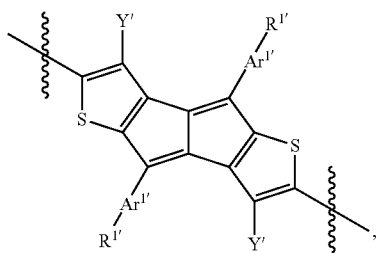

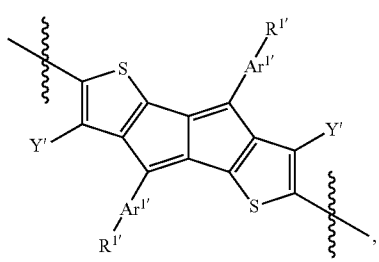

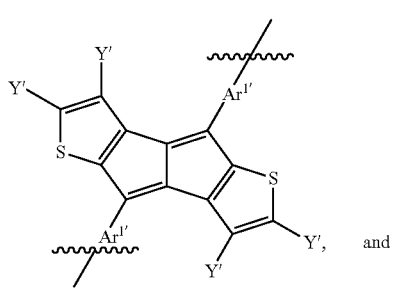

-continued

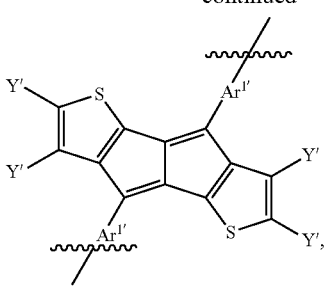

wherein:

Y', at each occurrence, independently is selected from halogen, R¹', and —(Ar¹)$_{p'}$—R¹';

Ar¹', at each occurrence, independently is an optionally substituted divalent C$_{6-20}$ aryl or 5-20 membered heteroaryl group; and R¹', at each occurrence, independently is selected from H, —C(O)OR⁴, —C(O)R⁴, —Si(R⁵)₃, a C$_{1-40}$ alkyl group, a C$_{3-40}$ alkenyl group, a C$_{3-40}$ alkynyl group, C$_{1-40}$ haloalkyl group, a C$_{1-40}$ alkoxy group, and a C$_{1-40}$ thioalkyl group;

wherein R⁴ is H or a C$_{1-6}$ alkyl group; and R⁵ is a C$_{1-6}$ alkyl group; and p' is 1, 2, 3 or 4;

pi-2' is a covalent bond or an optionally substituted conjugated polycyclic moiety that is different from pi-1'; and each of sp¹', Sp²', and Sp³' independently is a covalent bond or a conjugated spacer group having a formula selected from the group consisting of:

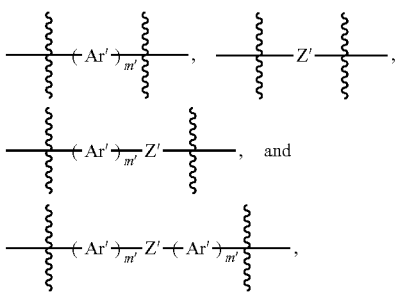

wherein each Ar' independently is an optionally substituted conjugated monocyclic moiety; Z' is a conjugated linear linker; and m' is 1, 2, 3 or 4; and provided the second repeating unit is different from the first repeating unit.

For example, the second repeating unit can have a formula selected from the group consisting of:

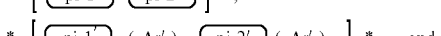
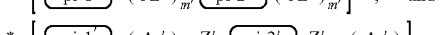

wherein:
pi-1' is selected from:

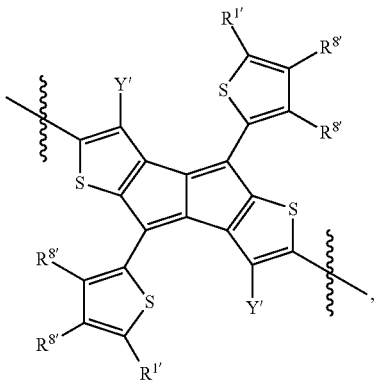

,

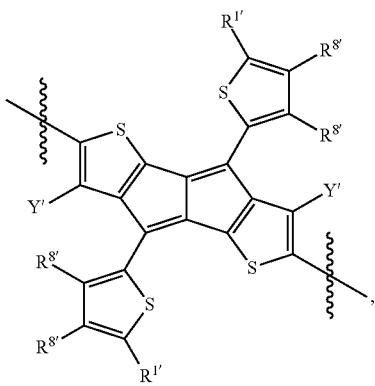

,

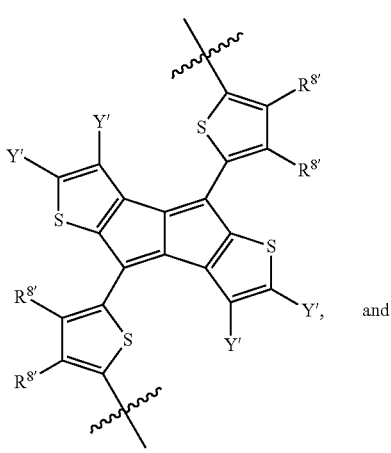

and

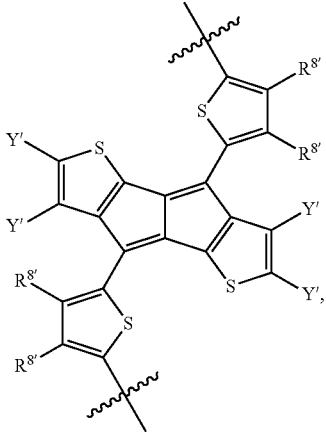

, wherein:

Y', at each occurrence, independently is selected from H, halogen, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group;

$R^{1'}$, at each occurrence, independently is selected from H, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group; and $R^{8'}$, at each occurrence, independently is H or $R^7$; wherein $R^7$, at each occurrence, independently is selected from halogen, a $C_{1-40}$ alkyl group, a $C_{2-40}$ alkenyl group, a $C_{2-40}$ alkynyl group, $C_{1-40}$ haloalkyl group, a $C_{1-40}$ alkoxy group, and a $C_{1-40}$ thioalkyl group;

pi-2' is an optionally substituted conjugated polycyclic moiety that is different from π-1;

each Ar' independently is an optionally substituted conjugated monocyclic moiety;

Z' is a conjugated linear linker; and m' is 1, 2, 3 or 4.

The first repeating unit and the second repeating unit can be arranged in an alternating manner or a random manner, and the resulting polymer can be represented by formula (IV):

(IV)

where x and y are real numbers representing mole fractions, wherein $0.05 \leq x \leq 0.95$, $0.05 \leq y \leq 0.95$, and the sum of x and y is about 1; and the degree of polymerization (n) can be an integer in the range of 2 to 10,000. For example, n can be in the range of 3 and 5,000, preferably between 5 and 5,000, and more preferably, between 10 and 5,000.

In preferred embodiments, pi-1 and pi-1' can be the same, and the present polymer can be a random copolymer provided by copolymerization of pi-1 with two different building blocks each including an optionally substituted conjugated polycyclic moiety that is different from pi-1.

To illustrate, random copolymers according to the present teachings can have a formula selected from the group consisting of:

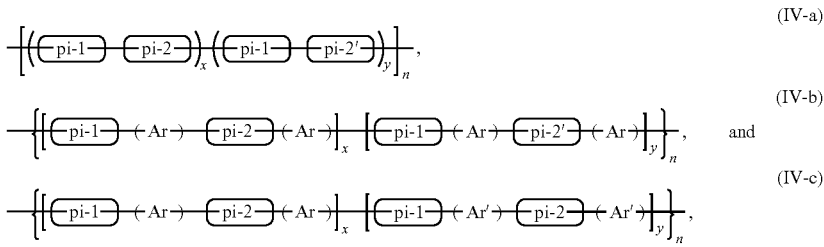

where pi-2' is different from pi-2, Ar' is different from Ar, x and y are real numbers representing mole fractions, wherein $0.05 \leq x \leq 0.95$, $0.05 \leq y \leq 0.95$, and the sum of x and y is about 1.

For example, random polymers according to the present teachings can have a formula selected from the group consisting of:

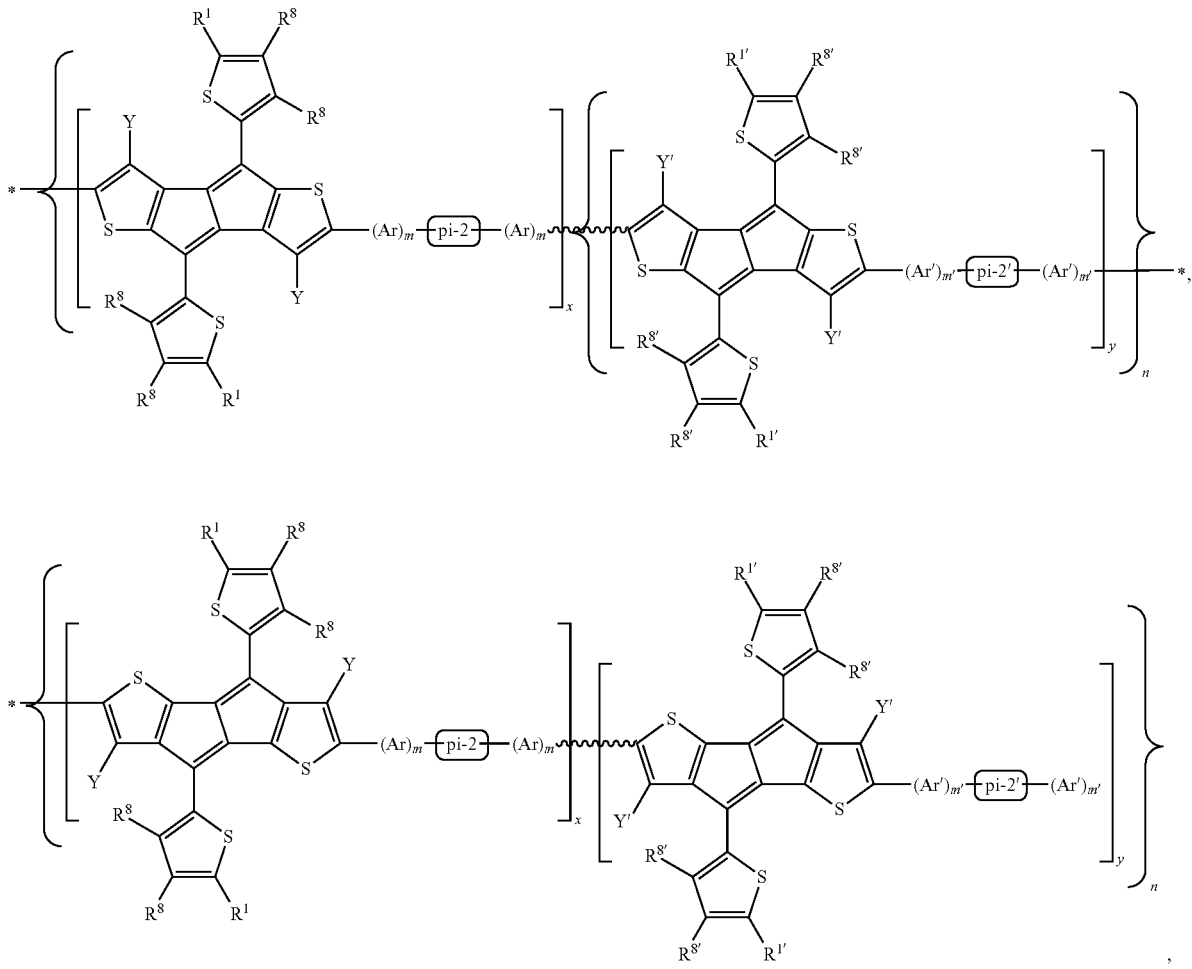

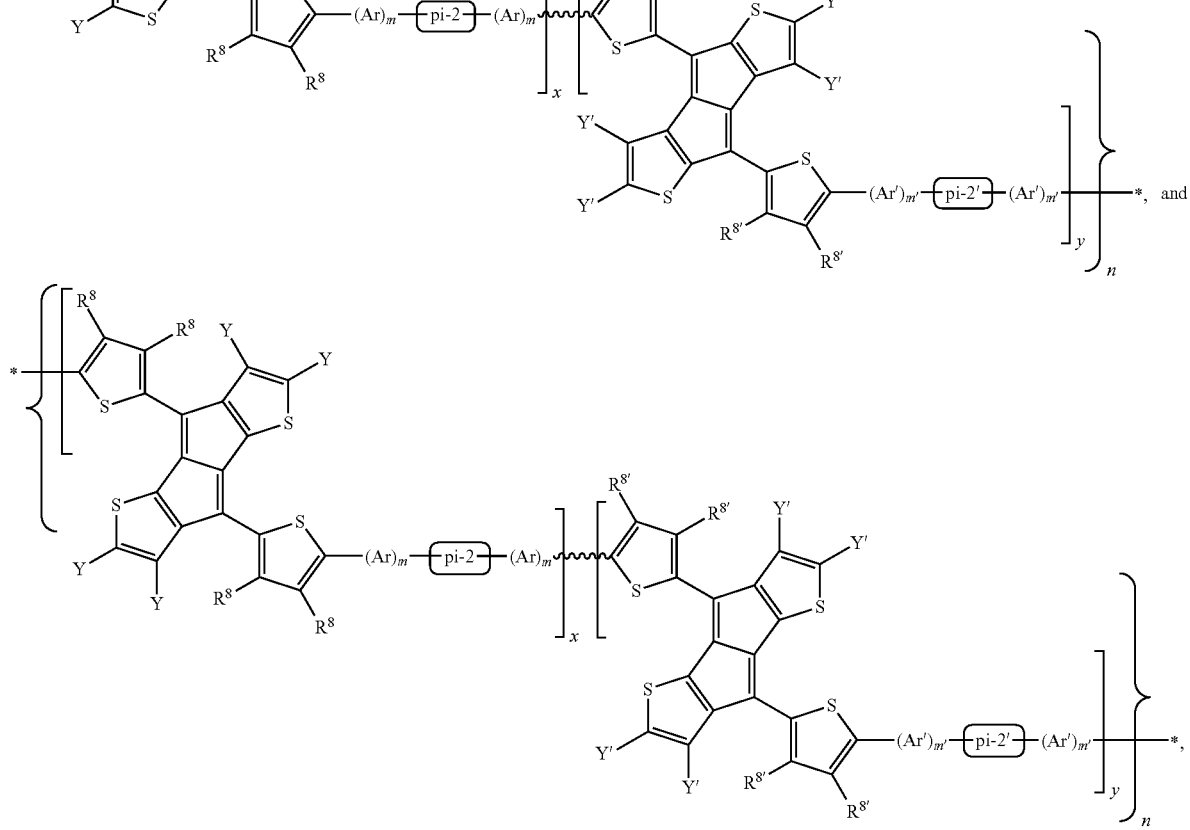

wherein n is an integer in the range of 2 to 10,000; x and y are real numbers representing mole fractions, wherein $0.05 \leq x \leq 0.95$, $0.05 \leq y \leq 0.95$, and the sum of x and y is about 1; and provided Ar is different from Ar', or pi-2 is different from pi-2'.

In preferred embodiments, Ar and Ar' are different. For example, each Ar can be an unsubstituted thienyl group, while each Ar' can be a thienyl group having at least one substitution group selected from R, OR, and SR, where R is selected from the group consisting of a $C_{1-40}$ alkyl group, a $C_{1-40}$ haloalkyl group, a $C_{2-40}$ alkenyl group, and a $C_{2-40}$ alkynyl group.

The present compounds can be prepared from commercially available starting materials, compounds known in the literature, or via other readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (NMR, e.g., $^1$H or $^{13}$C), infrared spectroscopy (IR), optical absorption/emission spectroscopy (e.g., UV-visible), mass spectrometry (MS), or by chromatography such as high pressure liquid chromatography (HPLC), gas chromatography (GC), gel-permeation chromatography (GPC), or thin layer chromatography (TLC).

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

Schemes 1-19 below provide possible synthetic routes for preparing various compounds according to the present teachings. Particularly, compounds of formula (I) and formula (II) where X and Y are H and Z is —C(O)—, i.e., Compound 1

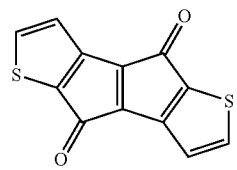

and

Compound 2 can be used as a starting compound for preparing other compounds of formula (I) and formula (II), respectively.

Accordingly, one aspect of the present teachings is directed to methods of preparing Compound 1 and Compound 2. For example, Compound 1 can be synthesized using one of the synthetic routes illustrated in Schemes 1-6:

Scheme 1

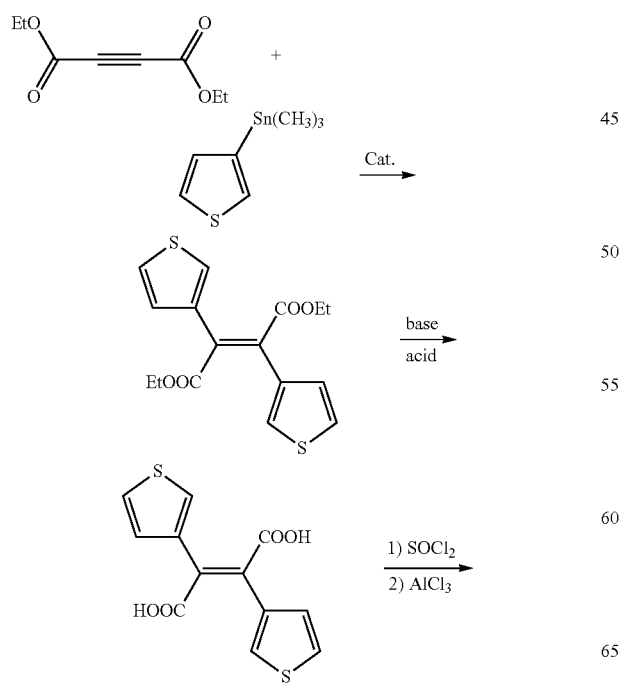

Scheme 2

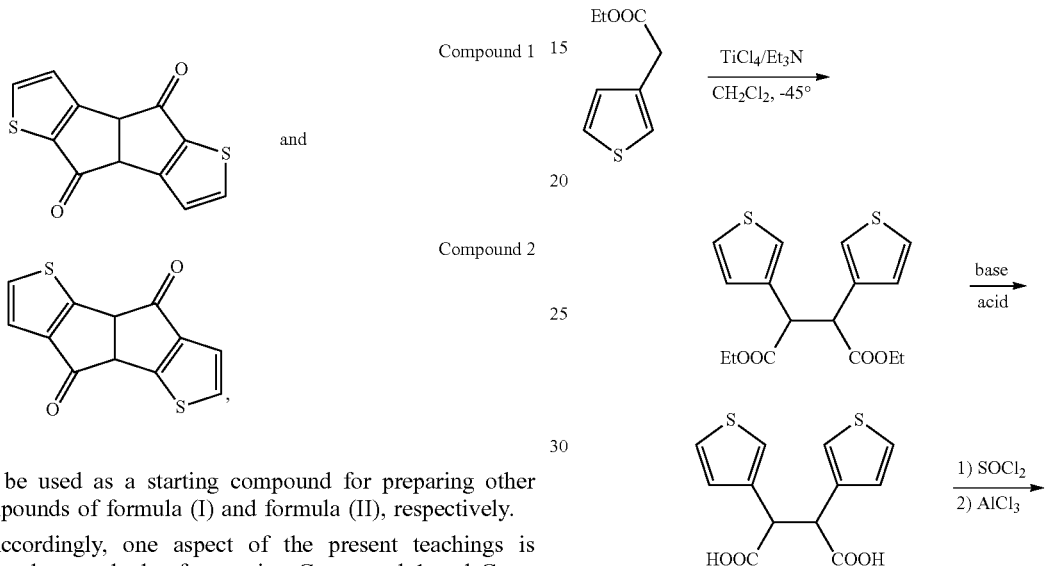

Scheme 3

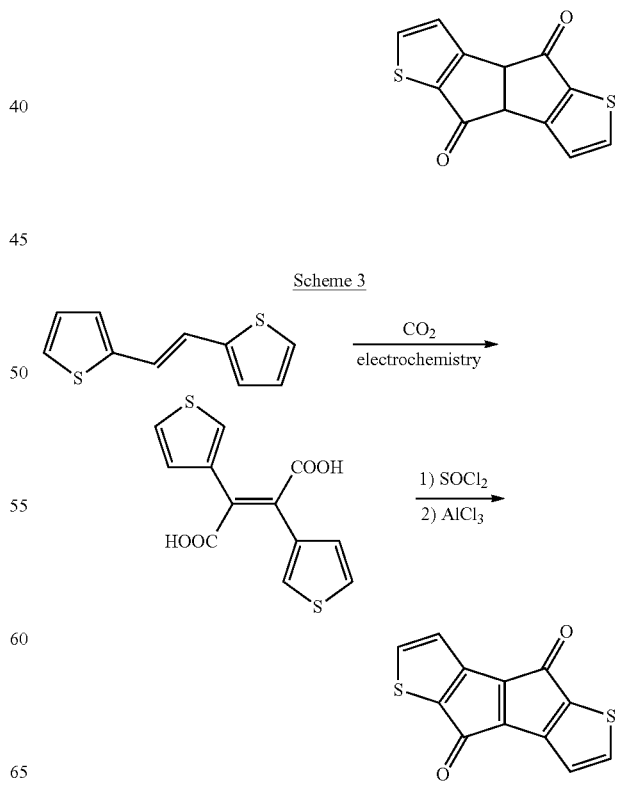

Scheme 4
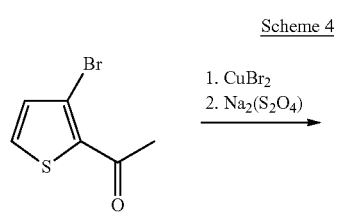
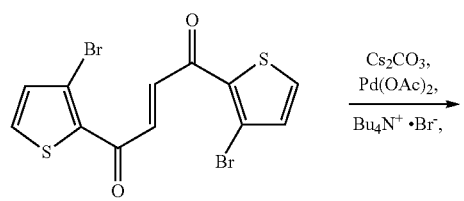
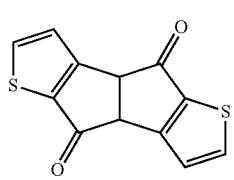
Scheme 5
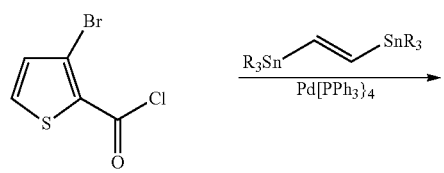
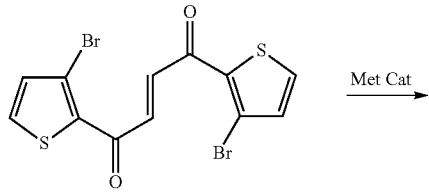
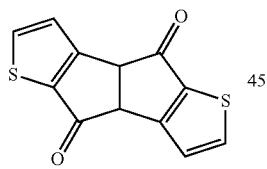
Scheme 6
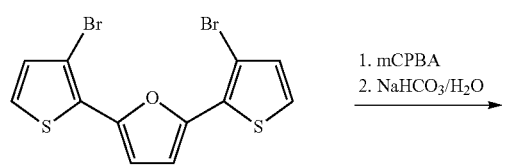
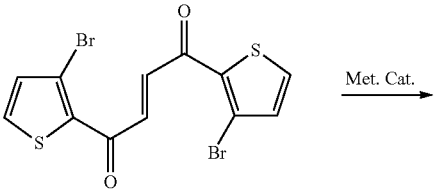
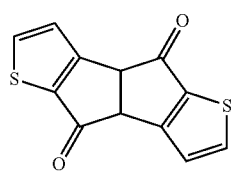
Compound 2 can be synthesized analogously, for example, using the synthetic routes illustrated in Schemes 7-9:
Scheme 7
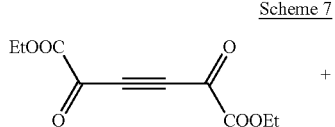
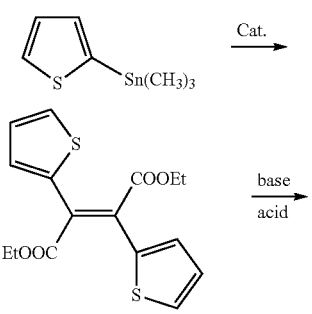
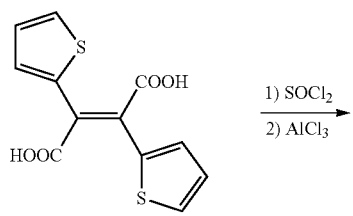
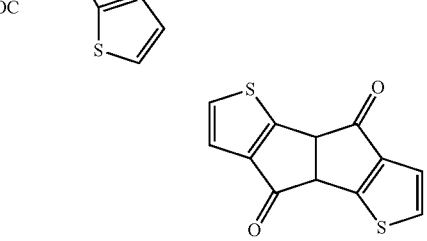
Scheme 8
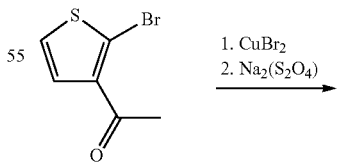
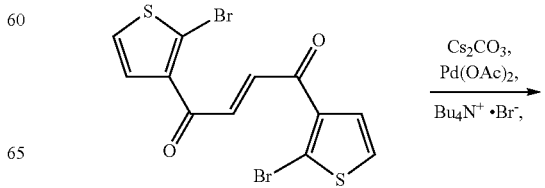

-continued
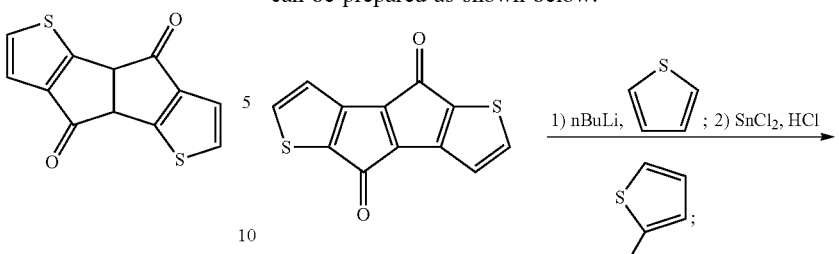
Scheme 9
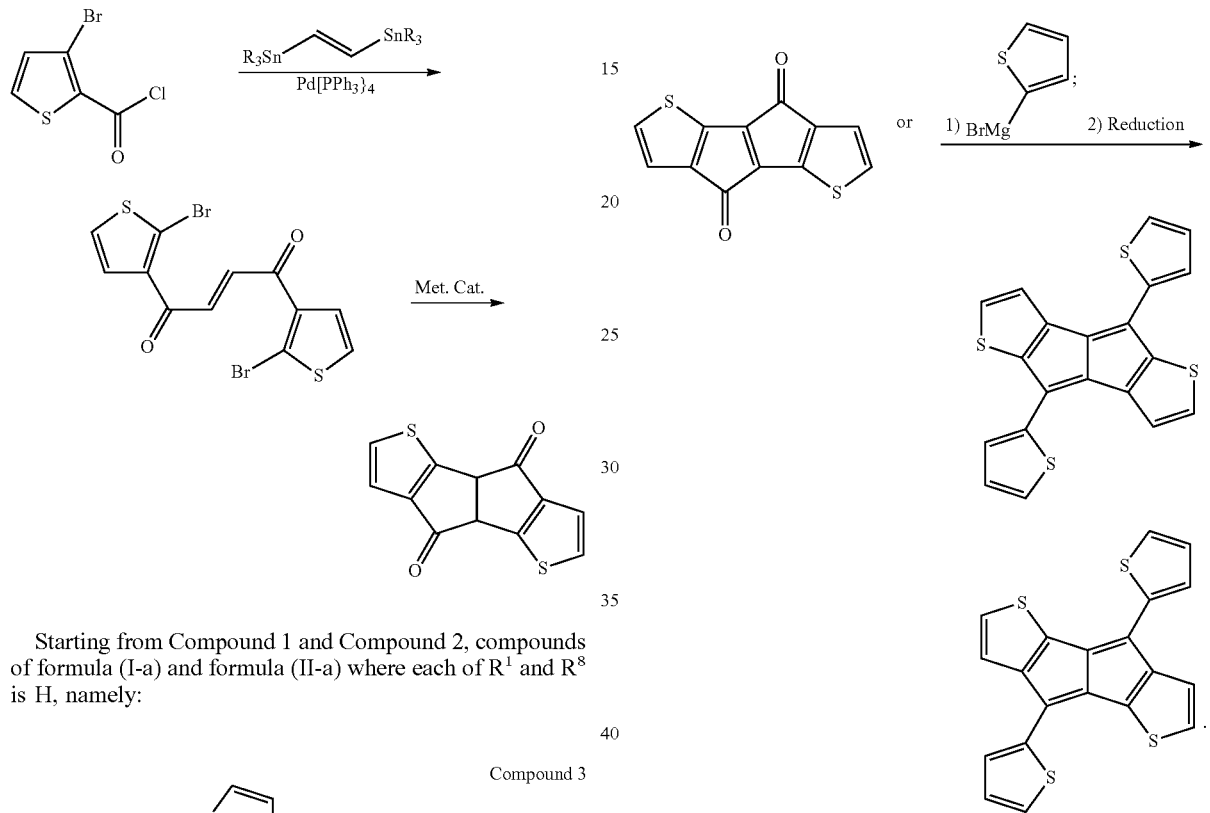
Starting from Compound 1 and Compound 2, compounds of formula (I-a) and formula (II-a) where each of $R^1$ and $R^8$ is H, namely:
Compound 3
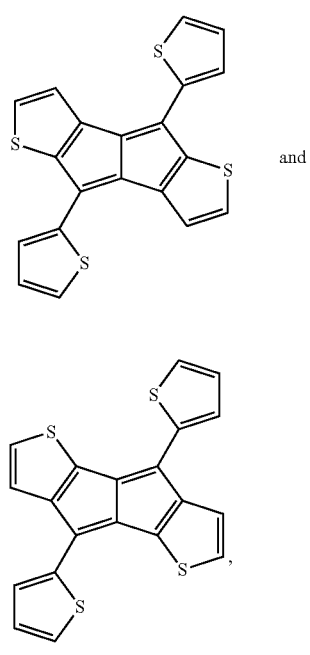
and
Compound 4
can be prepared as shown below:
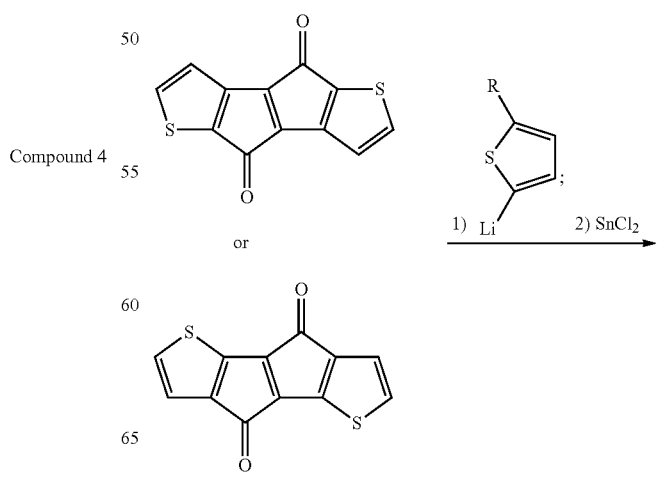
Additional compounds of formula (I-a) and formula (II-a) can be prepared as follows:

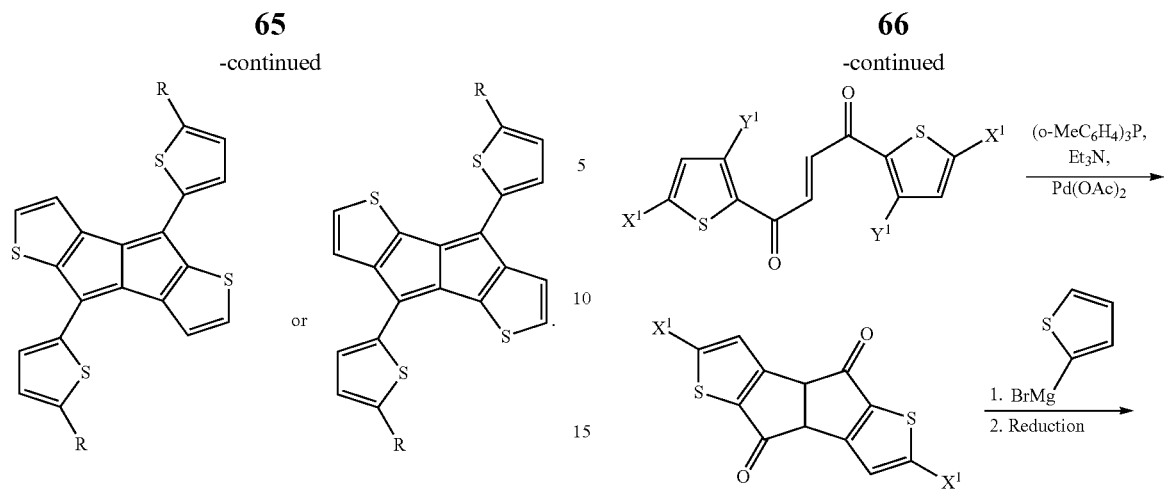

Alternatively, Compound 3 can be synthesized according to the procedures described in Scheme 10 below:

Scheme 10

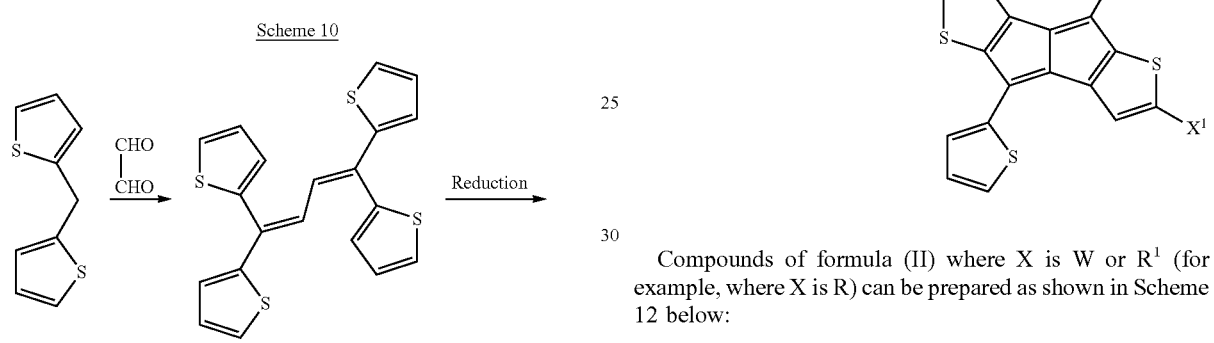

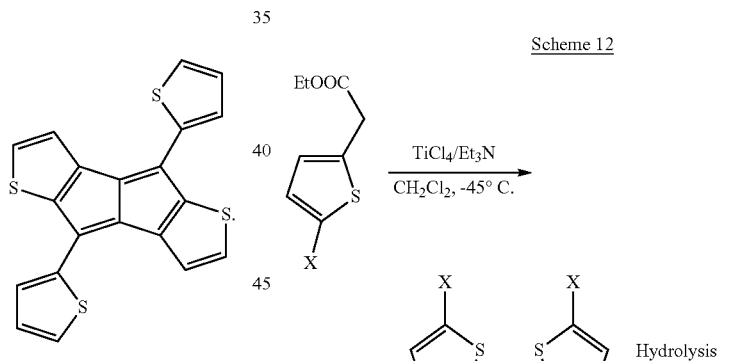

Example 1 below provides yet another synthetic route to Compound 3.

Compounds of formula (I) where X is a reactive group or a substitution group (represented by $X^1$ in Scheme 11 below), can be prepared as follows:

Scheme 11

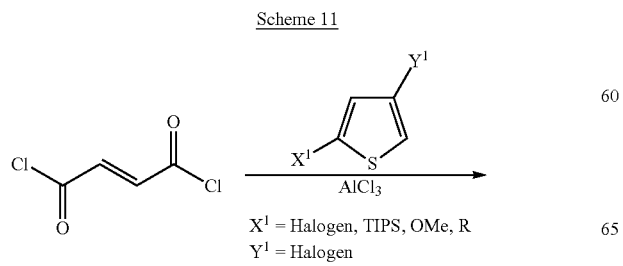

$X^1$ = Halogen, TIPS, OMe, R
$Y^1$ = Halogen

Compounds of formula (II) where X is W or $R^1$ (for example, where X is R) can be prepared as shown in Scheme 12 below:

Scheme 12

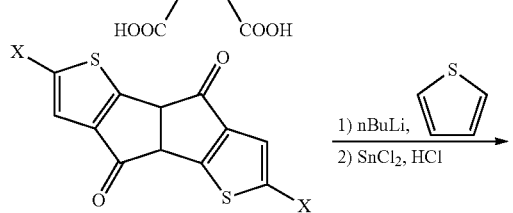

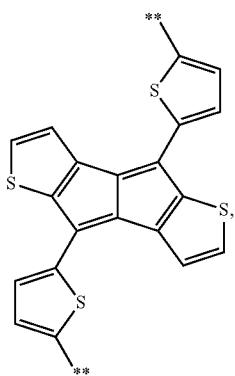

Compounds of formula (I) or formula (II) can be provided with reactive groups at either the alpha-omega fused positions (*) or the alpha-omega oligo positions (**):

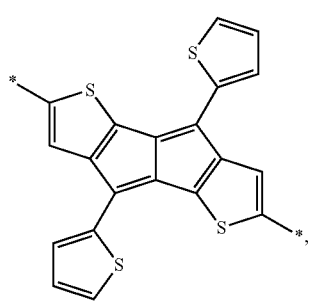

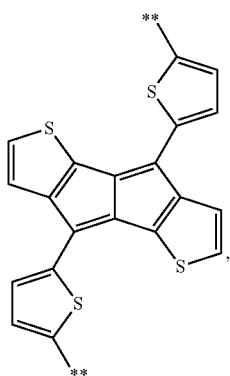

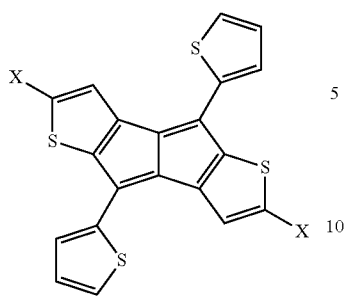

which then can be used to prepare compounds of formulae (I-b), (I-c), (I-d), (I-e), (I-f), (II-b), (II-c), (II-d), (II-e), and (II-f), as well as oligomeric and polymeric compounds of formula (III) and formula (IV).

For example, compounds of formulae (I-k), (I-l), (II-k), and (II-l) can be particularly useful as intermediates for preparing compounds of formulae (I-b), (I-c), (I-d), (I-e), (I-f), (II-b), (II-c), (II-d), (II-e), and (II-f) and as building blocks for preparing oligomeric and polymeric compounds of formula (III) and formula (IV):

(I-k)

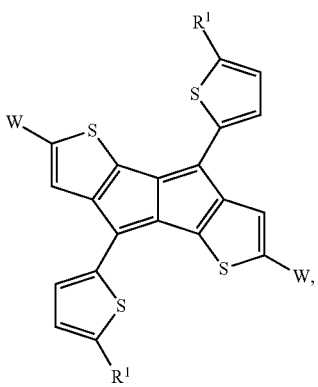

(I-l)

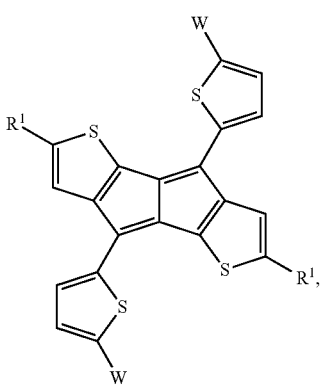

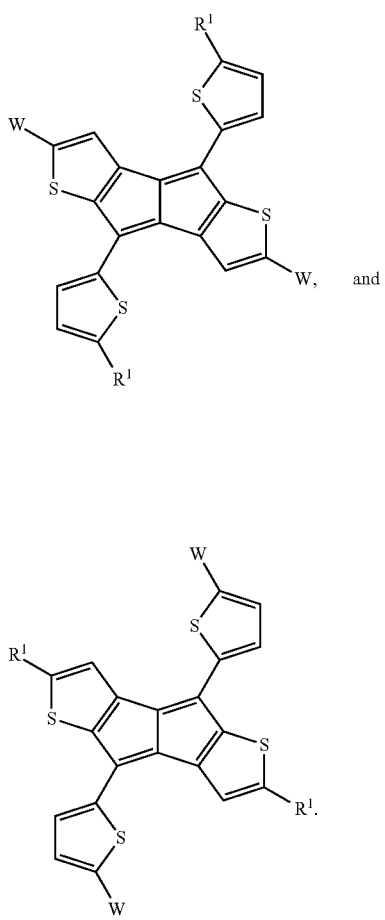

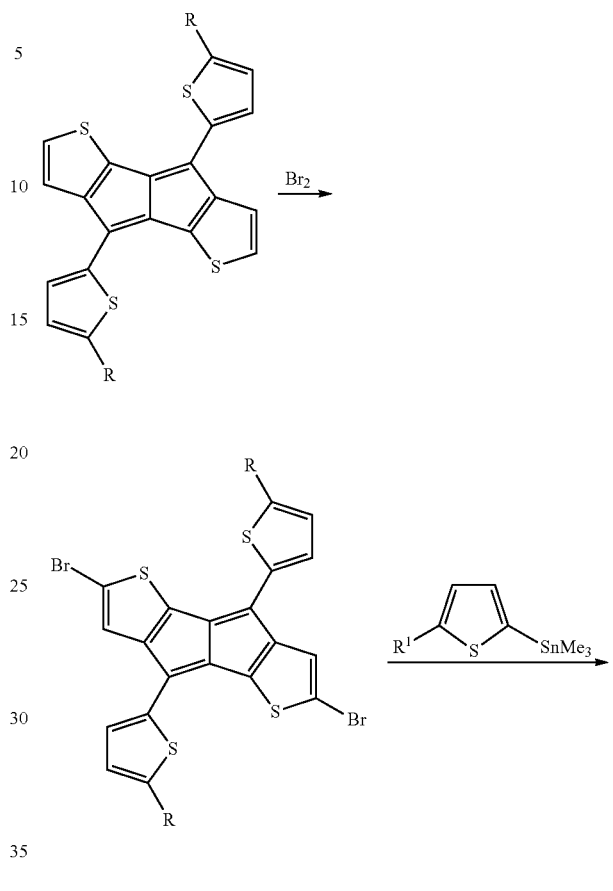

In preferred embodiments of compounds of formulae (I-k), (I-l), (II-k), and (II-l), each $R^1$ can be a solubilizing group (e.g., $C_{1-40}$ alkyl groups, $C_{1-40}$ haloalkyl groups, $C_{1-40}$ alkoxy groups, $C_{1-40}$ thioalkyl groups), and each W can be a halide or metallated group that is useful in various coupling reactions known to those skilled in the art, including those described in Yamamoto, *J. Organomet. Chem.*, 653: 195-199 (2002); Walton et al., *Polymer Chemistry* (Fred J. Davis ed. 2004), p. 158-187; and Galbrecht et al., *Macromolecular Rapid Communications*, 28(4): 387-394 (2007), the entire disclosure of each of which is incorporated by reference herein for all purposes. For example, W can be —Sn(alkyl)₃ for reaction with a compound bearing a halide (e.g., Br), or vice versa, via Stille coupling. Alternatively, W can be a borane/boronic acid/bornic ester for reaction with a compound bearing a halide (e.g., Br or I), or vice versa, via Suzuki coupling.

Schemes 13-15 below illustrate synthetic routes that can be used to prepare compounds of formulae (I-b), (I-c), (I-d), (I-e), (I-f), (II-b), (II-c), (II-d), (II-e), and (II-f).

Scheme 13

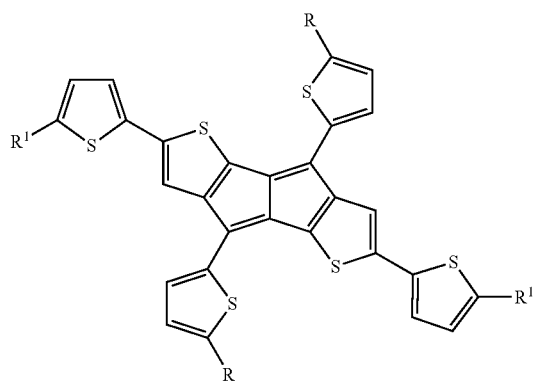

Scheme 14

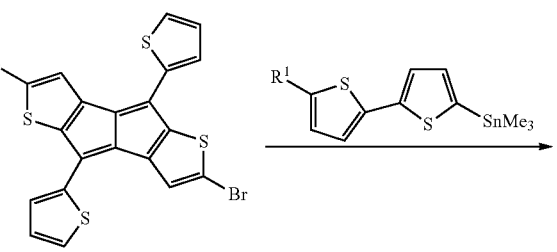

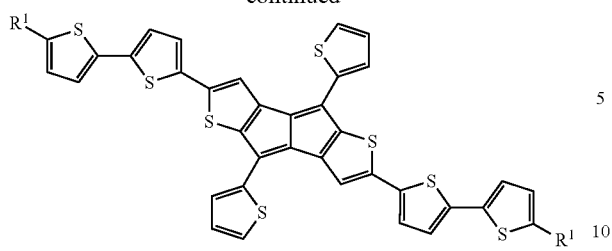

Scheme 15

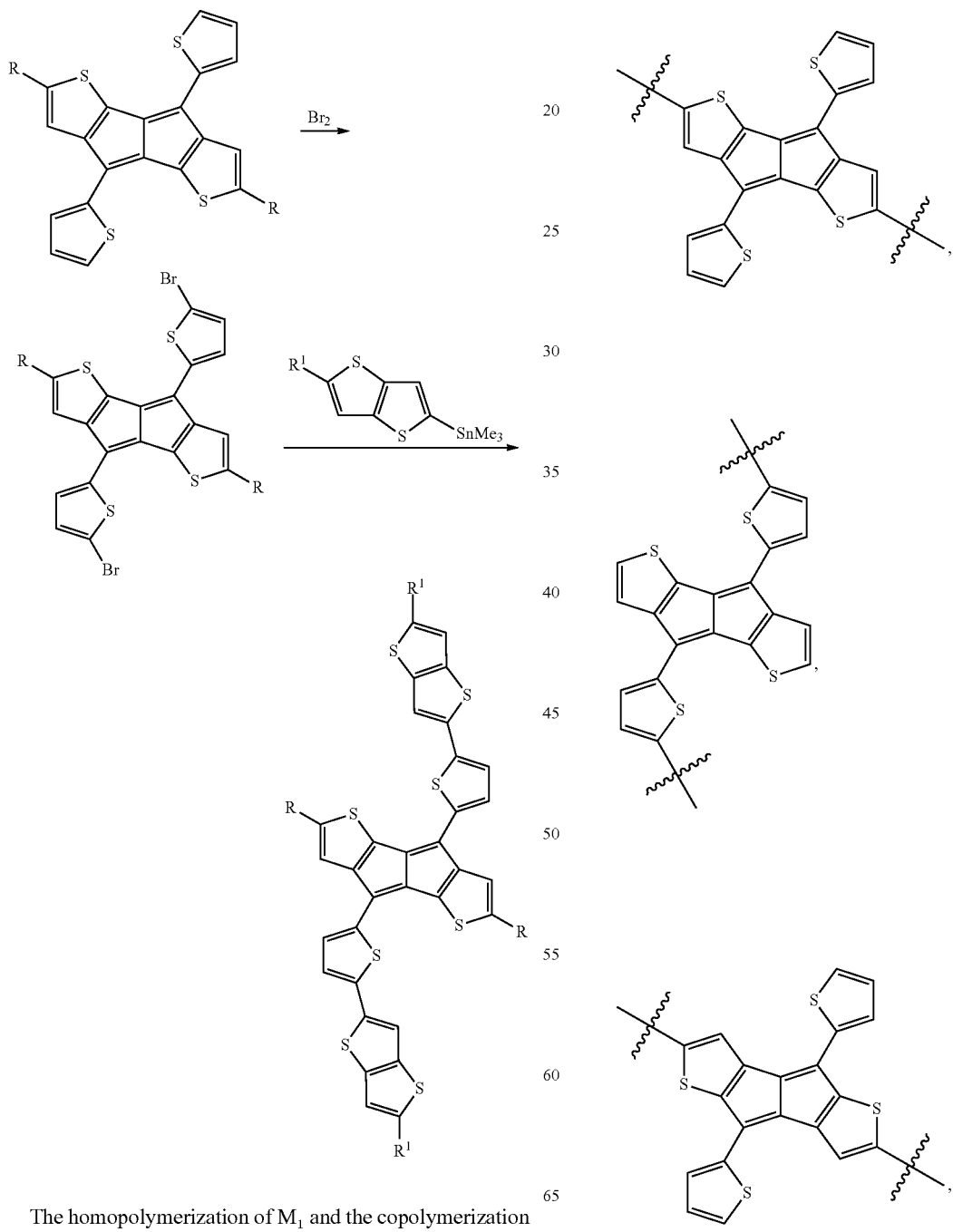

to those skilled in the art, including those described in Yamamoto, *J. Organomet. Chem.*, 653: 195-199 (2002); Walton et al., *Polymer Chemistry* (Fred J. Davis ed. 2004), p. 158-187; and Galbrecht et al., *Macromolecular Rapid Communications*, 28(4): 387-394 (2007), the entire disclosure of each of which is incorporated by reference herein for all purposes. In particular, Stille coupling or Suzuki coupling reactions can be used to prepare oligomeric and polymeric compounds according to the present teachings.

For example, oligomeric and polymeric compound of formula (III) can be prepared according to the general schemes illustrated in Scheme 16 and Scheme 17, where $M_{1a}$ can be pi-1, e.g., The homopolymerization of $M_1$ and the copolymerization of $M_1$ and $M_2$ can be achieved via various reactions known -continued

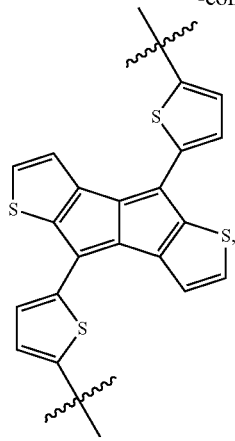

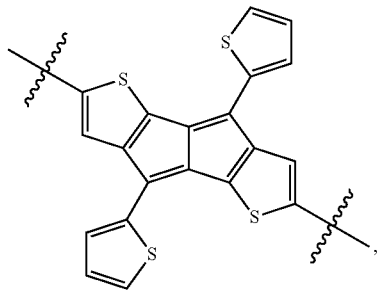

and $M_{1b}$ can be selected from —$(Ar)_m$—, —Z—, pi-2, —$(Ar)_m$—Z—, —$(Ar)_m$—Z—$(Ar)_m$—, —$(Ar)_m$-(pi-2)-$(Ar)_m$—, and —$(Ar)_m$—Z-(pi-2)-Z—$(Ar)_m$—.

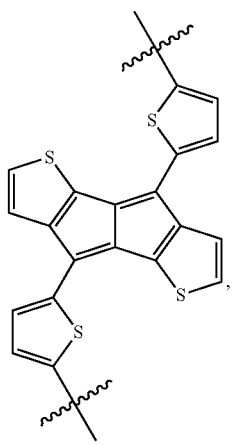

Scheme 16

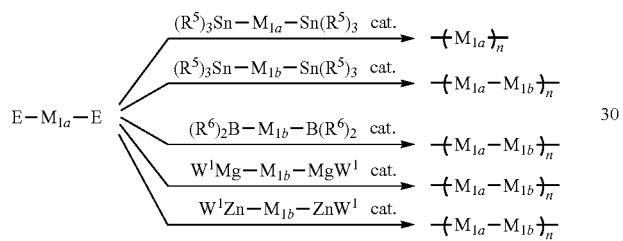

E = Halogen preferably Br

Scheme 17

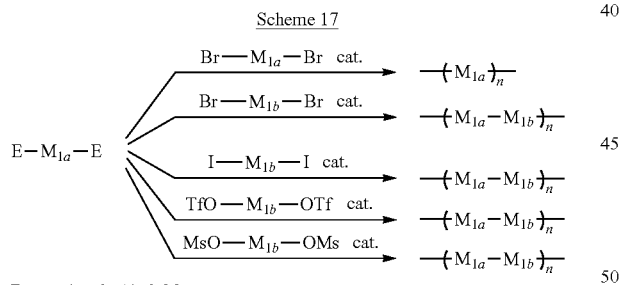

E = metal preferably SnMe₃

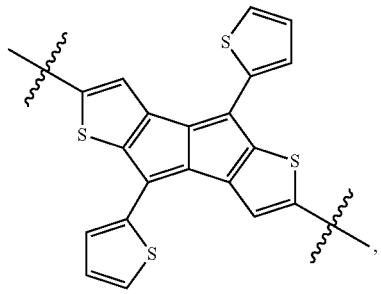

Co-monomers that can be useful according to the present teachings, e.g., the various derivatives of $M_{1b}$ shown in Schemes 16 and 17, can be commercially available, known in the literature, or can be prepared from readily prepared intermediates by employing standard synthetic methods and procedures known to those skilled in the art. Standard synthetic methods and procedures for the preparation of organic molecules and functional group transformations and manipulations can be readily obtained from the relevant scientific literature or from standard textbooks in the field.

Similarly, oligomeric and polymeric compound of formula (IV) can be prepared according to the general schemes illustrated in Scheme 18 and Scheme 19, where $M_{1a}$ can be pi-1, e.g.,

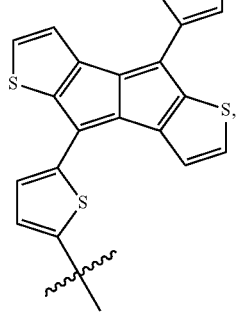

and $M_{1b}$ and $M_{2b}$ independently can be selected from —$(Ar)_m$—, —Z—, pi-2, —$(Ar)_m$—Z—, —$(Ar)_m$—Z—$(Ar)_m$—, —$(Ar)_m$ and —$(Ar)_m$—Z-(pi-2)-Z—$(Ar)_m$—.

Scheme 18

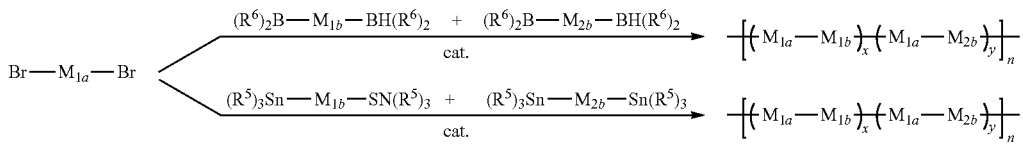

Scheme 19

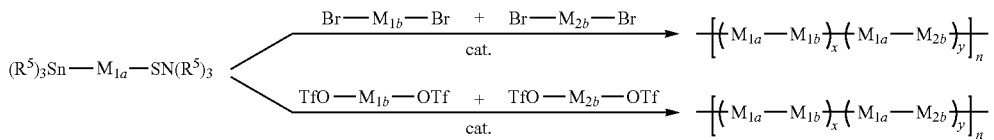

Compounds disclosed herein can be soluble in various common organic solvents. As used herein, a compound can be considered soluble in a solvent when at least 0.1 mg of the compound can be dissolved in 1 mL of the solvent. Examples of common organic solvents include petroleum ethers; acetonitrile; aromatic hydrocarbons such as benzene, toluene, xylene, and mesitylene; ketones such as acetone, and methyl ethyl ketone; ethers such as tetrahydrofuran, dioxane, bis(2-methoxyethyl) ether, diethyl ether, di-isopropyl ether, and t-butyl methyl ether; alcohols such as methanol, ethanol, butanol, and isopropyl alcohol; aliphatic hydrocarbons such as hexanes; esters such as methyl acetate, ethyl acetate, methyl formate, ethyl formate, isopropyl acetate, and butyl acetate; amides such as dimethylformamide and dimethylacetamide; sulfoxides such as dimethylsulfoxide; halogenated aliphatic and aromatic hydrocarbons such as dichloromethane, chloroform, ethylene chloride, chlorobenzene, dichlorobenzene, and trichlorobenzene; and cyclic solvents such as cyclopentanone, cyclohexanone, and 2-methypyrrolidone.

The compounds described herein can be dissolved, dispersed or suspended in a single solvent or mixture of solvents to provide a composition suitable for solution processing techniques. In preferred embodiments, the solvent can be selected from the group consisting of chlorobenzene, dichlorobenzene (o-dichlorobenzene, m-dichlorobenzene, p-orobenzene, or mixtures thereof), trichlorobenzene, benzene, toluene, chloroform, dichloromethane, dichloroethane, xylenes, α,α,α-trichlorotoluene, methyl naphthalene (e.g., 1-methylnaphthalene, 2-methylnaphthalene, or mixtures thereof), chloronaphthalene (e.g., 1-chloronaphthalene, 2-chloronaphthalene, or mixtures thereof), and mixtures thereof. Various solution processing techniques have been used with organic electronics. Common solution processing techniques include, for example, spin coating, slot coating, doctor blading, drop-casting, zone casting, dip coating, blade coating, or spraying. Another example of solution processing technique is printing. As used herein, "printing" includes a noncontact process such as inkjet printing, microdispensing and the like, and a contact process such as screen-printing, gravure printing, offset printing, flexographic printing, lithographic printing, pad printing, microcontact printing and the like.

Compounds of the present teachings can exhibit semiconductor behavior (including photoactive behavior) such as optimized light absorption/charge separation in a photovoltaic device; charge transport/recombination/light emission in a light-emitting device; and/or high carrier mobility and/or good current modulation characteristics in a field-effect device. In addition, the present compounds can possess certain processing advantages such as solution-processability and/or good stability (e.g., air stability) in ambient conditions. The compounds of the present teachings can be used alone or in combination with other compounds to prepare either p-type (donor or hole-transporting), n-type (acceptor or electron-transporting), or ambipolar semiconductor materials, which in turn can be used to fabricate various organic or hybrid optoelectronic articles, structures and devices, including organic photovoltaic devices and organic light-emitting transistors. In some embodiments, semiconductor materials incorporating one or more compounds of the present teachings can exhibit p-type semiconductor activity, ambipolar activity, light absorption, and/or light emission.

The present teachings, therefore, further provide methods of preparing a semiconductor material and composites (e.g., devices) including the semiconductor material. The methods can include preparing a composition (e.g., a solution or dispersion) that includes one or more compounds disclosed herein dissolved or dispersed in a liquid medium such as a solvent or a mixture of solvents, and depositing the composition on a substrate to provide a semiconductor material. The deposited semiconductor material can be processed further (e.g., subject to an annealing step) prior to formation of additional components thereon to complete a particular device structure.

Various articles of manufacture including optical devices, optoelectronic devices, and electronic devices such as thin film semiconductors, photovoltaic/solar cells, photodetectors (or photodiodes), organic light emitting devices such as organic light emitting transistors (OLETs), that make use of the compounds disclosed herein are within the scope of the present teachings as are methods of making the same. The present compounds can offer processing and operation advantages in the fabrication and/or the use of these devices.

In some embodiments, the article of manufacture can be an electronic or optoelectronic device (e.g., an organic light-emitting transistor) including a first electrode, a second electrode, and a semiconducting component in contact with the first electrode and the second electrode, where the semiconducting component includes a compound of the present teachings. These devices can include a composite having a semiconducting component (or semiconductor material) of the present teachings and a substrate component and/or a dielectric component. The substrate component can be selected from doped silicon, an indium tin oxide (ITO), ITO-coated glass, ITO-coated polyimide or other plastics, aluminum or other metals alone or coated on a polymer or other substrate, a doped polythiophene, and the like. The dielectric component can be prepared from inorganic dielectric materials such as various oxides (e.g., $SiO_2$, $Al_2O_3$, $HfO_2$), organic dielectric materials such as various polymeric materials (e.g., polycarbonate, polyester, polystyrene, polyhaloethylene, polyacrylate), and self-assembled superlattice/self-assembled nanodielectric (SAS/SAND) materials (e.g., as described in Yoon, M-H. et al., *PNAS*, 102 (13): 4678-4682 (2005), the entire disclosure of which is incorporated by reference herein), as well as hybrid organic/inorganic dielectric materials (e.g., described in U.S. patent application Ser. No. 11/642,504, the entire disclosure of which is incorporated by reference herein). In some embodiments, the dielectric component can include the crosslinked polymer blends described in U.S. patent application Ser. Nos. 11/315,076, 60/816,952, and 60/861,308, the entire disclosure of each of which is incorporated by reference herein. The composite also can include one or more electrical contacts. Suitable materials for the source, drain, and gate electrodes include metals (e.g., Au, Al, Ni, Cu), transparent conducting oxides (e.g., ITO, IZO, ZITO, GZO, GIO, GITO), and conducting polymers (e.g., poly(3,4-ethylenedioxythiophene) poly(styrenesulfonate) (PEDOT:PSS), polyaniline (PANI), polypyrrole (PPy)).

FIG. 1 illustrates the four common types of OFET structures: (a) bottom-gate top-contact structure, (b) bottom-gate bottom-contact structure, (c) top-gate bottom-contact structure, and (d) top-gate top-contact structure. As shown in FIG. 1, an OFET can include a dielectric layer (e.g., shown as 8, 8', 8", and 8" in FIGS. 1*a*, 1*b*, 1*c*, and 1*d*, respectively), a semiconductor/channel layer (e.g., shown as 6, 6', 6", and 6" in FIGS. 1*a*, 1*b*, 1*c*, and 1*d*, respectively), a gate contact (e.g., shown as 10, 10', 10", and 10" in FIGS. 1*a*, 1*b*, 1*c*, and 1*d*, respectively), a substrate (e.g., shown as 12, 12', 12", and 12" in FIGS. 1*a*, 1*b*, 1*c*, and 1*d*, respectively), and source and drain contacts (e.g., shown as 2, 2', 2", 2", 4, 4', 4", and 4" in FIGS. 1*a*, 1*b*, 1*c*, and 1*d*, respectively).

In other embodiments, the article of manufacture can be an optical or optoelectronic device including a first electrode, a second electrode, and a photoactive component disposed between the first electrode and the second electrode, where the photoactive component includes a compound of the present teachings.

In various embodiments, the optical or optoelectronic device can be configured as a solar cell, in particular, a bulk heterojunction solar cell. Compounds of the present teachings can exhibit broad optical absorption and/or a tuned redox properties and bulk carrier mobilities, making them desirable for such applications. In some embodiments, the bulk heterojunction solar cells according to the present teachings can incorporate a blend material (e.g., a blended film) including a compound (e.g., a polymer) of the present teachings as the donor material and an acceptor material as the photoactive layer. Typical acceptor materials include fullerene-based compounds. Fullerenes useful in the present teachings can have a broad range of sizes (number of carbon atoms per molecule). The term fullerene as used herein includes various cage-like molecules of pure carbon, including Buckministerfullerene ($C_{60}$) "bucky ball" and the related "spherical" fullerenes as well as carbon nanotubes. Fullerenes can be selected from those known in the art ranging from, for example, $C_{20}$-$C_{1000}$. In certain embodiments, the fullerene can be selected from the range of $C_{60}$ to $C_{96}$. In particular embodiments, the fullerene can be a $C_{60}$ fullerene derivative or a $C_{70}$ fullerene derivative, such as [6,6]-phenyl-$C_{61}$-butyric acid methyl ester ($PC_{61}BM$ or simply PCBM) or [6,6]-phenyl-$C_{71}$-butyric acid methyl ester ($PC_{71}BM$). In some embodiments, chemically modified fullerenes can be used, provided that the modified fullerene retains acceptor-type and electron mobility characteristics. Some common fullerene derivatives include bisadduct of $PC_{61}BM$ (Bis-PCBM), indene-$C_{60}$ monoadduct (ICMA), and indene-$C_{60}$ bisadduct (ICBA). Further, other acceptor materials can be used in place of fullerenes, provided that they have the required acceptor-type and electron mobility characteristics. For example, the acceptor material can be various organic small molecules, polymers, carbon nanotubes, or inorganic particles (quantum dots, quantum rods, quantum tripods, $TiO_2$, ZnO etc.).

In some embodiments, the acceptor material can be an electron-transporting (n-type) polymer. In some embodiments, the electron-transporting polymer can comprise a bis(imide)arene unit. Exemplary polymers are described in U.S. Patent Publication Nos. 2010/0326527, 2010/0326527, and 2010/0283047.

In some embodiments, the bulk heterojunction solar cells according to the present teachings can incorporate a blend material (e.g., a blended film) including a polymer of the present teachings as the acceptor material and a donor material as the photoactive layer. For example, embodiments of the present polymers that can function as an acceptor material include those having a bis(imide)arene unit, for example, a naphthalene diimide, as the pi-2 moiety. Many donor polymers have been reported, the most well-known being poly(3-hexylthiophene) or P3HT. Many donor polymers have an alternating push-pull structure:

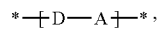

where the donor subunit (D) often includes a bridged dithiophene moiety (such as a benzodithiophene moiety, a naphthodithiophene moiety, a thienodithiophene moiety, and a pyridodithiophene moiety); the acceptor subunit (A) can include an electron-poor conjugated moiety; and either the donor subunit (D) or the acceptor subunit (A) can comprise one or more thienyl or thienothienyl groups. Suitable donor polymers are described in, for example, U.S. Patent Publication No. US 2013/0247992 and Facchetti, "Pi-Conjugated Polymers for Organic Electronics and Photovoltaic Cell Applications," *Chem. Mater.*, 23:733-758 (2011).

A photoactive component according to the present teachings can be prepared as a blended film deposited from a solution or dispersion containing a mixture of one or more of the present compounds and either an acceptor compound such as fullerene (e.g., PCBM) or a polymeric acceptor described herein, or a donor polymer. The ratio of the donor polymer to the acceptor compound can range from about 10:1 to about 1:10 by weight; for example, from about 5:1 to about 1:5 by weight, from about 3:1 to about 1:3 by weight, or from about 2:1 to about 1:2 by weight. The photoactive layer also can contain a polymeric binder, which can be present from about 5 to about 95% by weight. The polymeric binder, for example, can be a semicrystalline polymer selected from polystyrene (PS), high density polyethylene (HDPE), polypropylene (PP) and polymethylmethacrylate (PMMA). In some embodiments, the polymeric blend can be used together with additional components that are optically active, for example, components that can assist in light harvesting by capturing and transferring excitons to one or both of the electron-donor polymers/electron-acceptor polymers in the blend, and/or optically non-active components to modify and/or improve processing and/or device performance. Such optically non-active components can include alkanethiols (e.g., alkanedithiols) and other α,ω-functionalized alkanes (e.g., diiodoalkanes) as known in the art. See e.g., U.S. Pat. No. 8,227,691.

The blend composition can be deposited on a substrate (e.g., an electrode-substrate) preferably via a solution-phase process, followed by removal of the solvent or mixture of solvents to provide the photoactive layer. By having the blend composition provided as an intimate mixture of the present polymer and an acceptor compound, bulk heterojunctions are created upon removal of the solvent (optionally under reduced pressure and/or elevated temperature), during which nanoscale phase separation of the present donor polymers and the acceptor compound takes place. In some embodiments, the depositing step can be carried out by printing, including inkjet printing and various contact printing techniques (e.g., screen-printing, gravure printing, offset printing, pad printing, lithographic printing, flexographic printing, and microcontact printing). In other embodiments, the depositing step can be carried out by spin coating, slot-die coating, drop-casting, zone casting, dip coating, blade coating, or spraying. When the film is formed by spin coating, the spin speed can range from about 300 rpm to about 6000 rpm, or from about 500 rpm to about 2000 rpm. Subsequent processing steps can include thermal annealing or irradiation of the deposited film. For example, the blended film can be annealed from about 50° C. to about 300° C., preferably from about 70° C. to about 200° C., more preferably from about 90° C. to about 180° C. for about 1 min to about 20 minutes. The annealing step can be carried out under an inert atmosphere (e.g., under nitrogen). Irradiation of the deposited film can be carried out using infrared light or ultraviolet light. As used herein, "annealing" refers to a post-deposition heat treatment to the semicrystalline polymer film in ambient or under reduced/increased pressure for a time duration of more than 60 seconds, and "annealing temperature" refers to the maximum temperature that the polymer film is exposed to for at least 30 seconds during this process of annealing. The photoactive layer typically can have a thickness ranging from about 30 nm to about 500 nm. In preferred embodiments, the photoactive layer can be a thin film having a thickness of about 80-300 nm.

Figure 2:
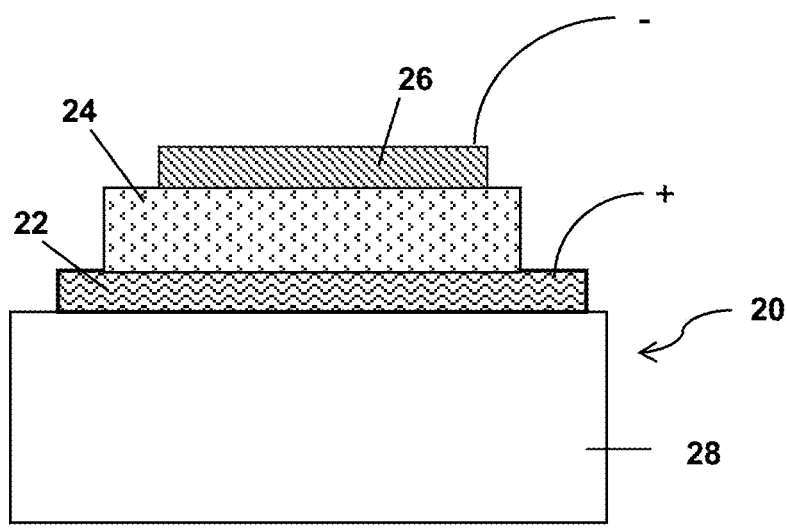
FIG. 2 illustrates a representative structure of a bulk-heterojunction organic photovoltaic device (also known as a solar cell), which can incorporate one or more compounds of the present teachings as the donor and/or acceptor materials.

FIG. 2 illustrates a representative structure of a bulk-heterojunction organic solar cell which can incorporate one or more compounds of the present teachings as either the donor material or the acceptor material. As shown, a representative solar cell 20 generally includes an anode 22, a cathode 26, and a photoactive layer 24 between the anode and the cathode that can incorporate one or more polymers of the present teachings as either the electron donor (p-channel) material or the electron acceptor (n-channel) material. In some embodiments, an optional smoothing layer can be present between the anode and the photoactive layer.

The substrate 28 can be a solid, rigid or flexible layer designed to provide robustness to the device. In preferred embodiments, the substrate can be transparent or semi-transparent in the spectral region of interest. As used herein, a material is considered "transparent" when it has transmittance over 50%, and a material is considered "semi-transparent" when it has transmittance between about 50% and about 5%. The substrate can comprise any suitable material known in the art such as glass or a flexible plastic (polymer) film.

The first and second electrodes should have different work functions, with the electrode having the higher work function at or above about 4.5 eV (the "high work function electrode") serving as the hole-injecting electrode or anode, and the electrode having the lower work function at or below about 4.3 eV (the "low work function electrode") serving as the electron-injecting electrode. In a traditional OPV device structure, the high work function electrode or anode typically is composed of a transparent conducting metal oxide or metal sulfide such as indium tin oxide (ITO), gallium indium tin oxide (GITO), and zinc indium tin oxide (ZITO), or a thin, transparent layer of gold or silver. The low work function electrode or cathode typically is composed of a low work function metal such as aluminum, indium, calcium, barium, and magnesium. The electrodes can be deposited by thermal vapor deposition, electron beam evaporation, RF or magnetron sputtering, chemical vapor deposition or the like.

In various embodiments, the solar cell can include one or more optional interface layers ("interlayers") between the anode and the photoactive layer and/or between the cathode and the photoactive layer. For example, in some embodiments, an optional smoothing layer (e.g., a film of 3,4-polyethylenedioxythiophene (PEDOT), or 3,4-polyethylenedioxythiophene:polystyrene-sulfonate (PEDOT:PSS)) can be present between the anode and the photoactive layer. The optional interlayer(s) can perform other functions such as reducing the energy barrier between the photoactive layer and the electrode, forming selective contacts for a single type of carrier (e.g., a hole-blocking layer), modifying the work function of the adjacent electrode, and/or protecting the underlying photoactive layer. In some embodiments, a transition metal oxide layer such as $V_2O_5$, $MoO_3$, $WO_3$ and NiO can be deposited on top of the ITO anode, instead of using PEDOT or PEDOT:PSS as the p-type buffer. To improve device stability via modification of the cathode, an n-type buffer composed of LiF, CsF or similar fluorides can be provided between the cathode and the photoactive layer. Other n-type buffer materials include $TiO_x$, $ZnO_x$ and Cs-doped $TiO_x$. Depending on the composition, the interlayers can be solution-processed (e.g., sol-gel deposition, self-assembled monolayers) or deposited by vacuum processes such as thermal evaporation or sputtering.

In certain embodiments, a solar cell according to the present teachings can include a transparent glass substrate onto which an electrode layer (anode) made of indium tin oxide (ITO) is applied. This electrode layer can have a relatively rough surface, and a smoothing layer made of a polymer, typically PEDOT:PSS made electrically conductive through doping, can be applied on top of the electrode layer to enhance its surface morphology. Other similar interlayers can be optionally present between the anode and the photoactive layer for improving mechanical, chemical, and/or electronic properties of the device. The photoactive layer is composed of an all-polymer blend as described above, and can have a layer thickness of, e.g., about 80 nm to a few µm. Before a counter electrode (cathode) is applied, an electrically insulating transition layer can be applied onto the photoactive layer. This transition layer can be made of an alkali halide, e.g., LiF, and can be vapor-deposited in vacuum. Again, similar to the anode, other similar interlayers can be optionally present between the photoactive layer and the cathode for improving mechanical, chemical, and/or electronic properties of the device.

In certain embodiments, a solar cell according to the present teachings can have an inverted device structure, where a modified ITO film is used as the cathode. For example, the ITO can be modified by n-type metal oxides or metal carbonates such as $TiO_x$, $ZnO_x$, Cs-doped $TiO_x$, and caesium carbonate. In particular embodiments, the inverted OPV can include a solution-processed $ZnO_x$ n-type interface layer as described in Lloyd et al., "Influence of the hole-transport layer on the initial behavior and lifetime of inverted organic photovoltaics," *Solar Energy Materials and Solar Cells*, 95(5): 1382-1388 (2011). Compared with the traditional device structure, inverted-type devices can demonstrate better long-term ambient stability by avoiding the need for the corrosive and hygroscopic hole-transporting PEDOT:PSS and low work function metal cathode. The anode of an inverted OPV cell can be composed of Ag, Au, and the like, with an optional p-type interface layer composed of transition metal oxides such as $V_2O_5$, $MoO_3$, $WO_3$ and NiO.

Another aspect of the present teachings relates to methods of fabricating an organic light-emitting transistor or an organic light-emitting diode (OLED) that incorporates one or more semiconductor materials of the present teachings. For example, in an OLED, one or more compounds of the present teachings can be used as electron-transporting and/or emissive and/or hole-transporting materials. An OLED generally includes a substrate, a transparent anode (e.g., ITO), a cathode (e.g., metal), and one or more organic layers which can incorporate one or more compounds of the present teachings as hole-transporting (p-channel) and/or emissive and/or electron-transporting (n-channel) materials. In embodiments where the present compounds only have one or two of the properties of hole transport, electron transport, and emission, the present compounds can be blended with one or more further organic compounds having the remaining required property or properties.

Figure 3:
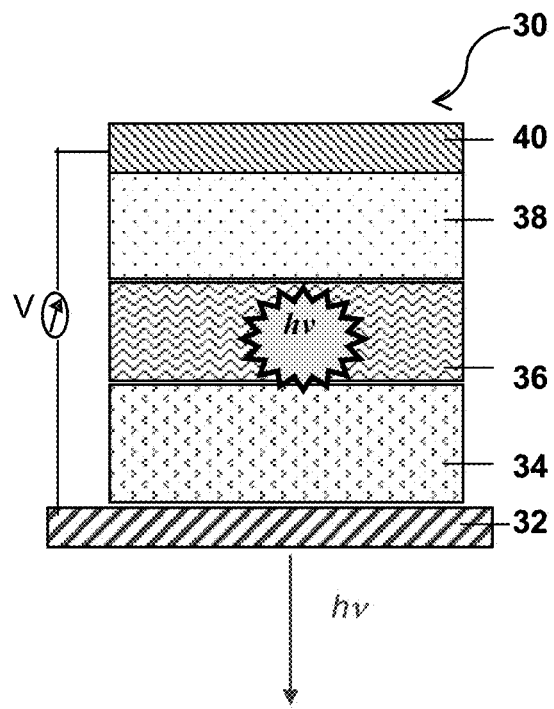
FIG. 3 illustrates a representative structure of an organic light-emitting device which can incorporate one or more compound of the present teachings as electron-transporting and/or emissive and/or hole-transporting materials.

FIG. 3 illustrates a representative structure of an OLED which can incorporate one or more polymers of the present teachings as electron-transporting and/or emissive and/or hole-transporting materials. As shown, an OLED generally includes a substrate 30 (not shown), a transparent anode 32 (e.g., ITO), a cathode 40 (e.g., metal), and one or more organic layers which can incorporate one or more polymers of the present teachings as hole-transporting (n-channel) (layer 34 as shown) and/or emissive (layer 36 as shown) and/or electron-transporting (p-channel) materials (layer 38 as shown).

The following examples are provided to illustrate further and to facilitate the understanding of the present teachings and are not in any way intended to limit the invention.

Example 1

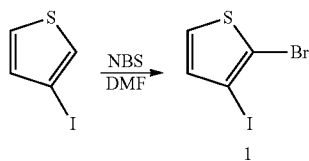

Synthesis of 2-bromo-3-iodothiophene (1). A solution of 3-iodothiophene (1.10 g, 5.20 mmol) in anhydrous DMF (27 mL) was cooled in an ice bath under $N_2$ and NBS (0.98 g, 5.5 mmol) was added in a single portion. The reaction was protected from light, stirred for 16 h and then heated to 50° C. for 1.5 h. After cooling to room temperature the solution was poured into hexanes (100 mL) and washed with brine (3×100 mL). The organic layer was dried over $MgSO_4$, concentrated, and purified by column chromatography using hexanes as eluent to yield 1.08 g (72%) colorless liquid. $^1$H NMR (400 MHz, $CDCl_3$) δ 7.22 (d, 2H), 6.94 (d, 2H).

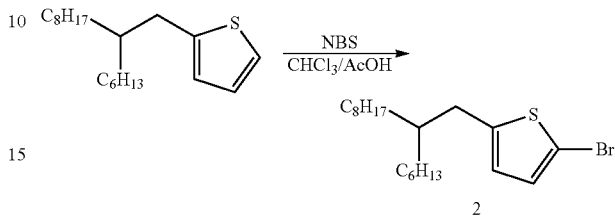

Synthesis of 2-bromo-5-(2-hexyldecyl)thiophene (2). A solution of 2-(2-hexyldecyl)thiophene (1.01 g, 3.27 mmol) in $CHCl_3$ (8 mL) and AcOH (8 mL) was chilled in an ice/salt bath under $N_2$ and NBS (0.580 g, 3.27 mmol) was added in four equal portions over 0.5 h. The mixture was allowed to reach ambient temperature and stirred overnight. The solvents were evaporated under reduced pressure and the residue was filtered through a plug of silica gel using hexanes as eluent to yield 1.13 g (90%) colorless liquid. $^1$H NMR (400 MHz, $CDCl_3$) δ 6.83 (d, 1H), 6.49 (d, 1H), 2.66 (d, 2H), 1.55 (m, 1H), 1.25 (m, 24H), 0.87 (m, 6H).

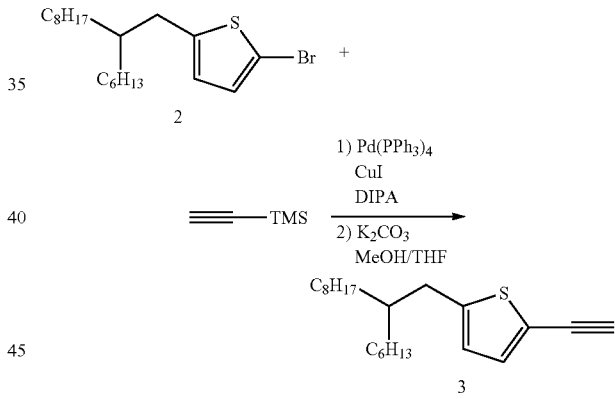

Synthesis of 2-ethynyl-5-(2-hexyldecyl)thiophene (3). 2-Bromo-5-(2-hexyldecyl)thiophene (2) (4.30 g, 11.1 mmol) and anhydrous N,N'-diisopropylamine (65 mL) were added to an oven-dried Schlenk flask and sparged with $N_2$ for 20 minutes. $Pd(PPh_3)_4$ (0.39 g, 0.3 mmol) was added and the solution was heated to 40° C. for 15 minutes before trimethylsilylacetylene (1.64 g, 16.6 mmol) and CuI (0.074 g, 0.4 mmol) were added and the reaction was heated to reflux overnight. The reaction mixture was concentrated under reduced pressure and filtered through a pad of silica gel using hexanes as eluent yielding 4.40 g colorless liquid (98%) that was used directly in the next step without further purification.

The obtained liquid (3.40 g, 8.40 mmol) was dissolved in methanol (150 mL) and THF (15 mL) containing $K_2CO_3$ (5.80 g, 42.0 mmol) and the solution was heated to reflux overnight under $N_2$. The reaction was cooled to room temperature and the mixture was filtered, diluted with hexanes (200 mL) and extracted with 10% HCl solution (3×75 mL). The organic layer was dried over MgSO$_4$, filtered and evaporated to yield 2.50 g (90%) yellow liquid. $^1$H NMR (400 MHz, CDCl$_3$) δ 7.08 (d, 2H), 6.59 (d, 2H), 3.27 (s, 1H), 2.69 (d, 2H), 1.59 (m, 1H), 1.24 (m, 24H), 0.87 (m, 6H).

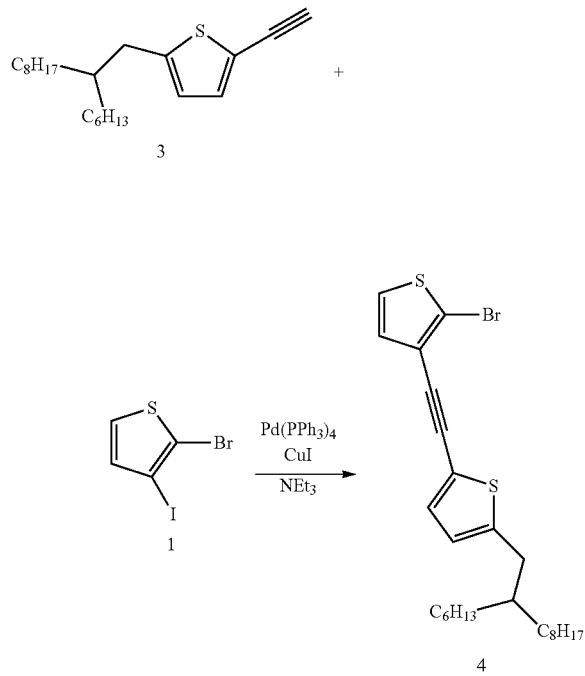

Synthesis of Compound 4.

2-Bromo-3-iodothiophene (1) (2.99 g, 10.4 mmol), Pd(PPh$_3$)$_4$ (0.3590 g, 0.3 mmol) and CuI (0.0690 g, 0.3 mmol) were dissolved in NEt$_3$ (117 mL) under N$_2$. 2-Ethynyl-5-(2-hexyldecyl)thiophene (3) (3.44 g, 10.4 mmol) was added dropwise via syringe and the solution was stirred at room temperature overnight. The solvent was evaporated and the mixture was purified by column chromatography on silica gel using hexanes as eluent yielding 4.37 g (85%) viscous yellow liquid as product. $^1$H NMR (400 MHz, CDCl$_3$) δ 7.19 (d, 2H), 7.12 (d, 2H), 6.98 (d, 2H), 6.63 (d, 2H), 2.71 (d, 2H), 1.60 (m, 1H), 1.26 (m, 24H), 0.87 (m, 6H).

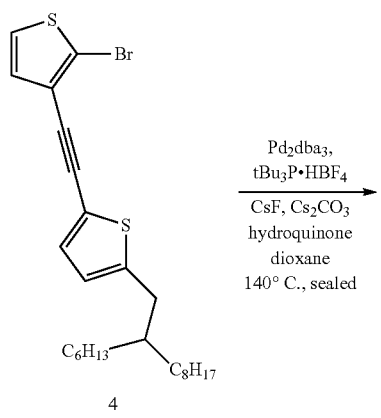

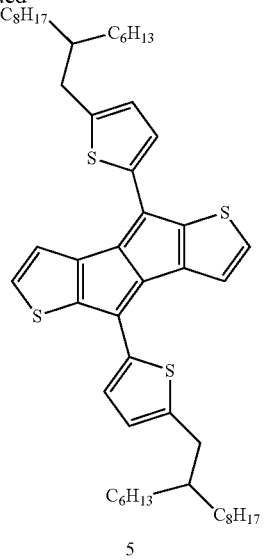

Synthesis of Compound 5.

An oven-dried glass pressure tube was cooled under N$_2$ flow and charged with Pd$_2$dba$_3$ (0.0280 g, 0.03 mmol), tBu$_3$P.HBF$_4$ (0.0350 g, 0.1 mmol), hydroquinone (0.4460 g, 4.1 mmol), dry CsF (0.6770 g, 4.5 mmol) and dry Cs$_2$CO$_3$ (1.32 g, 4.1 mmol). In a separate vial, a solution of 4 (1.00 g, 2.0 mmol) in anhydrous dioxane (10 mL) was sparged with N$_2$ for 15 minutes, then added to the catalyst mixture via syringe. The tube was sealed and immediately placed in a preheated 140° C. oil bath and stirred for 18 h. After cooling the reaction mixture to room temperature it was diluted with 25 mL of hexanes, filtered through a pad of Celite® and concentrated. Purification by column chromatography on silica gel using hexanes as eluent yielded 0.025 g (7%) of a red solid. $^1$H NMR (400 MHz, CDCl$_3$) δ 7.23 (d, 2H), 6.99 (d, 2H), 6.85 (d, 2H), 6.74 (d, 2H), 2.77 (d, 4H), 1.66 (m, 2H), 1.47 (m, 48H), 0.87 (m, 12H).

All publications, including but not limited to patents and patent applications, cited in this specification are herein incorporated by reference as if each individual publication were specifically and individually indicated to be incorporated by reference herein as though fully set forth.

The present teachings encompass embodiments in other specific forms without departing from the spirit or essential characteristics thereof. The foregoing embodiments are therefore to be considered in all respects illustrative rather than limiting on the present teachings described herein. Scope of the present invention is thus indicated by the appended claims rather than by the foregoing description, and all changes that come within the meaning and range of equivalency of the claims are intended to be embraced therein.

The invention claimed is:

1. A polymer comprising a first repeating unit of the formula:

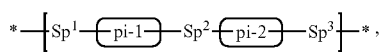

wherein:

pi-1 has a formula selected from the group consisting of:

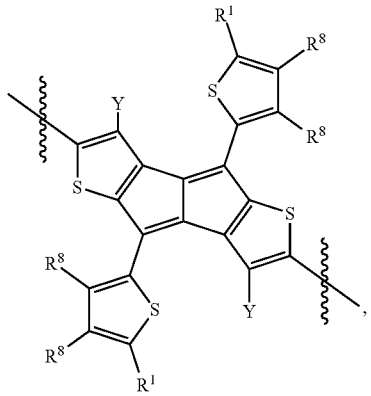

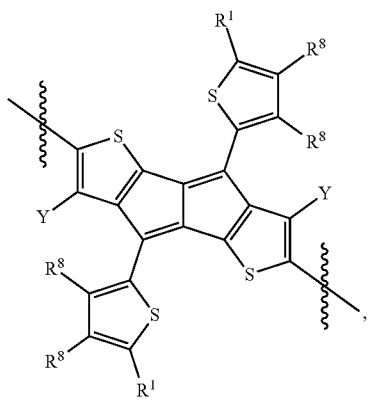

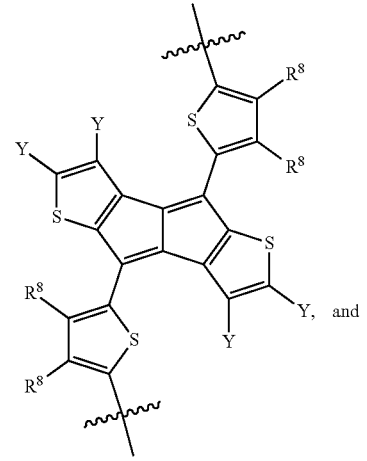

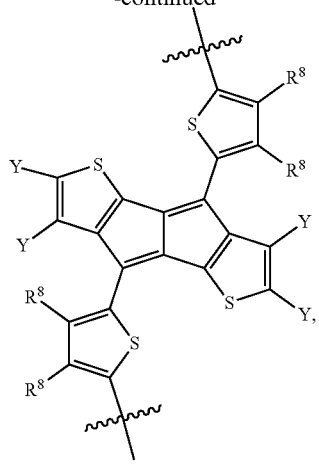

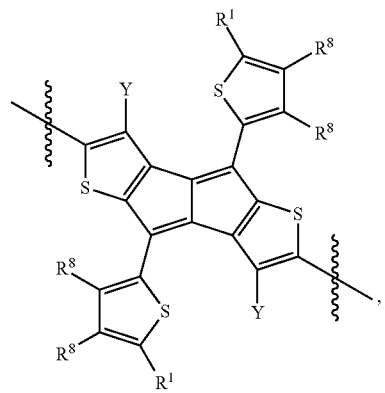

wherein:
- Y, at each occurrence, independently is selected from the group consisting of halogen, $R^1$, and $-(Ar^1)_p-R^1$;
- $Ar^1$, at each occurrence, independently is an optionally substituted divalent $C_{6-20}$ aryl or 5-20 membered heteroaryl group;
- $R^1$, at each occurrence, independently is selected from the group consisting of H, —CN, —NO$_2$, —OR, —SR, —C(O)OR, —C(O)R, —Si(R)$_3$, and R;
- $R^8$, at each occurrence, independently is H or $R^7$; wherein $R^7$ is selected from the group consisting of halogen, —CN, —NO$_2$, —OR, —SR, —C(O)OR, —C(O)R, —Si(R)$_3$, and R;
- wherein R is selected from the group consisting of a $C_{1-40}$ alkyl group, a $C_{1-40}$ haloalkyl group, a $C_{2-40}$ alkenyl group, and a $C_{2-40}$ alkynyl group; and
- p is 1, 2, 3 or 4;

pi-2 is a covalent bond or an optionally substituted conjugated polycyclic moiety that is different from pi-1; and $Sp^1$, $Sp^2$, and $Sp^3$ independently are a covalent bond or a conjugated spacer group comprising at least one of a conjugated linear linker and an optionally substituted conjugated monocyclic moiety.

2. The polymer of claim 1, wherein pi-1 is selected from the group consisting of:

-continued

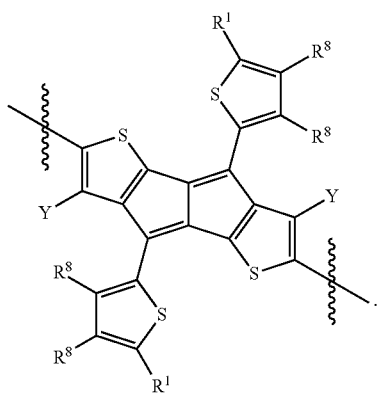

3. The polymer of claim 1, wherein $Sp^1$, $Sp^2$, and $Sp^3$ independently are selected from the group consisting of:

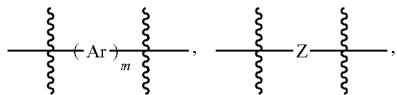

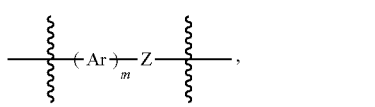

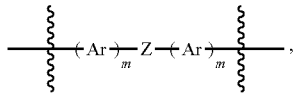

and a covalent bond, wherein each Ar independently is an optionally substituted conjugated monocyclic moiety; Z is a conjugated linear linker; and m is 1, 2, 3, 4 or 5.

4. The polymer of claim 3, wherein each Ar independently is an optionally substituted monocyclic 5- or 6-membered aryl or heteroaryl group.

5. The polymer of claim 3, wherein Z is selected from the group consisting of:

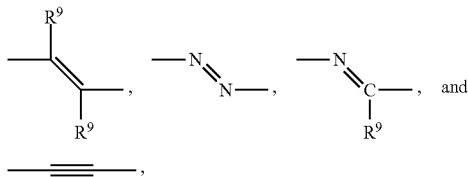

wherein each $R^9$ independently is selected from the group consisting of H, a halogen, CN, a $C_{1-40}$ alkyl group, a $C_{1-40}$ haloalkyl group, a $C_{1-40}$ alkoxy group, and a $C_{1-40}$ alkylthio group.

6. The polymer of claim 3, wherein the first repeating unit has the formula:

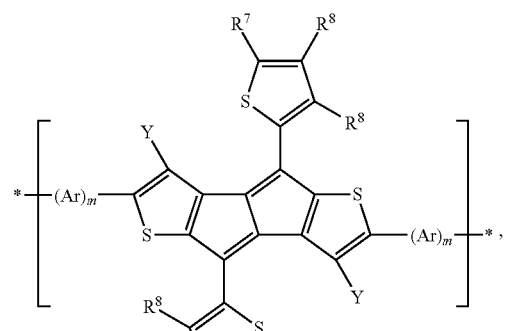

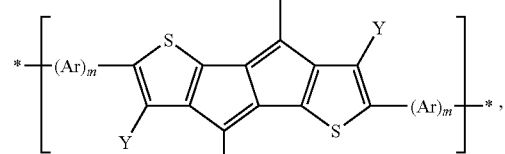

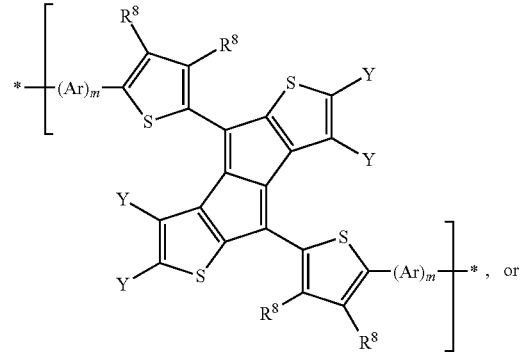

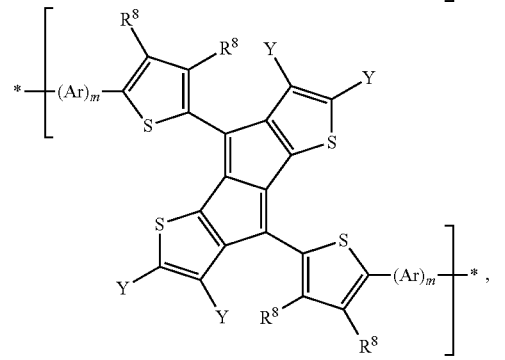

wherein each $R^1$ independently is selected from the group consisting of H, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group; each $R^8$, independently is selected from the group consisting of H, halogen, a $C_{1-40}$ alkyl group, a $C_{2-40}$ alkenyl group, a $C_{2-40}$ alkynyl group, $C_{1-40}$ haloalkyl group, a $C_{1-40}$ alkoxy group, and a $C_{1-40}$ thioalkyl group; and each Y, independently is selected from the group consisting of H, F, Cl, a linear or branched $C_{1-40}$ alkyl group, a linear or branched $C_{1-40}$ haloalkyl group, a linear or branched $C_{2-40}$ alkenyl group, a linear or branched $C_{2-40}$ alkynyl group, a linear or branched $C_{1-40}$ alkoxy group, and a linear or branched $C_{1-40}$ thioalkyl group.

7. The polymer of claim 6, wherein the first repeating unit has the formula:

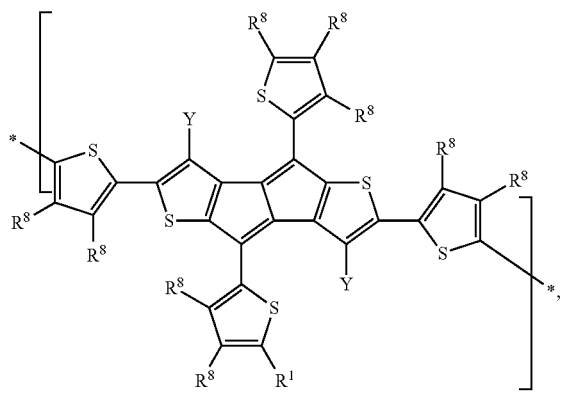

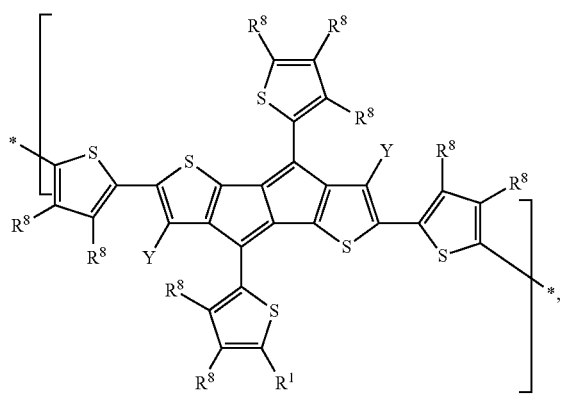

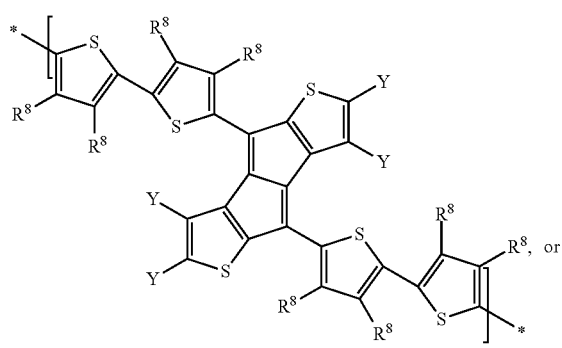

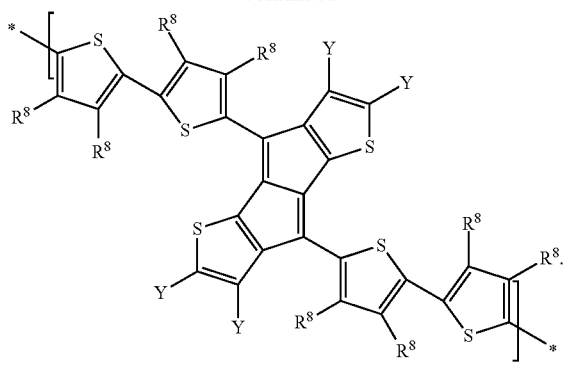

8. The polymer of claim 3, wherein the first repeating unit has the formula:

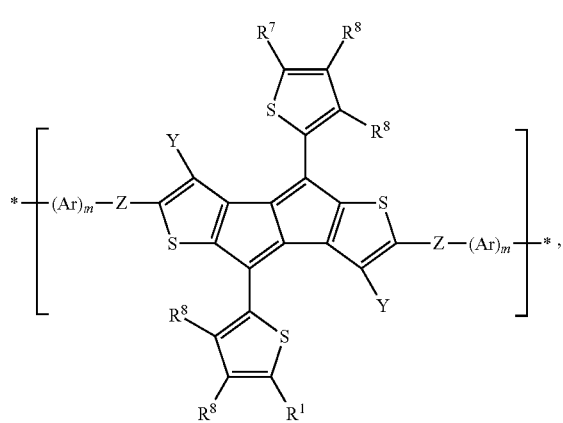

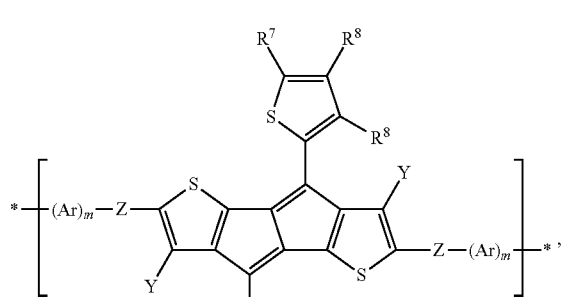

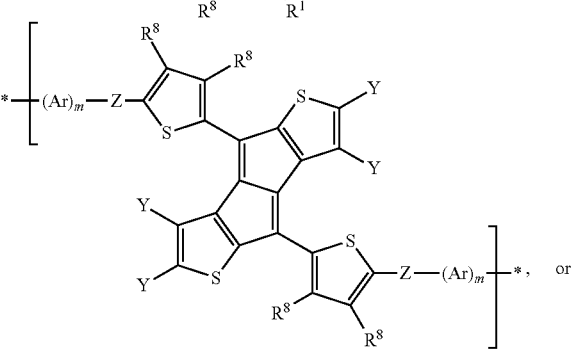

-continued

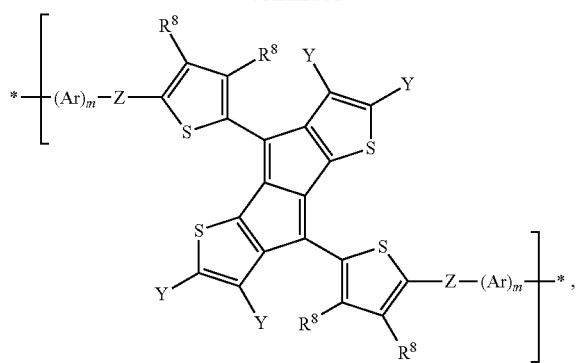

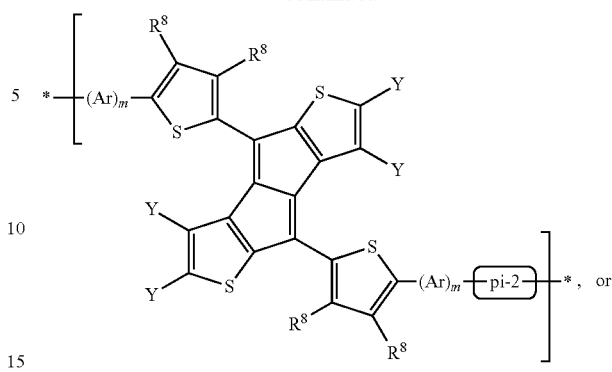, or wherein R⁸, at each occurrence, independently is H or R⁷; wherein R⁷ is selected from the group consisting of halogen, —CN, —NO₂, —OR, —SR, —C(O)OR, —C(O)R, —Si(R)₃, and R.

9. The polymer of claim 3, wherein the first repeating unit has the formula:

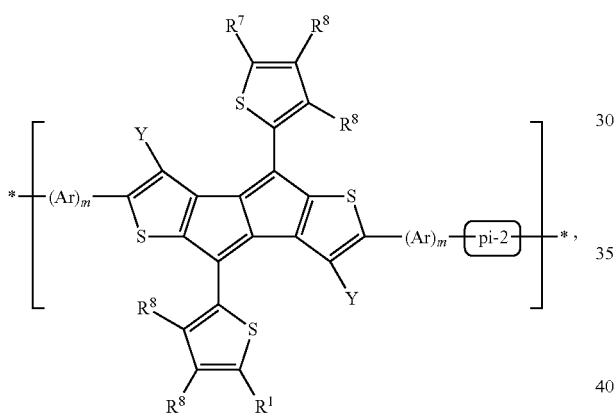

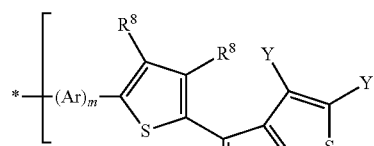

wherein:

R¹, at each occurrence, independently is selected from the group consisting of H, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group; and R⁸, at each occurrence, independently is H or R⁷; wherein R⁷, at each occurrence, independently is selected from the group consisting of halogen, a $C_{1-40}$ alkyl group, a $C_{2-40}$ alkenyl group, a $C_{2-40}$ alkynyl group, $C_{1-40}$ haloalkyl group, a $C_{1-40}$ alkoxy group, and a $C_{1-40}$ thioalkyl group.

10. The polymer of claim 3, wherein the first repeating unit has the formula:

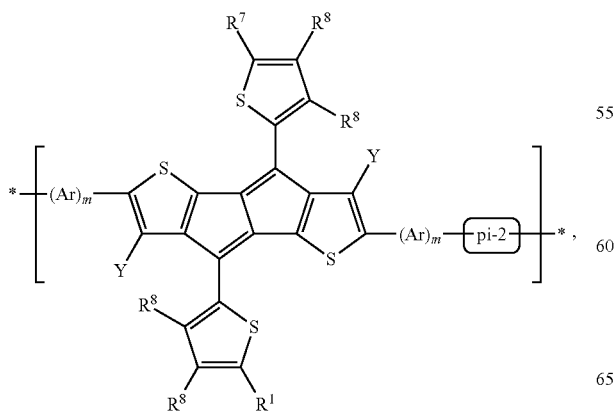

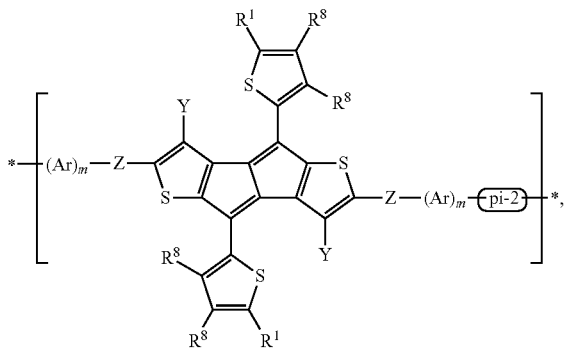

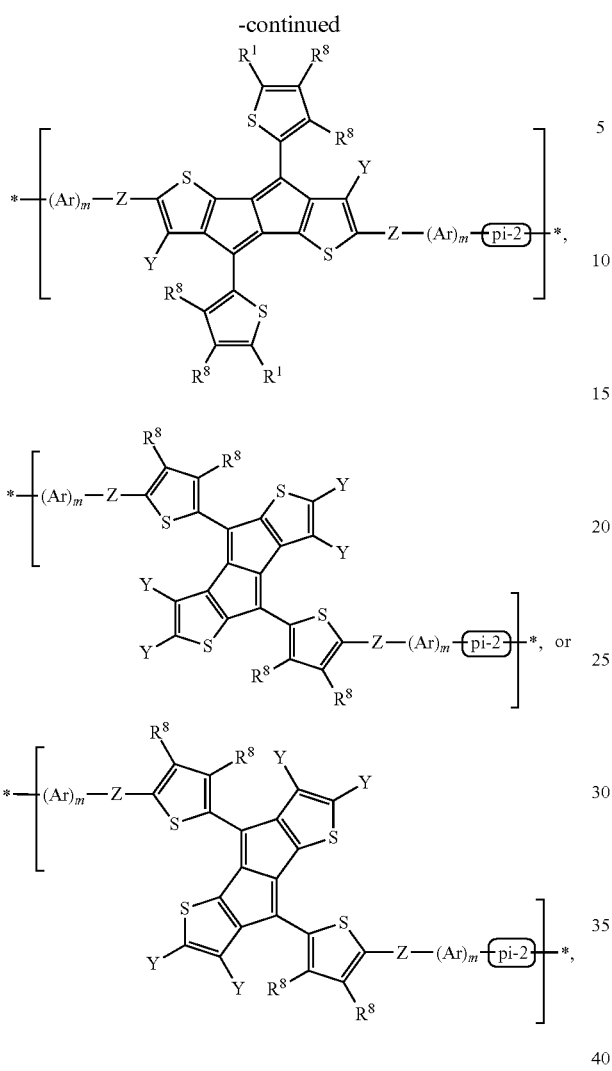

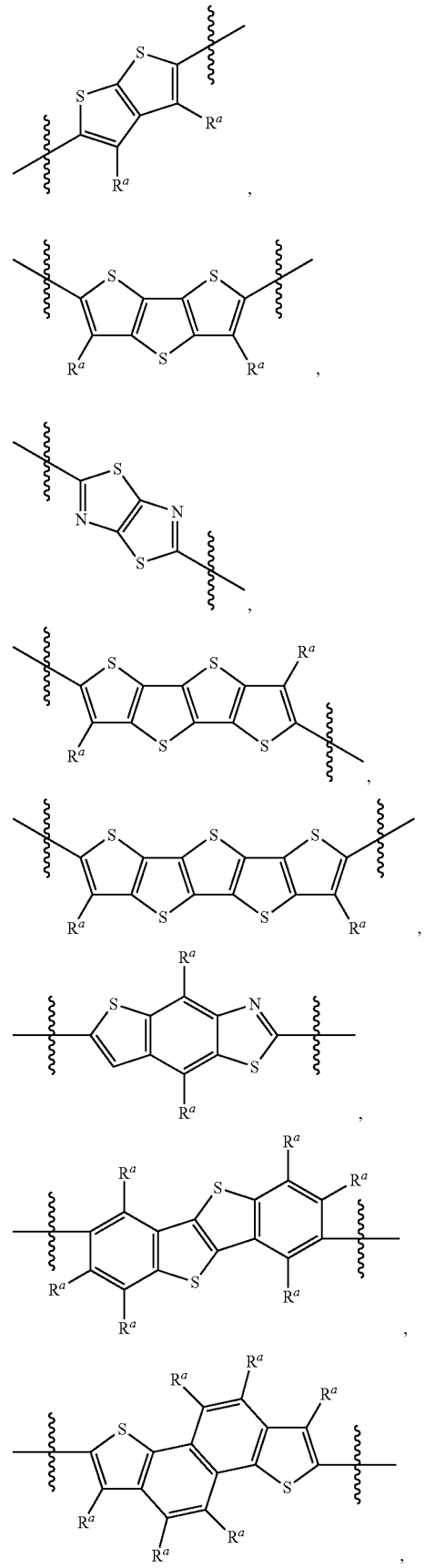

wherein:
R¹, at each occurrence, independently is selected from the group consisting of H, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group; and R⁸, at each occurrence, independently is H or R⁷; wherein R⁷, at each occurrence, independently is selected from the group consisting of halogen, a $C_{1-40}$ alkyl group, a $C_{2-40}$ alkenyl group, a $C_{2-40}$ alkynyl group, $C_{1-40}$ haloalkyl group, a $C_{1-40}$ alkoxy group, and a $C_{1-40}$ thioalkyl group.

11. The polymer of claim 9, wherein pi-2 is a conjugated polycyclic moiety selected from the group consisting of:

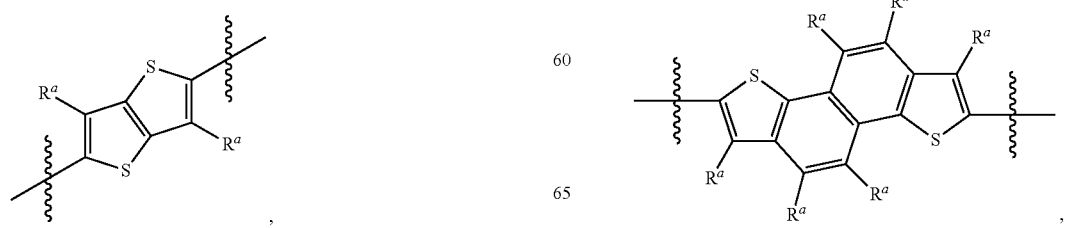

95
-continued
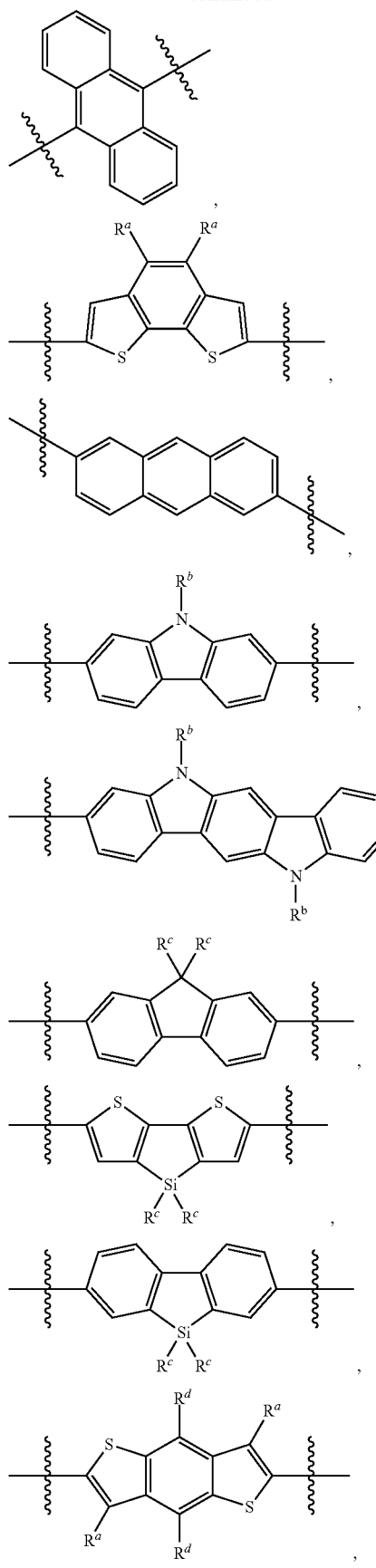
96
-continued
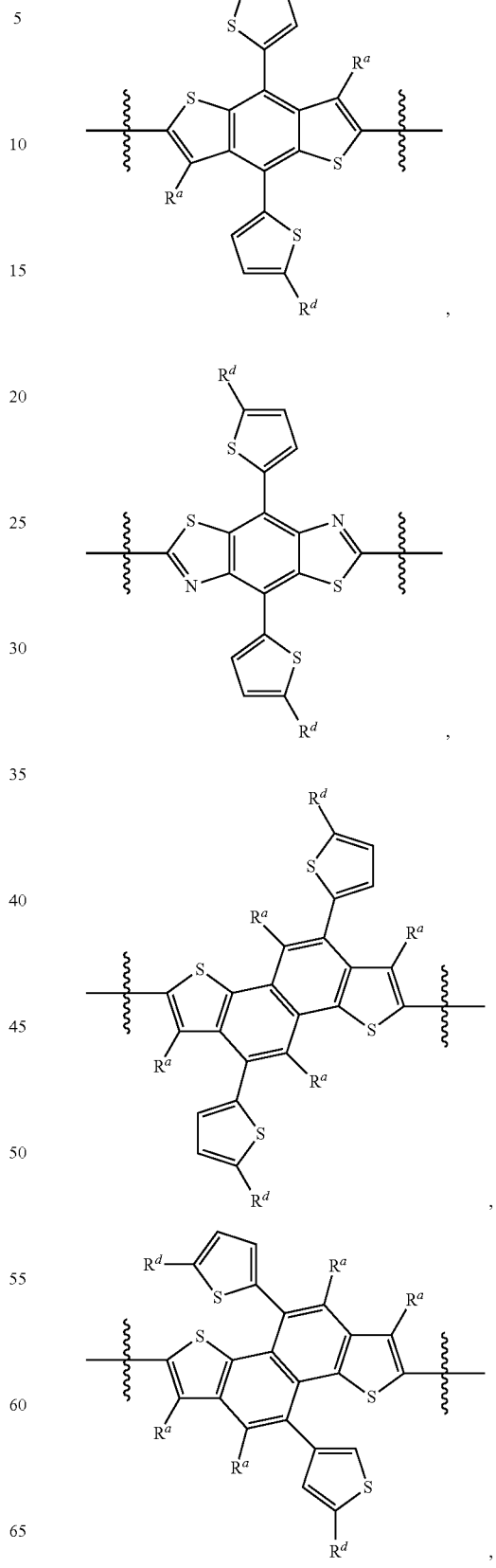

97
-continued
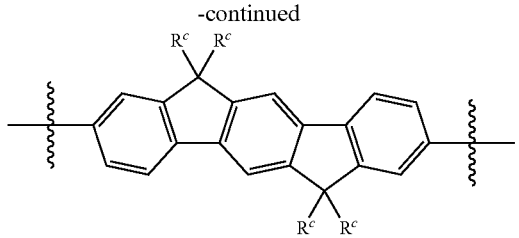
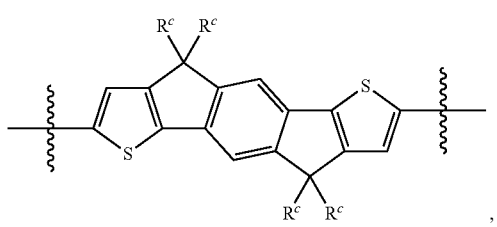
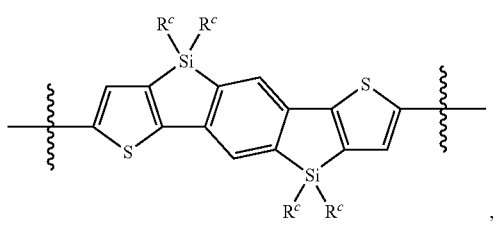
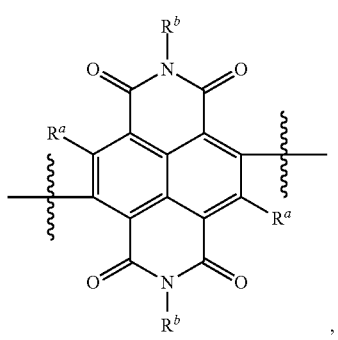
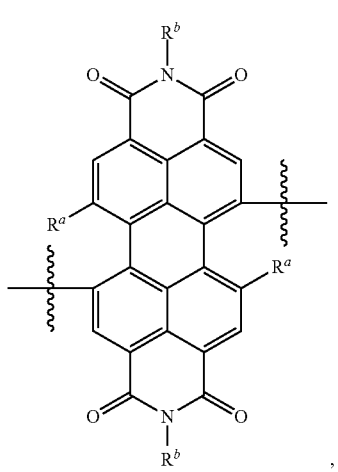
98
-continued
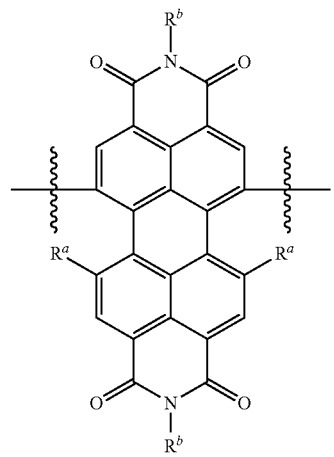
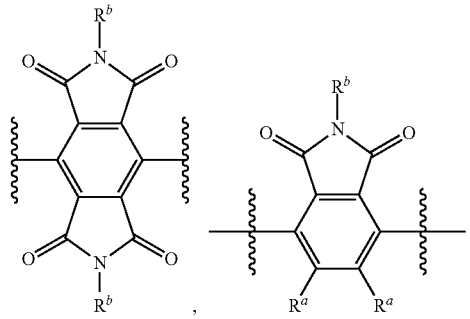
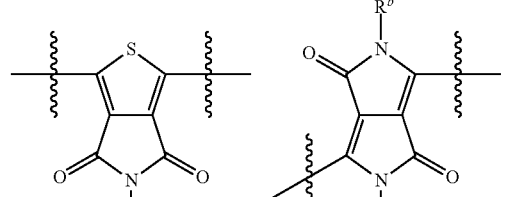
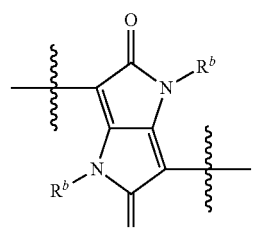
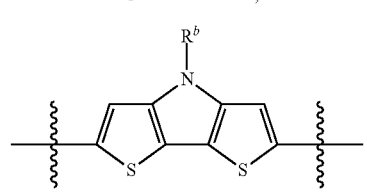
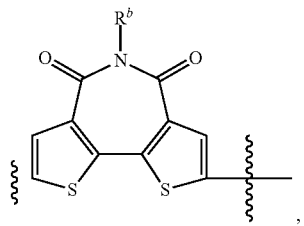

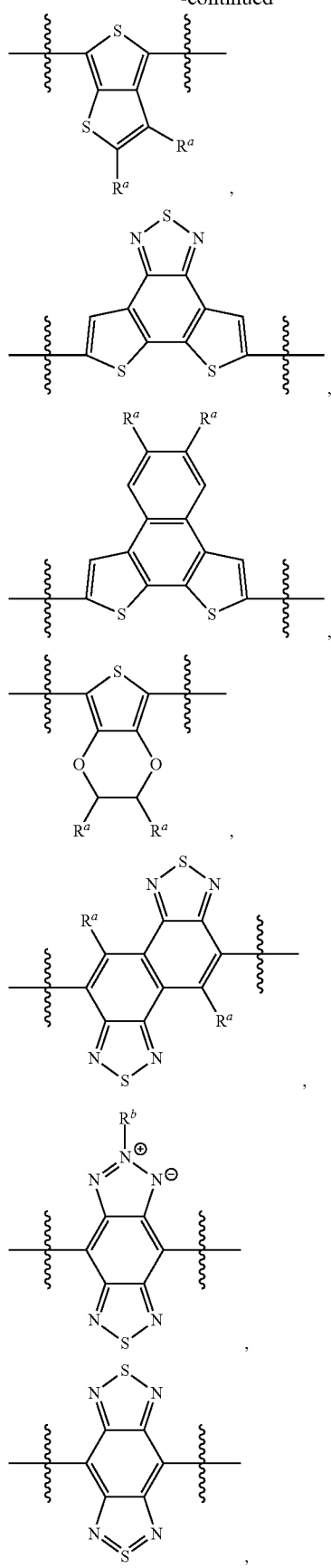
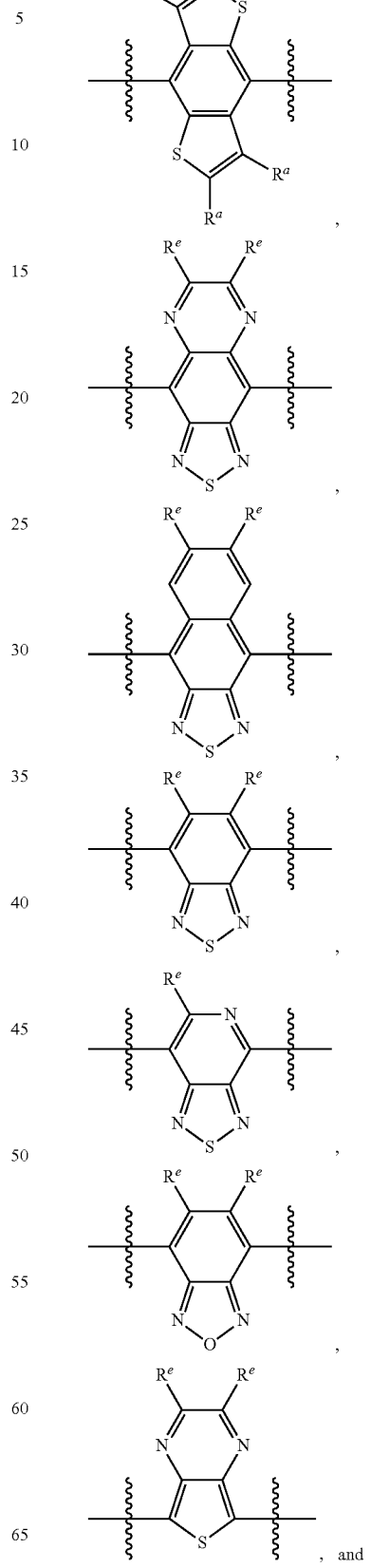

-continued

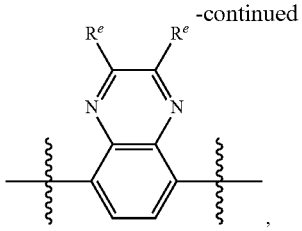

wherein:
R$^a$ is selected from the group consisting of H, F, Cl, —CN, R, —OR, —SR, —C(O)R, —OC(O)R, and —C(O)OR;
R$^b$ is selected from the group consisting of H, R, and -L-R$^f$;
R$^c$ is H or R;
R$^d$ is selected from the group consisting of H, F, Cl, —CN, R, —OR, —SR, —C(O)R, —OC(O)R, —C(O)OR, and -L-R$^f$;
R$^e$ is selected from the group consisting of H, F, Cl, —CN, R, —OR, —SR, —C(O)R, —OC(O)R, —C(O)OR, and R$^f$;
R$^f$ is a C$_{6-20}$ aryl group or a 5-20-membered heteroaryl group, each optionally substituted with 1-8 groups independently selected from the group consisting of F, Cl, —CN, R, —OR, and —SR;
L is selected from the group consisting of —O—, —S—, —C(O)—, —OC(O)—, —C(O)O—, and a covalent bond; and
R is selected from the group consisting of a C$_{1-40}$ alkyl group, a C$_{1-40}$ haloalkyl group, a C$_{2-40}$ alkenyl group, and a C$_{2-40}$ alkynyl group.

12. The polymer of claim 1, wherein the polymer comprises a second repeating unit of the formula:

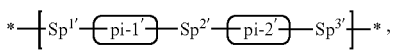

wherein:
pi-1' has the formula:

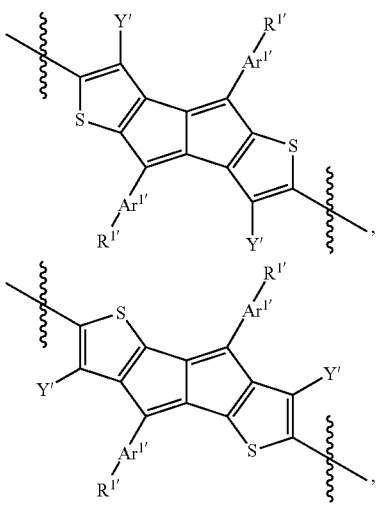

-continued

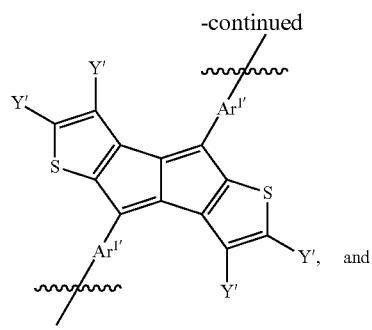

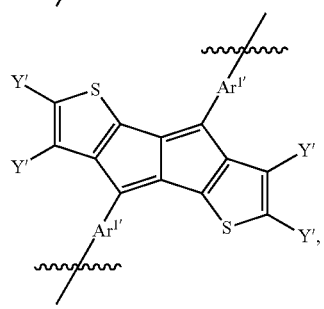

wherein:
Y', at each occurrence, independently is selected from the group consisting of halogen, R$^{1'}$, and —(Ar$^1$)$_{p'}$—R$^{1'}$;
Ar$^{1'}$, at each occurrence, independently is an optionally substituted divalent C$_{6-20}$ aryl or 5-20 membered heteroaryl group;
R$^{1'}$, at each occurrence, independently is selected from the group consisting of H, —C(O)OR$^4$, —C(O)R$^4$, —Si(R$^5$)$_3$, a C$_{1-40}$ alkyl group, a C$_{3-40}$ alkenyl group, a C$_{3-40}$ alkynyl group, C$_{1-40}$ haloalkyl group, a C$_{1-40}$ alkoxy group, and a C$_{1-40}$ thioalkyl group; wherein R$^4$ is H or a C$_{1-6}$ alkyl group; and R$^5$ is a C$_{1-6}$ alkyl group; and
p' is 1, 2, 3 or 4;
pi-2' is a covalent bond or an optionally substituted conjugated polycyclic moiety that is different from pi-1'; and
each of Sp$^{1'}$, Sp$^{2'}$, and Sp$^{3'}$ independently is a covalent bond or a conjugated spacer group having a formula selected from the group consisting of:

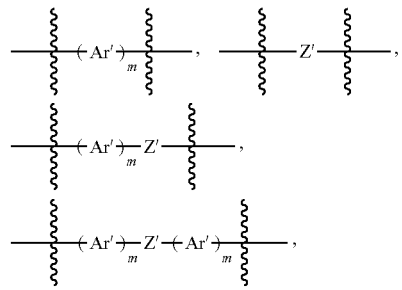

wherein each Ar' independently is an optionally substituted conjugated monocyclic moiety; Z' is a conjugated linear linker; and m' is 1, 2, 3 or 4; and
provided the second repeating unit is different from the first repeating unit.

13. The polymer of claim 12, wherein pi-1' is

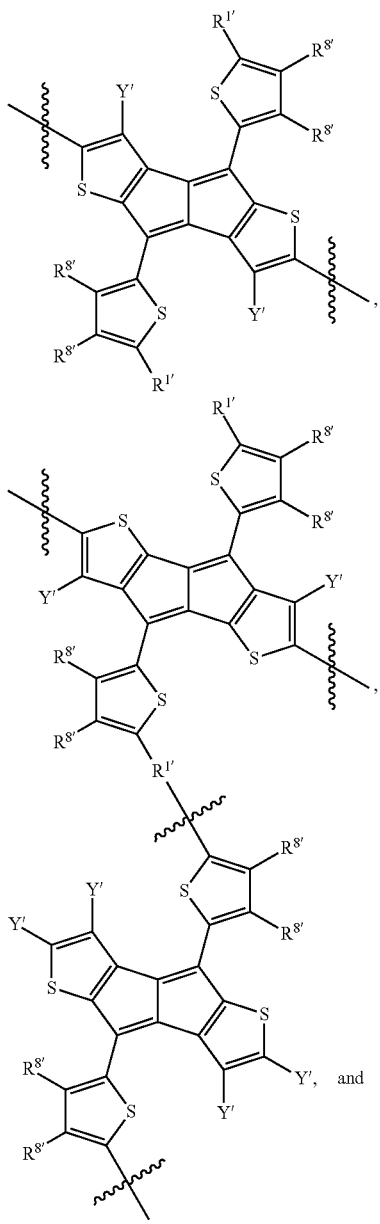

and wherein:
- Y', at each occurrence, independently is selected from the group consisting of H, halogen, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group;
- $R^{1'}$, at each occurrence, independently is selected from the group consisting of H, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group; and
- $R^{8'}$, at each occurrence, independently is H or $R^7$; wherein $R^7$, at each occurrence, independently is selected from the group consisting of halogen, a $C_{1-40}$ alkyl group, a $C_{2-40}$ alkenyl group, a $C_{2-40}$ alkynyl group, $C_{1-40}$ haloalkyl group, a $C_{1-40}$ alkoxy group, and a $C_{1-40}$ thioalkyl group.

14. The polymer of claim 12, where the first repeating unit and the second repeating unit are arranged in a random manner.

15. The polymer of claim 12 having the formula:

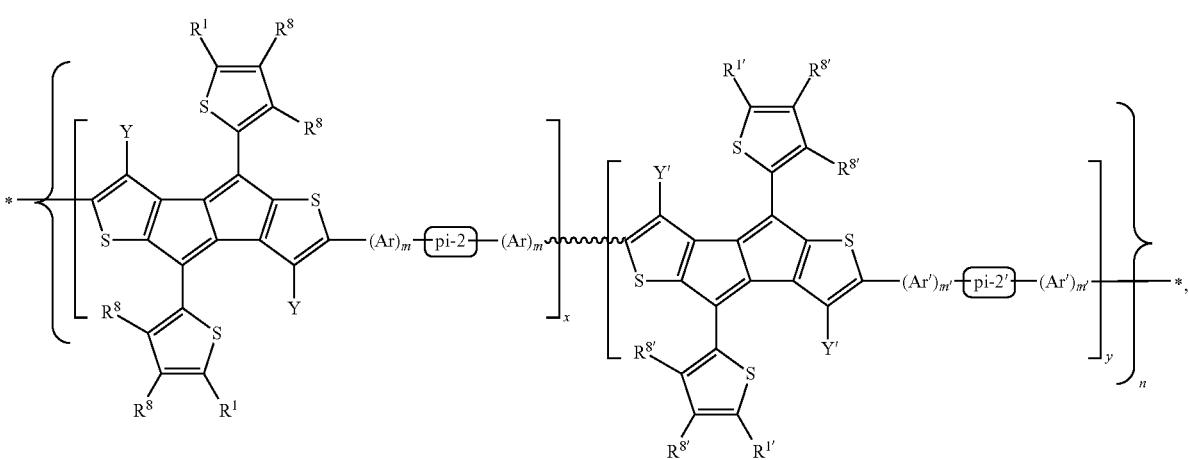

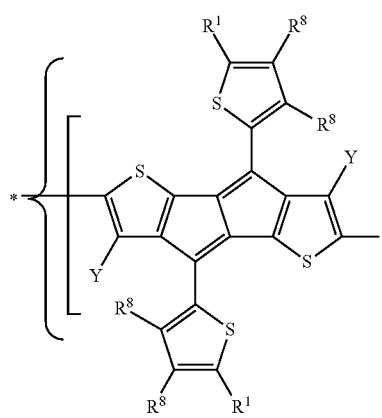
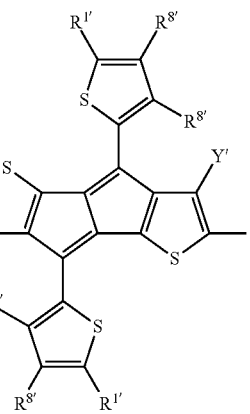

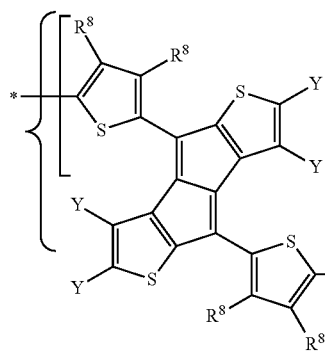
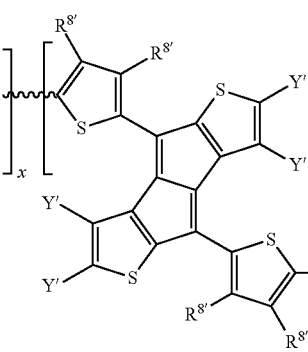

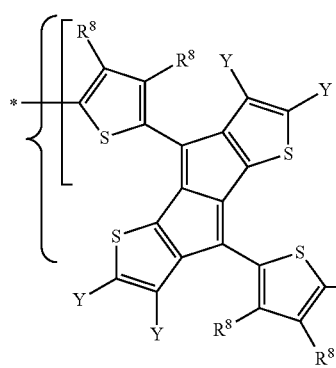
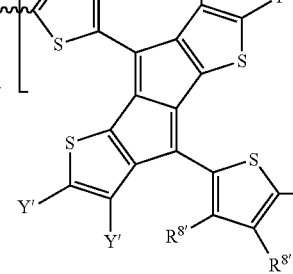

wherein:

Y and Y' independently are selected from the group consisting of H, halogen, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group;

$R^1$ and $R^{1'}$ independently are selected from the group consisting of H, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group;

$R^8$ and $R^{8'}$ independently are H or $R^7$; wherein $R^7$, at each occurrence, independently is selected from the group consisting of halogen, a $C_{1-40}$ alkyl group, a $C_{2-40}$ alkenyl group, a $C_{2-40}$ alkynyl group, $C_{1-40}$ haloalkyl group, a $C_{1-40}$ alkoxy group, and a $C_{1-40}$ thioalkyl group;

n is an integer in the range of 2 to 10,000; and x and y are real numbers representing mole fractions, wherein $0.05 \leq x \leq 0.95$, $0.05 \leq y \leq 0.95$, and the sum of x and y is about 1;

provided Ar is different from Ar', or pi-2 is different from pi-2'.

16. A polymer comprising a first repeating unit of the formula:

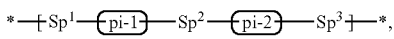

wherein:

pi-1 has a formula selected from the group consisting of:

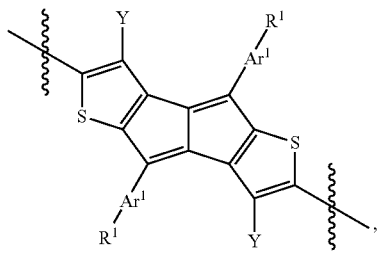

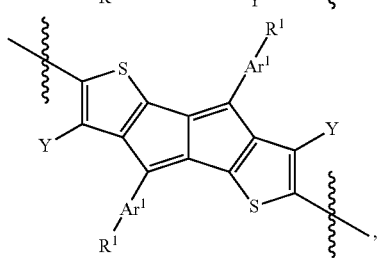

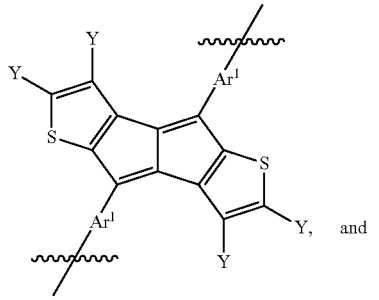, and

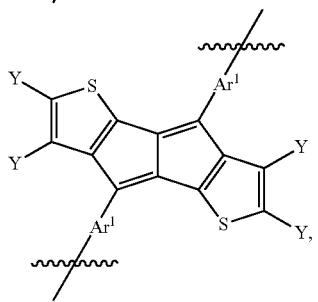

wherein:

Y, at each occurrence, independently is selected from the group consisting of halogen, $R^1$, and —$(Ar^1)_p$— $R^1$;

$Ar^1$, at each occurrence, independently is an optionally substituted divalent $C_{6-20}$ aryl or 5-20 membered heteroaryl group;

$R^1$, at each occurrence, independently is selected from the group consisting of H, —CN, —$NO_2$, —OR, —SR, —C(O)OR, —C(O)R, —Si(R)$_3$, and R; wherein R is selected from the group consisting of a $C_{1-40}$ alkyl group, a $C_{1-40}$ haloalkyl group, a $C_{2-40}$ alkenyl group, and a $C_{2-40}$ alkynyl group; and p is 1, 2, 3 or 4;

pi-2 is a covalent bond or an optionally substituted conjugated polycyclic moiety that is different from pi-1; and $Sp^1$, $Sp^2$, and $Sp^3$ independently are a covalent bond or a conjugated spacer group comprising at least one of a conjugated linear linker and an optionally substituted conjugated monocyclic moiety; and wherein the polymer comprises a second repeating unit of the formula:

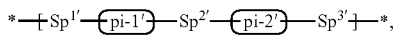

wherein:

pi-1' has the formula:

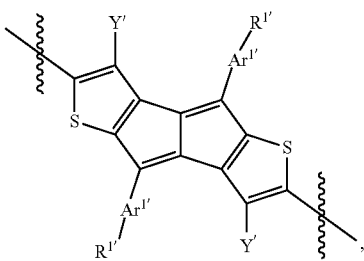

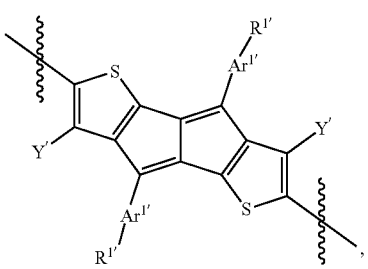, and

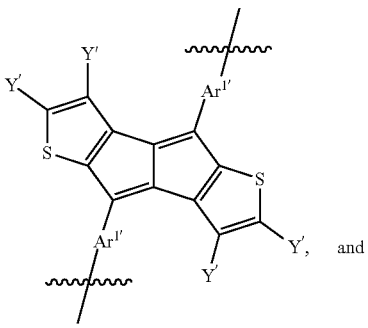

-continued

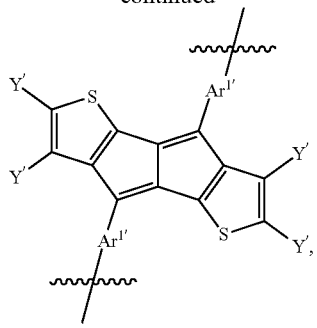

wherein:
Y', at each occurrence, independently is selected from the group consisting of halogen, $R^{1\prime}$, and —$(Ar^{1\prime})_{p'}$—$R^{1\prime}$;
$Ar^{1\prime}$, at each occurrence, independently is an optionally substituted divalent $C_{6-20}$ aryl or 5-20 membered heteroaryl group;
$R^{1\prime}$, at each occurrence, independently is selected from the group consisting of H, —C(O)OR$^4$, —C(O)R$^4$, —Si(R$^5$)$_3$, a $C_{1-40}$ alkyl group, a $C_{3-40}$ alkenyl group, a $C_{3-40}$ alkynyl group, $C_{1-40}$ haloalkyl group, a $C_{1-40}$ alkoxy group, and a $C_{1-40}$ thioalkyl group; wherein R$^4$ is H or a $C_{1-6}$ alkyl group; and R$^5$ is a $C_{1-6}$ alkyl group; and
p' is 1, 2, 3 or 4;
pi-2' is a covalent bond or an optionally substituted conjugated polycyclic moiety that is different from pi-1'; and
each of Sp$^{1\prime}$, Sp$^{2\prime}$, and Sp$^{3\prime}$ independently is a covalent bond or a conjugated spacer group having a formula selected from the group consisting of:

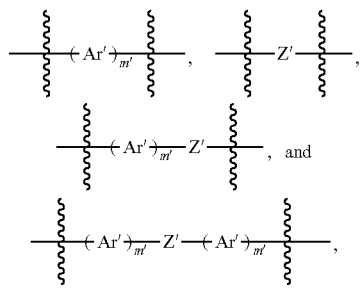

wherein each Ar' independently is an optionally substituted conjugated monocyclic moiety; Z' is a conjugated linear linker; and m' is 1, 2, 3 or 4; and
provided the second repeating unit is different from the first repeating unit.

17. The polymer of claim 16, where the first repeating unit and the second repeating unit are arranged in a random manner.

18. The polymer of claim 16, wherein Sp$^1$, Sp$^2$, and Sp$^3$ independently are selected from the group consisting of:

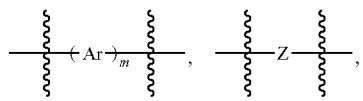

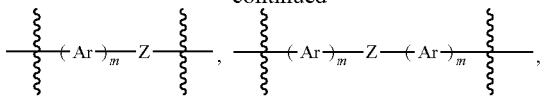

and a covalent bond, wherein each Ar independently is an optionally substituted conjugated monocyclic moiety; Z is a conjugated linear linker; and m is 1, 2, 3, 4 or 5.

19. The polymer of claim 18, wherein each Ar independently is an optionally substituted monocyclic 5- or 6-membered aryl or heteroaryl group.

20. The polymer of claim 18, wherein Z is selected from the group consisting of:

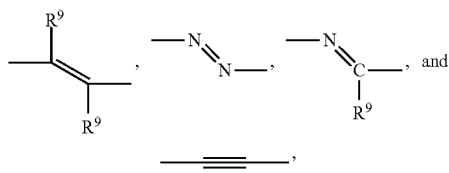

wherein each R$^9$ independently is selected from the group consisting of H, a halogen, CN, a $C_{1-40}$ alkyl group, a $C_{1-40}$ haloalkyl group, a $C_{1-40}$ alkoxy group, and a $C_{1-40}$ alkylthio group.

21. The polymer of claim 16, wherein pi-2 is a conjugated polycyclic moiety selected from the group consisting of:

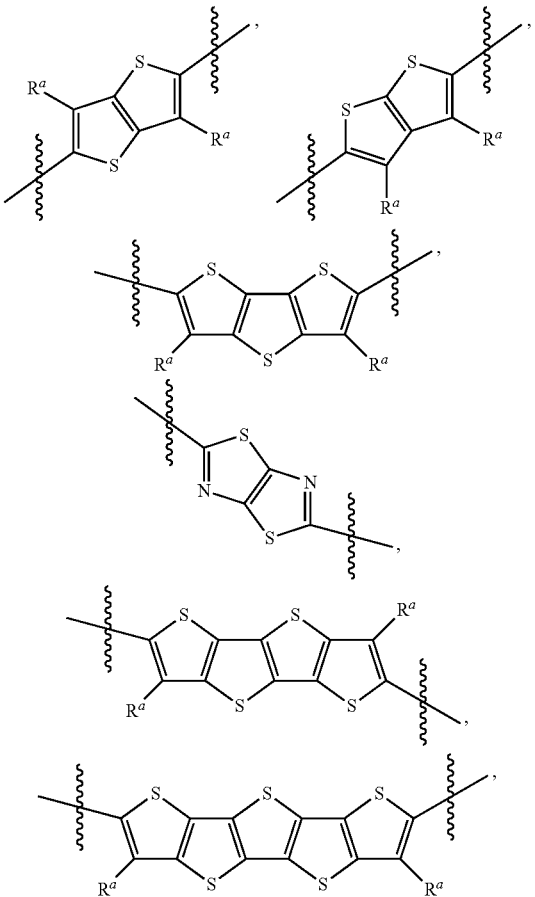

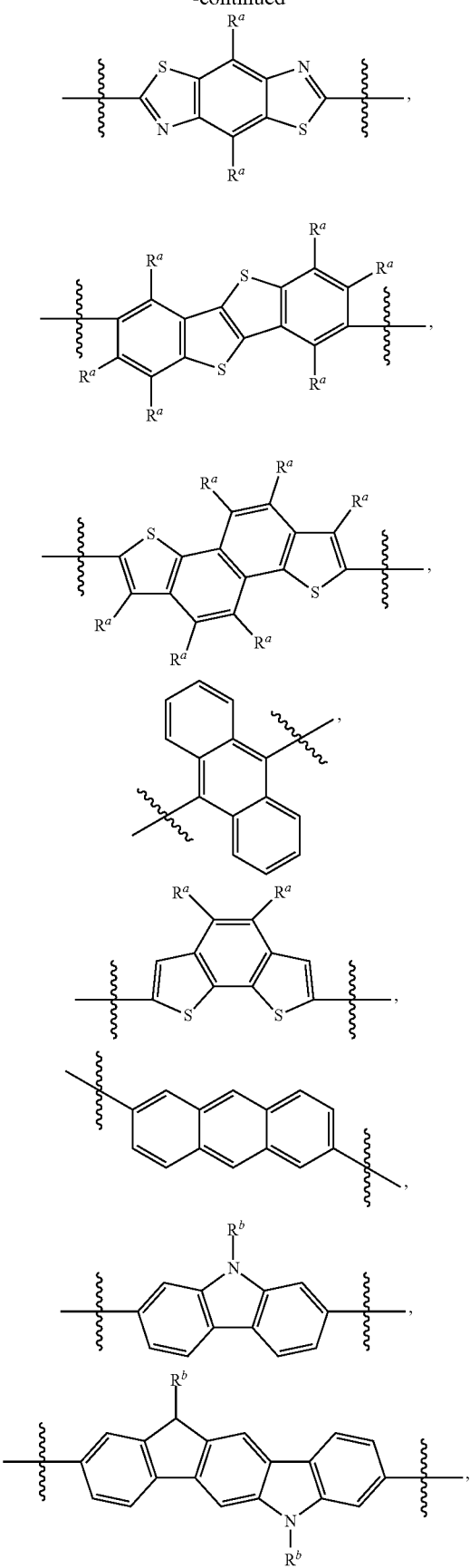
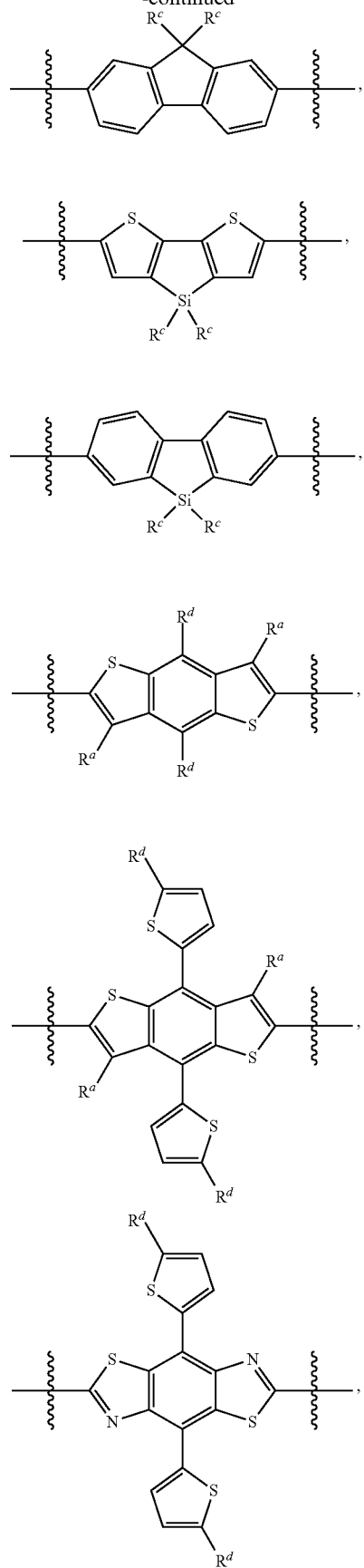

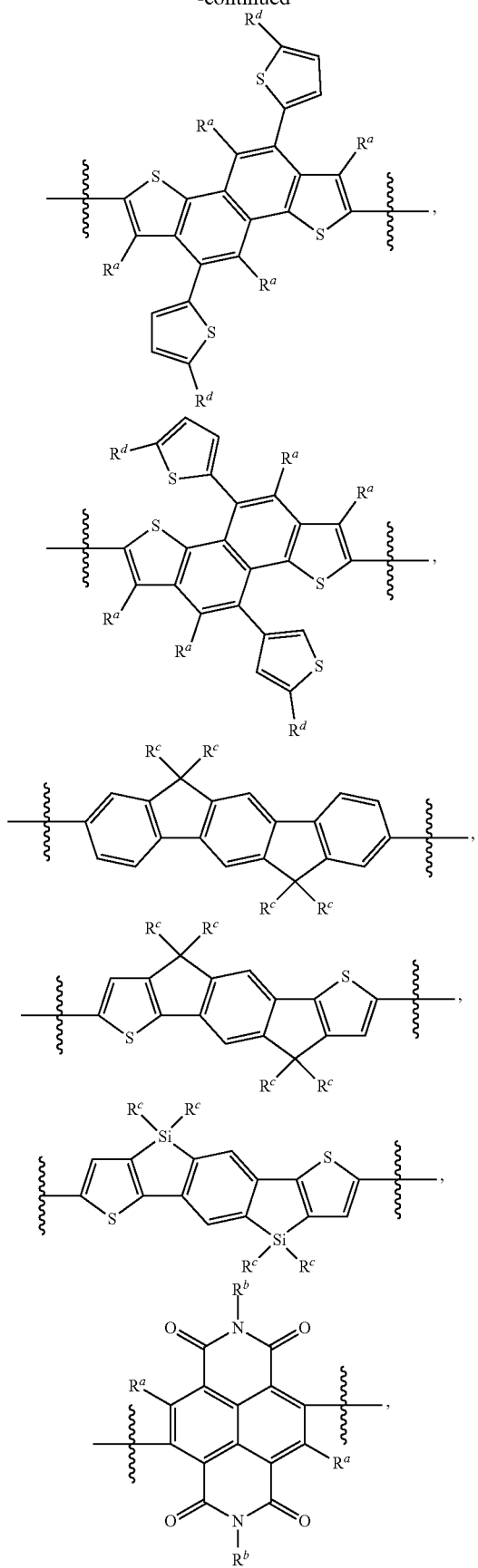
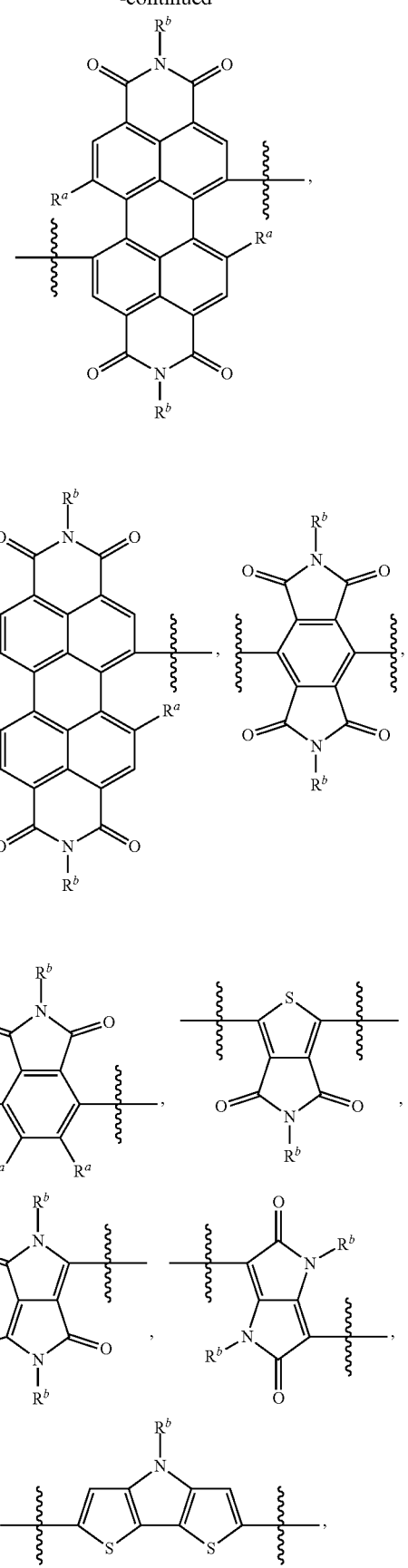

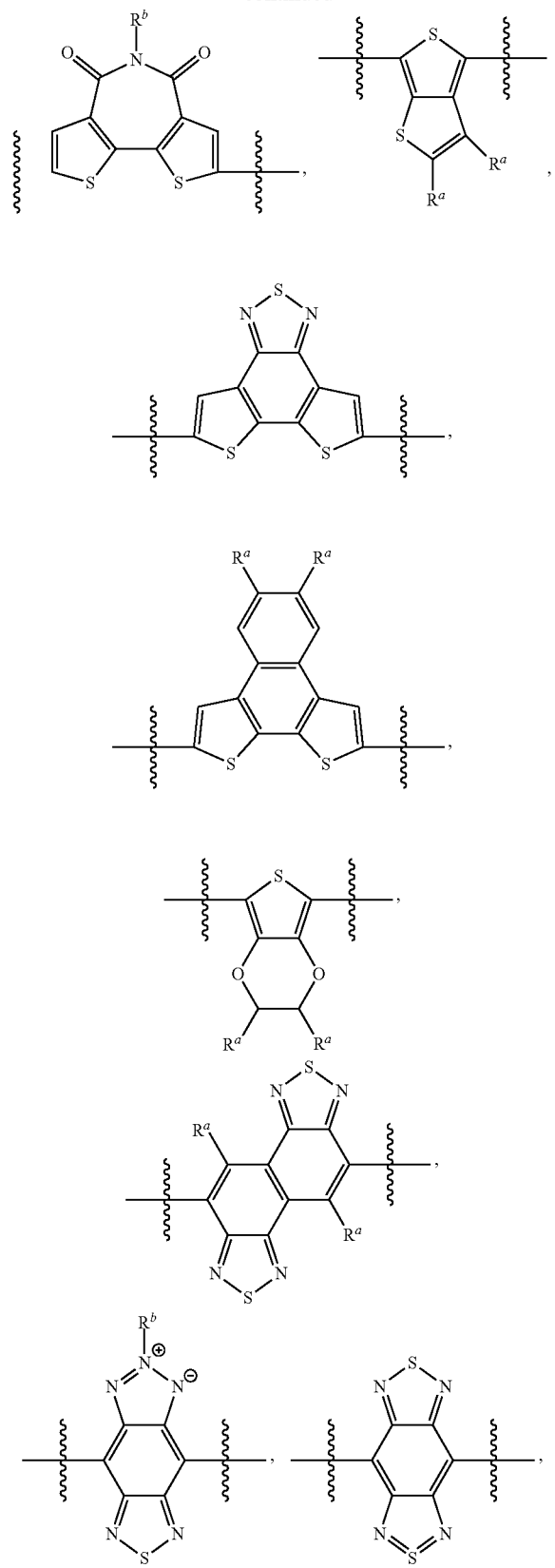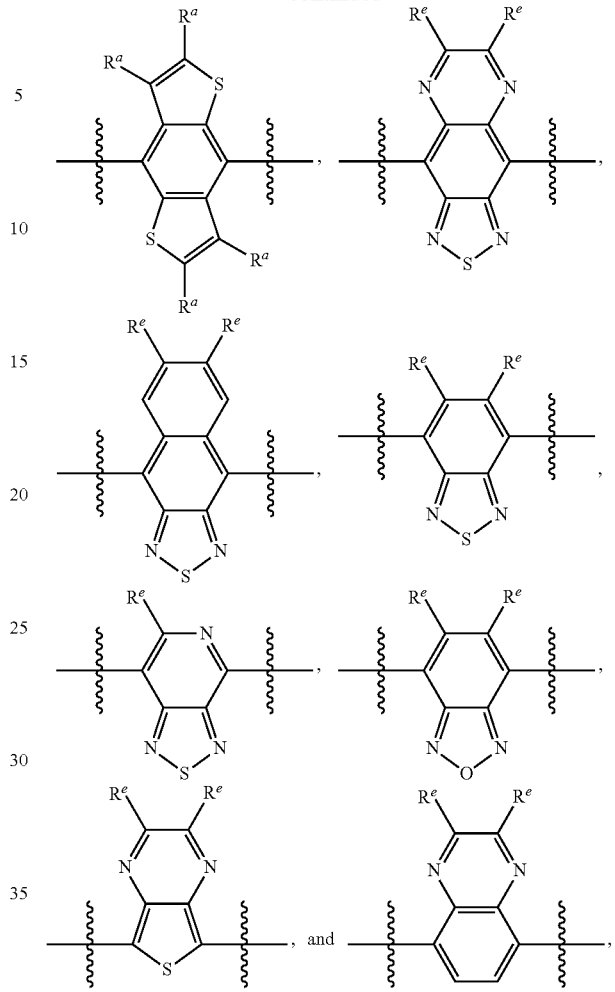

wherein:
R$^a$ is selected from the group consisting of H, F, Cl, —CN, R, —OR, —SR, —C(O)R, —OC(O)R, and —C(O)OR;
R$^b$ is selected from the group consisting of H, R, and -L-R$^f$;
R$^c$ is H or R;
R$^d$ is selected from the group consisting of H, F, Cl, —CN, R, —OR, —SR, —C(O)R, —OC(O)R, —C(O)OR, and -L-R$^f$;
R$^e$ is selected from the group consisting of H, F, Cl, —CN, R, —OR, —SR, —C(O)R, —OC(O)R, —C(O)OR, and R$^f$;
R$^f$ is a C$_{6-20}$ aryl group or a 5-20-membered heteroaryl group, each optionally substituted with 1-8 groups independently selected from the group consisting of F, Cl, —CN, R, —OR, and —SR;
L is selected from the group consisting of —O—, —S—, —C(O)—, —OC(O)—, —C(O)O—, and a covalent bond; and
R is selected from the group consisting of a C$_{1-40}$ alkyl group, a C$_{1-40}$ haloalkyl group, a C$_{2-40}$ alkenyl group, and a C$_{2-40}$ alkynyl group.

* * * * *